(12) United States Patent
Zhi et al.

(10) Patent No.: US 7,816,372 B2
(45) Date of Patent: Oct. 19, 2010

(54) 6-CYCLOAMINO-2-QUINOLINONE DERIVATIVES AS ANDROGEN RECEPTOR MODULATOR COMPOUNDS

(75) Inventors: Lin Zhi, San Diego, CA (US); Esther Martinborough, San Diego, CA (US); Yixing Shen, Encinitas, CA (US); Thomas Lot Stevens Lau, San Diego, CA (US); Min Wu, San Diego, CA (US); Yun Oliver Long, San Diego, CA (US)

(73) Assignee: Ligand Pharmaceuticals Incorporated, San Diego, CA (US)

( * ) Notice: Subject to any disclaimer, the term of this patent is extended or adjusted under 35 U.S.C. 154(b) by 954 days.

(21) Appl. No.: 10/566,569

(22) PCT Filed: Aug. 23, 2004

(86) PCT No.: PCT/US2004/027483

§ 371 (c)(1),
(2), (4) Date: Aug. 21, 2006

(87) PCT Pub. No.: WO2005/018573

PCT Pub. Date: Mar. 3, 2005

(65) Prior Publication Data

US 2007/0066650 A1 Mar. 22, 2007
US 2008/0227810 A9 Sep. 18, 2008

Related U.S. Application Data

(60) Provisional application No. 60/497,125, filed on Aug. 22, 2003.

(51) Int. Cl.
*C07D 215/38* (2006.01)
*A61K 31/02* (2006.01)

(52) U.S. Cl. .................. 514/312; 514/313; 514/314; 546/159; 546/161

(58) Field of Classification Search .......... 546/157, 546/161; 514/312, 313, 314
See application file for complete search history.

(56) References Cited

U.S. PATENT DOCUMENTS

| | | | |
|---|---|---|---|
| 3,847,988 A | 11/1974 | Gold | 562/802 |
| 3,928,686 A | 12/1975 | Poot et al. | 503/210 |
| 3,979,394 A | 9/1976 | Janssens et al. | 546/77 |
| 4,066,651 A | 1/1978 | Brittain et al. | 546/157 |
| 4,097,578 A | 6/1978 | Perronnet et al. | 514/389 |
| 4,138,490 A | 2/1979 | Brittain et al. | 514/312 |
| 4,202,895 A | 5/1980 | Inaba et al. | 514/266.31 |
| 4,415,572 A | 11/1983 | Tominaga et al. | 424/250 |
| 4,505,852 A | 3/1985 | Rasnick et al. | 530/329 |
| 4,636,505 A | 1/1987 | Tucker | 514/256 |
| 4,710,507 A | 12/1987 | Campbell et al. | 514/312 |
| 4,728,653 A | 3/1988 | Campbell et al. | 514/312 |
| 4,933,336 A | 6/1990 | Martin et al. | 514/222.5 |
| 4,981,784 A | 1/1991 | Evans et al. | 435/6 |
| 5,071,773 A | 12/1991 | Evans et al. | 436/501 |
| 5,081,242 A | 1/1992 | Combs | 544/52 |
| 5,576,324 A | 11/1996 | Kyotani et al. | 514/291 |
| 5,677,336 A | 10/1997 | Jones et al. | 514/546 |
| 5,688,808 A | 11/1997 | Jones et al. | 514/285 |
| 5,688,810 A | 11/1997 | Jones et al. | 514/311 |
| 5,693,646 A | 12/1997 | Jones et al. | 514/285 |
| 5,693,647 A | 12/1997 | Jones et al. | 514/285 |
| 5,696,127 A | 12/1997 | Jones et al. | 514/285 |
| 5,696,130 A | 12/1997 | Jones et al. | 514/291 |
| 5,696,133 A | 12/1997 | Jones et al. | 514/314 |
| 5,977,108 A | 11/1999 | Kikuchi et al. | 514/249 |
| 5,994,544 A | 11/1999 | Jones et al. | 546/62 |
| 6,017,924 A | 1/2000 | Edwards et al. | 514/292 |
| 6,093,821 A | 7/2000 | Jones et al. | 544/333 |
| 6,121,450 A | 9/2000 | Jones et al. | 546/81 |
| 6,180,794 B1 | 1/2001 | Edwards et al. | 546/152 |
| 6,340,704 B1 | 1/2002 | Marui et al. | 514/463 |
| 6,358,948 B1 | 3/2002 | Zhang et al. | 514/230.5 |
| 6,380,207 B2 | 4/2002 | Coghlan et al. | 514/285 |
| 6,448,405 B1 | 9/2002 | Jones et al. | 546/62 |
| 6,462,038 B1 | 10/2002 | Higuchi et al. | 514/224.5 |
| 6,498,154 B1 | 12/2002 | Grubb et al. | 514/141 |
| 6,506,766 B1 | 1/2003 | Coghlan et al. | 514/285 |
| 6,534,516 B1 | 3/2003 | Edwards et al. | 514/285 |
| 6,566,372 B1 * | 5/2003 | Zhi et al. | 514/312 |

(Continued)

FOREIGN PATENT DOCUMENTS

| | | |
|---|---|---|
| DE | 2334738 | 1/1975 |
| DE | 3810706 A | 10/1989 |
| EP | 0272910 A | 6/1988 |
| EP | 0356230 A | 2/1990 |
| EP | 0542609 | 5/1993 |
| EP | 0638571 | 2/1995 |
| WO | 89/07441 | 8/1989 |
| WO | 94/23068 A1 | 10/1994 |
| WO | 96/19458 A2 | 6/1996 |
| WO | 96/41013 A1 | 12/1996 |

(Continued)

OTHER PUBLICATIONS

Alabaster, et al., "2(1H)-quinolinones with cardiac stimulant activity. 2. Synthesis and biological activities of 6-(N-linked, five-membered heteroaryl) derivatives." J. Med. Chem., 32:575-583 (1989).

(Continued)

*Primary Examiner*—D. Margaret Seaman
(74) *Attorney, Agent, or Firm*—K & L Gates LLP; Stephanie Seidman; Frank J. Miskiel

(57) ABSTRACT

The present invention is directed to compounds, pharmaceutical compositions, and methods for modulating processes mediated by AR. Also provided are methods of making such compounds and pharmaceutical compositions.

42 Claims, No Drawings

U.S. PATENT DOCUMENTS

| | | | | |
|---|---|---|---|---|
| 6,569,896 | B2 | 5/2003 | Dalton et al. | 514/493 |
| 6,635,759 | B2 | 10/2003 | Uray et al. | 544/128 |
| 6,667,313 | B1 | 12/2003 | Hamann et al. | 514/292 |
| 6,673,799 | B1 | 1/2004 | Taniguchi et al. | 514/253.01 |
| 6,696,459 | B1 | 2/2004 | Jones et al. | 514/285 |
| 6,964,973 | B2 * | 11/2005 | Zhi et al. | 514/312 |
| 7,071,205 | B2 | 7/2006 | Zhi et al. | 514/285 |
| 7,084,151 | B2 | 8/2006 | Zhi et al. | 514/285 |
| 7,214,690 | B2 | 5/2007 | Higuchi et al. | 514/314 |
| 2002/0094983 | A1 | 7/2002 | Zhang et al. | 514/230.5 |
| 2002/0183314 | A1 | 12/2002 | Higuchi et al. | 514/224.5 |
| 2002/0183346 | A1 | 12/2002 | Zhi et al. | 514/291 |
| 2003/0045511 | A1 | 3/2003 | Grubb et al. | 514/141 |
| 2003/0055094 | A1 | 3/2003 | Sun et al. | 514/379 |
| 2003/0149268 | A1 | 8/2003 | Hamann et al. | 546/81 |
| 2003/0186970 | A1 | 10/2003 | Higuchi et al. | 514/224.2 |
| 2003/0216388 | A1 | 11/2003 | Zhang et al. | 514/230.5 |
| 2003/0216428 | A1 | 11/2003 | Miyakawa et al. | 514/312 |
| 2004/0186132 | A1 | 9/2004 | Jones et al. | 514/312 |
| 2005/0288350 | A1 | 12/2005 | Zhi et al. | 514/397 |

FOREIGN PATENT DOCUMENTS

| | | |
|---|---|---|
| WO | 97/49709 | 12/1997 |
| WO | 99/58486 | 11/1999 |
| WO | 00/66680 | 11/2000 |
| WO | 01/16108 A2 | 3/2001 |
| WO | 01/16133 | 3/2001 |
| WO | 01/16139 | 3/2001 |
| WO | 01/27086 | 4/2001 |
| WO | WO 02/16310 | 2/2002 |
| WO | 02/22585 | 3/2002 |
| WO | 02/066475 | 8/2002 |
| WO | 02/068427 | 9/2002 |
| WO | 03/037905 A1 | 5/2003 |
| WO | WO 03/090672 | 11/2003 |
| WO | 2004/045518 | 6/2004 |
| WO | 2005/018573 A2 | 3/2005 |
| WO | 2005/090282 A1 | 9/2005 |
| WO | 016108 * | 3/2009 |
| WO | WO 2009/082437 | 7/2009 |

OTHER PUBLICATIONS

Bains & Tacke, "Silicon chemistry as a novel source of chemical diversity in drug design," Curr. Opin. Drug Discov. Devel. 6:526-43 (2003).

Berger et al., "Interaction of glucocorticoid analogues with the human glucocorticoid receptor," J. Steroid Biochem. Mol. Biol., 41:733-738 (1992).

Bissell et al., "Synthesis and Chemistry of 7-Amino-4-(trifluoromethyl) coumarin and Its Amino Acid and Peptide Derivatives," J. Org. Chem., 45(12):2283-2287 (1980).

Certified English translation of German patent, DE 3810706 published Oct. 5, 1989 entitled "Substituted Cumarine Derivatives, Method for their Production, and Their Use As an Application with an herbicide Effect."

Croston, G. E., Milan, L. B., Marschke, K. B., Reichman, M. and Briggs, M. R. Androgen receptor-mediated antagonism of estrogen-dependent low density lipoprotein receptor transcription in cultured hepatocytes Endocrinology 138(9):3779-3786 (1997).

Derwert citing French patent EP 0542609 published May 19, 1993, for: "New 3-sulphonylamino-2(1H)-quinolinone derivs.- as excitatory aminoacid receptor blockers for treating cerebrovascular accident, spinal trauma, amyotrophic lateral sclerosis, Alzheimer's disease and schizophrenia."

Derwert citing German patent DE 2334738 published Jan. 1, 1975, for: "Hair-dyestuff for oxidation-dyeing process-contg. 4 hydroxy-quinolone-2-derivs. as coupling components."

Derwert citing German patent, DE 3810706 published Oct. 5, 1989, for: "New coumarin derivs. contg. imide gp.- useful as selective herbicides."

Derwert citing Japanese patent WO 01/27086 published Apr. 19, 2001, for: "New tetrahydroquinoline derivatives useful as androgen receptor binding agents for treating e.g. males sexual dysfunction."

Edwards, et al., "5-Aryl-1,2-dihydro-5H-chromeno [3,4-f]quinolines as Potent, Orally Active, Nonsteroidal Progesterone Receptor Agonists: The Effect of D-Ring Substitutes," Journal of Medicinal Chem. 41:303-310 (1998).

Edwards, et al., "New nonsteroidal androgen receptor modulators based on4-(trifluoromethyl)-2(1H)-pyrrolidino[3,2-g] quinolinone," Bioorg Med Chem Lett.,8(7)745-50 (1998).

Edwards, et al., "Nonsteroidal androgen receptor agonists based on4-(trifluoromethyl)-2H-pyrano[3,2-g]quinolin-2-one," Bioorg Med Chem Lett., 9(7)1003-8 (1999).

Edwards, et al., "Preparation, Resolution, and Biological Evaluation of 5-Aryl-1,2-dihydro-5H-chromeno[3,4-f]quinolines: Potent, Orally Active, Nonsteroidal Progesterone Receptor Agonists," Journal of Medicinal Chem. 41:2779-85 (1998).

Evans, et al., "The Steroid and Thyroid Hormone Receptor Superfamily," Science, 240:889-895 (1998).

Fingl et al. "The Pharmacological Basis of Therapeutics", Ch.1 p. 1 (1975).

Hamann, et al, "Discovery of a potent, orally active, nonsteroidal androgen receptor agonist: 4-ethyl-1,2,3,4-tetrahydro-6-(trifluoromethyl)-8-pyridono[5,6-g]- quinoline (LG121071)" J Med Chem., 42(2):210-2 (1999).

Hamann, et al. "Synthesis and biological activity of a novel series of nonsteroidal, peripherally selective androgen receptor antagonists derived from 1,2-dihydropyridono[5,6-g]quinolines.," J. Med. Chem., 41(4) 623-639 (1998).

Hamann, et al., "Nonsteroidal progesterone receptor antagonists based on aconformationally-restricted subseries of6-aryl-1,2-dihydro-2,2,4-trimethylquinolines," Bioorg Med Chem Lett., 8(19)2731-6(1998).

Higuchi, et al., "4-Alkyl- and 3,4-dialkyl-1,2,3,4-tetrahydro-8-pyridono[5,6-g]quinolinespotent, nonsteroidal androgen receptor agonists." Bioorg Med Chem Lett., 9(9)1335-40.(1999).

Kong, et al., "Effects of isosteric pyridone replacements in androgen receptor antagonistsbased on 1,2-dihydro- and1,2,3,4-tetrahydro-2,2-dimethyl-6-trifluoromethyl-8-pyridono[5,6-g]quinolines," Bioorg Med Chem Lett., 10(5)411-4.(2000).

Labrie, et al., "Science behind total androgen blockade: from gene to combination therapy," Clin. Invest. Med., 16: 475-492 (1993).

Lawson, et al., "Androgen responsiveness of the pituitary gonadotrope cell line LbetaT2," J Endocrinol., 170(3)601-7.(2001).

Luke, et al., "The Male Sex Accessory Tissues; Structure, Androgen Action, and Physiology," The Physiology of Reproduction, 1435-1487 (1994).

Miner, J. N. and Tyree, C. M. "Drug discovery and the intracellular receptor family," Vitamins and Hormones, 62:253-280 (2001).

Negro-Vilar A. Selective androgen receptor modulators (SARMs) a novel approach to androgen therapy for the new millennium. J Clin Endocrinol Metab., 84(10)3459-62. (1999).

Patel, et al., "Synthesis of substituted 6-(3',5'-dimethyl-1H-pyrazol-1'-yl) quinolines and evaluation of their biological activities" Indian J. Chem., 29B:836-842 (1990).

Pathirana et al., "Nonsteroidal human progesterone receptor modulators from the marine alga Cymopolia barbata," Mol. Pharm. 47:630-635 (1995).

Pooley, et al., "Discovery and preliminary SAR studies of a novel, nonsteroidal progesterone receptor antagonist pharmacophore.," J. Med. Chem., 41(18): 3461-3466 (1998).

Rodbard, "Mathematics and statistics of ligand assays: an illustrated guide" in: J. Langon and J. J. Clapp, eds., Ligand Assay, Masson Publishing U.S.A., Inc., New York, pp. 45-99, (1981).

Rosen, and Negro-Vilar, "Novel, non-steroidal, selective androgen receptor modulators (SARMs) with anabolic activity in bone and muscle and improved safety profile," Journal of Musculoskeletal Neuronal Interactions/Journal of Musculoskeletal Neuronal Interactions, 2(3):222-224 (2002).

Rosen, et al., "Intracellular receptors and signal transducers and activators of transcription superfamilies—novel targets for small-molecule drug discovery," Journal of Medicinal Chemistry 38:25;4855-4874 (1995).

Simental, et al., Transcriptional Activation and Nuclear Targeting Signals of the Human Androgen Receptor, J Biol Chem., 266(1):510-518 (1991).

Singh et al., "Androgen receptor antagonists (antiandrogens): structure-activity relationships," Curr. Med. Chem. 7(2): 211-247 (2000).

Tacke & Zilch, "Sila-substitution—a useful strategy for drug design?" Endeavour, New Series, 10(4):191-197 (1986).

Tegley, et al., "5-Benzylidene 1,2-dihydrochromeno[3,4-f]quinolines, a novel class of nonsteroidal human progesterone receptor agonists," J Med Chem., 41(22):4354-9 (1998).

Walsh, et al., "Inhibition of extratesticular stimuli to prostatic growth in the castrated rat by antiandrogens," Endocrinology 86: 624 (1970).

Wen, D. X. and McDonnell, D. P. Advances in our understanding of ligand-activated nuclear receptors Current Opinion in Biotechnology 6(5):582-589 (1995).

Yin, et al., "Key structural features of nonsteroidal ligands for binding and activation of the androgen receptor," Molecular Pharmacology, 63(1): 211-223 (2003).

Zhi et al. "Nonsteroidal progesterone receptor antagonists based on 6-thiophenehydroquinolines," Bioorg Med Chem Lett.,10(5)415-418 (2000).

Zhi, et al., "5-Aryl-1,2,3,4-tetrahydrochromeno[3,4-f]quinolin-3-ones as a novel class of nonsteroidal progesterone receptor agonists effect of A-ring modification," J Med Chem.,42(8)1466-72.(1999).

Zhi, et al., "5-Aryl-1,2-dihydrochromeno [3,4f]quinolines: A Novel Class of Nonsteroidal Human Progesterone Receptor Agonists," *Journal of Medicinal Chem.* 41:291-302 (1998).

Zhi, et al., "Switching androgen receptor antagonists to agonists by modifying C-ringsubstituents on piperidino[3,2-g]quinolinone," Bioorg Med Chem Lett., 9(7)1009-12.(1999).

Zhi, L. and Martinborough, E. Chapter 17. Selective androgen receptor modulators (SARMs) Annual Reports in Medicinal Chemistry, 36:169-180 (2001).

* cited by examiner

6-CYCLOAMINO-2-QUINOLINONE DERIVATIVES AS ANDROGEN RECEPTOR MODULATOR COMPOUNDS

RELATED APPLICATIONS

This application is the National Stage of International Application. No. PCT/US2004/027483, filed Aug. 23, 2004, which claims the benefit of priority to U.S. Provisional Application Ser. No. 60/497,125, filed Aug. 22, 2003, the entire disclosure of each of which is incorporated herein by reference in its entirety.

FIELD OF THE INVENTION

This invention relates to nonsteroidal compounds that are modulators (i.e., agonists, partial agonists and antagonists) of androgen receptor, and to methods for the making and use of such compounds.

BACKGROUND OF THE INVENTION

Intracellular receptors (IRs) form a class of structurally-related genetic regulators scientists has named "ligand dependent transcription factors" (R. M. Evans, Science, 240:889, 1988). Steroid receptors are a recognized subset of the IRs, including androgen receptor, progesterone receptor (PR), estrogen receptor (ER), glucocorticoid receptor (GR), and mineralcorticoid receptor (MR). Regulation of a gene by such factors requires both the IR itself and a corresponding ligand, which has the ability to selectively bind to the IR in a way that affects gene transcription.

The natural hormones for steroid receptors have been known for a long time, such as testosterone for the androgen receptor. A synthetic compound that binds to an IR and mimics the effect of the native hormone is referred to as an "agonist", while a compound that inhibits the effect of the native hormone is called an "antagonist". The term "modulators" refers to a group of compounds that have a spectrum of activities from agonist, partial agonist to antagonist in different target tissues.

Androgen receptor modulators are known to play an important role in health of both men and women. For example, androgen receptor antagonists, such as cyproterone acetate, flutamide and casodex, are useful in the treatment of prostatic hyperplasia and cancer of the prostate. Androgen receptor agonists, such as testosterone and fluoxymesterone, are used in the treatment of hypogonadism and muscle wasting diseases. Due to increased life expectancies, development of tissue selective, safer, orally active androgen receptor modulators are desirable to improve quality of life.

A group of 6-cycloamino-quinolinone derivatives was recently described as androgen receptor modulators (e.g., U.S. Pat. No. 6,566,372). This group of androgen receptor modulators was developed by using cell-based high-throughput assays, termed cotransfection assays.

SUMMARY OF THE INVENTION

The present invention is directed to compounds, pharmaceutical compositions, and methods for modulating processes mediated by androgen receptors. Certain compounds of the present invention may be represented as follows:

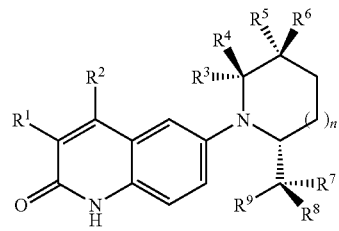

(I)

wherein:
$R^1$ is hydrogen, F, Cl, or $C_1$-$C_3$ alkyl;
$R^2$ is selected from the group of hydrogen, F, Cl, Br, $C_1$-$C_4$ alkyl, $C_1$-$C_4$ haloalkyl, and $C_1$-$C_4$ heteroalkyl;
$R^3$ and $R^4$ each independently is selected from the group of hydrogen, $C_1$-$C_4$ alkyl, $C_1$-$C_4$ haloalkyl, $C_1$-$C_4$ heteroalkyl, optionally substituted aryl and heteroaryl;
$R^5$ and $R^6$ each independently is selected from the group of hydrogen, F, Cl, $OR^{10}$, $C_1$-$C_4$ alkyl, $C_1$-$C_4$ haloalkyl, and $C_1$-$C_4$ heteroalkyl;
$R^7$ and $R^8$ each independently is selected from the group of hydrogen, F, Cl, $C_1$-$C_4$ alkyl, $C_1$-$C_4$ haloalkyl, and $C_1$-$C_4$ heteroalkyl; or
$R^7$ and $R^8$ taken together form a carbonyl group;
$R^9$ is selected from the group of halogen, $OR^{10}$, $SR^{10}$, $NR^{10}R^{11}$, $C_1$-$C_4$ haloalkyl, $C_1$-$C_4$ heteroalkyl, and $C_1$-$C_4$ heterohaloalkyl;
$R^{10}$ and $R^{11}$ each independently is selected from the group of hydrogen, $C_1$-$C_4$ alkyl, phenyl, and benzyl; and
n=0 or 1.

For a better understanding of the invention, its advantages, and objects obtained by its use, reference should be had to the accompanying descriptive matter, in which preferred embodiments of the invention are described.

DETAILED DESCRIPTION OF PREFERRED EMBODIMENTS

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

Definitions

Unless specific definitions are provided, the nomenclatures utilized in connection with, and the laboratory procedures and techniques of, analytical chemistry, synthetic organic chemistry, medicinal chemistry and pharmaceutical chemistry described herein are those known in the art. Standard chemical symbols are used interchangeably with the full names represented by such symbols. Thus, for example, the terms "hydrogen" and "H" are understood to have identical meaning. Standard techniques may be used for chemical syntheses, chemical analyses, pharmaceutical preparation, formulation, delivery, and treatment of patients. Standard techniques may be used for recombinant DNA methodology, oligonucleotide synthesis, tissue culture and transformation (e.g., electroporation, lipofection). Reactions and purification techniques may be performed e.g., using kits according to manufacturer's specifications, as commonly accomplished in the art or as described herein. The foregoing techniques and procedures may be generally performed according to conventional methods well known in the art and as described in various general or more specific references that are cited and discussed throughout the present specification. See e.g., Sambrook et al. *Molecular Cloning: A Laboratory Manual* (2d ed., Cold Spring Harbor Laboratory Press, Cold Spring Harbor, N.Y. (1989)), which is incorporated herein by reference for any purpose.

In the structural formulae depicted throughout the specification and claims, solid wedges and dashed wedges are used in their customary way to show stereochemistry. That is, a solid wedge is used to indicate that the attached substituent is in front of the plane of the paper, towards the reader. The dashed wedge is used to indicate that the attached substituent is behind the plane of the paper, away from the reader.

As used herein, the following terms are defined with the following meanings:

The term "selective binding compound" refers to a compound that selectively binds to any portion of one or more target receptors.

The term "selective androgen receptor binding compound" refers to a compound that selectively binds to any portion of an androgen receptor.

The term "selectively binds" refers to the ability of a selective binding compound to bind to a target receptor with greater affinity than it binds to a non-target receptor. In certain embodiments, selective binding refers to binding to a target with an affinity that is at least 10, 50, 100, 250, 500, or 1000 times greater than the affinity for a non-target.

The term "target receptor" refers to a receptor or a portion of a receptor capable of being bound by a selective binding compound. In certain embodiments, a target receptor is an androgen receptor.

The term "modulator" refers to a compound that alters or elicits an activity of a molecule. For example, a modulator may cause an increase or decrease in the magnitude of a certain activity of a molecule compared to the magnitude of the activity in the absence of the modulator. In certain embodiments, a modulator is an inhibitor, which decreases the magnitude of one or more activities of a molecule. In certain embodiments, an inhibitor completely prevents one or more activities of a molecule. In certain embodiments, a modulator is an activator, which increases the magnitude of at least one activity of a molecule. In certain embodiments the presence of a modulator results in an activity that does not occur in the absence of the modulator.

The term "selective modulator" refers to a compound that selectively modulates a target activity.

The term "selective androgen receptor modulator" refers to a compound that selectively modulates at least one activity associated with an androgen receptor.

The term "selectively modulates" refers to the ability of a selective modulator to modulate a target activity to a greater extent than it modulates a non-target activity.

The term "target activity" refers to a biological activity capable of being modulated by a selective modulator. Certain exemplary target activities include, but are not limited to, changes in binding affinity, signal transduction, enzymatic activity, transcription of one or more genes, tumor growth, changes in blood glucose concentration, and inflammation or inflammation-related processes.

The term "receptor-mediated activity" refers to any biological activity that results, either directly or indirectly, from binding of a ligand to a receptor.

The term "agonist" refers to a compound, the presence of which results in a biological activity of a receptor that is the same as the biological activity resulting from the presence of a naturally occurring ligand for the receptor.

The term "partial agonist" refers to a compound the presence of which results in a biological activity of a receptor that is of the same type as that resulting from the presence of a naturally occurring ligand for the receptor, but of a lower magnitude.

The term "antagonist" refers to a compound, the presence of which results in a decrease in the magnitude of a biological activity of a receptor. In certain embodiments, the presence of an antagonist results in complete inhibition of a biological activity of a receptor.

The term "aliphatic" refers to a straight or branched chain comprising at least one carbon atom. Aliphatics include alkyls, alkenyls, and alkynyls. In certain embodiments, aliphatics are optionally substituted. Aliphatics include, but are not limited to, methyl, ethyl, propyl, isopropyl, butyl, isobutyl, tertiary butyl, pentyl, hexyl, ethenyl, propenyl, butenyl, ethynyl, butynyl, propynyl, cyclopropyl, cyclobutyl, cyclopentyl, cyclohexyl, and the like, each of which may be optionally substituted. As used herein, aliphatic is not intended to include cyclic groups.

The term "alkyl," alone or in combination, refers to a fully saturated aliphatic. In certain embodiments, alkyls are optionally substituted. In certain embodiments, an alkyl comprises 1 to 20 carbon atoms (whenever it appears herein, a numerical range, such as "1 to 20" or "$C_1$-$C_{20}$", refers to each integer in the given range; e.g., "$C_1$-$C_{20}$ alkyl" means that an alkyl group may comprise only 1 carbon atom, 2 carbon atoms, 3 carbon atoms, etc., up to and including 20 carbon atoms, although the term "alkyl" also includes instances where no numerical range of carbon atoms is designated). Examples of alkyls include, but are not limited to, methyl, ethyl, n-propyl, isopropyl, n-butyl, isobutyl, sec-butyl, tert-butyl, tert-amyl, pentyl, hexyl, heptyl, octyl and the like.

The term "alkenyl," alone or in combination, refers to an aliphatic having one or more carbon-carbon double-bonds. In certain embodiments, alkenyls are optionally substituted. Examples of alkenyls include, but are not limited to, ethenyl, propenyl, 1,4-butadienyl and the like.

The term "alkynyl," alone or in combination, refers to an aliphatic having one or more carbon-carbon triple-bonds. In certain embodiments, alkynyls are optionally substituted. Examples of alkynyls include, but are not limited to, ethynyl, propynyl, butynyl and the like.

The term "haloaliphatic" refers to an aliphatic in which at least one hydrogen atom is replaced with a halogen atom. In certain embodiments in which two or more hydrogen atom are replaced with halogen atoms, the halogen atoms are all the same as each other. In certain of such embodiments, the halogen atoms are not all the same as each other. Haloaliphatics include haloalkyls, haloalkenyls, and haloalkynyls. In certain embodiments, haloaliphatics are optionally substituted, in addition to the halogen atom.

The term "heteroaliphatic" refers to a group comprising an aliphatic and one or more heteroatoms. Certain heteroaliphatics are acylaliphatics, in which the one or more heteroatoms is not within an aliphatic chain. Heteroaliphatics include heteroalkyls, including, but not limited to acylalkys; heteroalkenyls, including, but not limited to, acylalkenyls; and heteroalkynyls, including, but not limited acylalkynyls. Examples of heteroaliphatics include, but are not limited to, $CH_3C(=O)CH_2-$, $CH_3C(=O)CH_2CH_2-$, $CH_3CH_2C(=O)CH_2CH_2-$, $CH_3C(=O)CH_2CH_2CH_2-$, $CH_3OCH_2CH_2-$, $CH_3NHCH_2-$, and the like. In certain embodiments, heteroaliphatics are optionally substituted.

The term "heterohaloaliphatic" refers to a heteroaliphatic in which at least one hydrogen atom is replaced with a halogen atom. Heterohaloaliphatics include heterohaloalkyls, heterohaloalkenyls, and heterohaloalkynyls. In certain embodiments, heterohaloaliphatics are optionally substituted.

The term "carbocycle" refers to a group comprising a covalently closed ring, wherein each of the atoms forming the ring is a carbon atom. Carbocyclic rings may be formed by three, four, five, six, seven, eight, nine, or more than nine carbon atoms. In certain embodiments, carbocycles are optionally substituted.

The term "heterocycle" refers to a group comprising a covalently closed ring wherein at least one atom forming the ring is a heteroatom. Heterocyclic rings may be formed by three, four, five, six, seven, eight, nine, or more than nine atoms. Any number of those atoms may be heteroatoms (i.e., a heterocyclic ring may comprise one, two, three, four, five, six, seven, eight, nine, or more than nine heteroatoms). In heterocyclic rings comprising two or more heteroatoms, those two or more heteroatoms may be the same as or different from each other. Heterocycles may be optionally substituted. Binding to a heterocycle can be at a heteroatom or via a carbon atom. For example, binding for benzo-fused derivatives, may be via a carbon of the benzenoid ring. Examples of heterocycles include, but are not limited to the following:

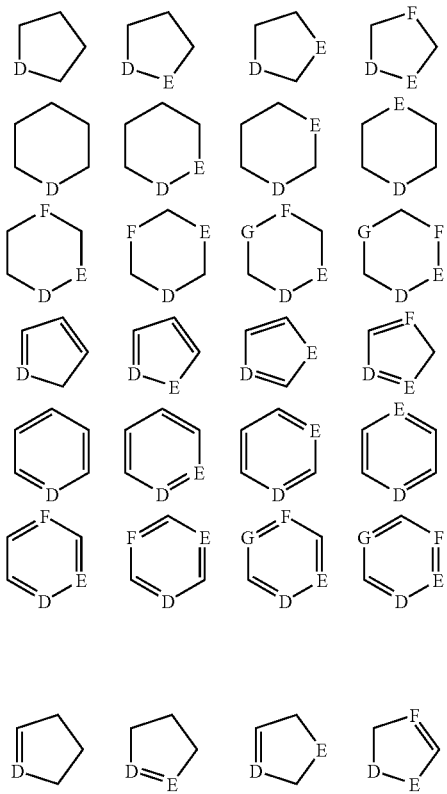

-continued

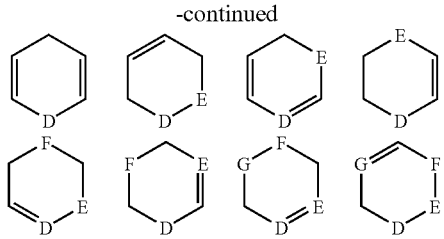

wherein D, E, F, and G each independently represent a heteroatom. Each of D, E, F, and G may be the same as or different from each other. In certain embodiments, heterocycles are optionally substituted.

The term "heteroatom" refers to an atom other than carbon or hydrogen. Heteroatoms are typically independently selected from oxygen, sulfur, nitrogen, and phosphorus, but are not limited to those atoms. In embodiments in which two or more heteroatoms are present, the two or more heteroatoms may all be the same, or some or all of the two or more heteroatoms may each be different from the others.

The term "aromatic" refers to a group comprising a covalently closed ring having a delocalized π-electron system. Aromatic rings may be formed by five, six, seven, eight, nine, or more than nine atoms. In certain embodiments, aromatics are optionally substituted. Examples of aromatic groups include, but are not limited to phenyl, naphthalenyl, phenanthrenyl, anthracenyl, tetralinyl, fluorenyl, indenyl, and indanyl. The term aromatic includes, for example, benzenoid groups, connected via one of the ring-forming carbon atoms, and optionally carrying one or more substituents selected from an aryl, a heteroaryl, a cycloalkyl, a non-aromatic heterocycle, a halo, a hydroxy, an amino, a cyano, a nitro, an alkylamido, an acyl, a $C_{1-6}$ alkoxy, a $C_{1-6}$ alkyl, a $C_{1-6}$ hydroxyalkyl, a $C_{1-6}$ aminoalkyl, a $C_{1-6}$ alkylamino, an alkylsulfenyl, an alkylsulfinyl, an alkylsulfonyl, an sulfamoyl, and a trifluoromethyl, In certain embodiments, an aromatic group is substituted at one or more of the para, meta, and/or ortho positions. Examples of aromatic groups comprising substitutions include, but are not limited to, phenyl, 3-halophenyl, 4-halophenyl, 3-hydroxyphenyl, 4-hydroxyphenyl, 3-aminophenyl, 4-aminophenyl, 3-methylphenyl, 4-methylphenyl, 3-methoxyphenyl, 4-methoxyphenyl, 4-trifluoromethoxyphenyl, 3-cyanophenyl, 4-cyanophenyl, dimethylphenyl, naphthyl, hydroxynaphthyl, hydroxymethylphenyl, (trifluoromethyl)phenyl, alkoxyphenyl, 4-morpholin-4-ylphenyl, 4-pyrrolidin-1-ylphenyl, 4-pyrazolylphenyl, 4-triazolylphenyl, and 4-(2-oxopyrrolidin-1-yl)phenyl.

The term "aryl" refers to an aromatic group wherein each of the atoms forming the ring is a carbon atom. Aryl rings may be formed by five, six, seven, eight, nine, or more than nine carbon atoms. In certain embodiments, aryls are optionally substituted.

The term "heteroaryl" refers to an aromatic group wherein at least one atom forming the aromatic ring is a heteroatom. Heteroaryl rings may be formed by three, four, five, six, seven, eight, nine, or more than nine atoms. In certain embodiments, heteroaryls are optionally substituted. Examples of heteroaryl groups include, but are not limited to, aromatic $C_{3-8}$ heterocyclic groups comprising one oxygen or sulfur atom or up to four nitrogen atoms, or a combination of one oxygen or sulfur atom and up to two nitrogen atoms, and their substituted as well as benzo- and pyrido-fused derivatives, for example, connected via one of the ring-forming carbon atoms. In certain embodiments, heteroaryl groups are optionally substituted with one or more substituents, independently selected from halo, hydroxy, amino, cyano, nitro, alkylamido, acyl, $C_{1-6}$ alkoxy, $C_{1-6}$ alkyl, $C_{1-6}$ hydroxyalkyl, $C_{1-6}$ aminoalkyl, $C_{1-6}$ alkylamino, alkylsulfenyl, alkylsulfinyl, alkylsulfonyl, sulfamoyl, and trifluoromethyl, Examples of heteroaryl groups include, but are not limited to, unsubstituted and mono- or di-substituted derivatives of furan, benzofuran, thiophene, benzothiophene, pyrrole, pyridine, indole, oxazole, benzoxazole, isoxazole, benzisoxazole, thiazole, benzothiazole, isothiazole, imidazole, benzimidazole, pyrazole, indazole, tetrazole, quinoline, isoquinoline, pyridazine, pyrimidine, purine and pyrazine, furazan, 1,2,3-oxadiazole, 1,2,3-thiadiazole, 1,2,4-thiadiazole, triazole, benzotriazole, pteridine, phenoxazole, oxadiazole, benzopyrazole, quinolizine, cinnoline, phthalazine, quinazoline, and quinoxaline. In some embodiments, the substituents are halo, hydroxy, cyano, O—$C_{1-6}$ alkyl, $C_{1-6}$ alkyl, hydroxy-$C_{1-6}$ alkyl, or amino-$C_{1-6}$ alkyl.

The term "non-aromatic ring" refers to a group comprising a covalently closed ring that does not have a delocalized π-electron system.

The term "alicyclic", alone or in combination, refers to a group comprising a non-aromatic ring wherein each of the atoms forming the ring is a carbon atom. Alicyclic rings may be formed by three, four, five, six, seven, eight, nine, or more than nine carbon atoms. In certain embodiments, alicyclics are optionally substituted. In certain embodiments, an alicyclic comprises one or more unsaturated bonds. Alicyclics include cycloalkyls, cycloalkenyls, and cycloalkynyls. Examples of alicyclics include, but are not limited to, cyclopropane, cyclobutane, cyclopentane, cyclopentene, cyclopentadiene, cyclohexane, cyclohexene, 1,3-cyclohexadiene, 1,4-cyclohexadiene, cycloheptane, and cycloheptene. In certain embodiments, alicylcic rings are optionally substituted.

The term "non-aromatic heterocycle" refers to a group comprising a non-aromatic ring wherein one or more atoms forming the ring is a heteroatom. Non-aromatic heterocyclic rings may be formed by three, four, five, six, seven, eight, nine, or more than nine atoms. In certain embodiments, non-aromatic heterocycles are optionally substituted. In certain embodiments, non-aromatic heterocycles comprise one or more carbonyl or thiocarbonyl groups such as, for example, oxo- and thio-containing groups. Examples of non-aromatic heterocycles include, but are not limited to, lactams, lactones, cyclic imides, cyclic thioimides, cyclic carbamates, tetrahydrothiopyran, 4H-pyran, tetrahydropyran, piperidine, 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, morpholine, trioxane, hexahydro-1,3,5-triazine, tetrahydrothiophene, tetrahydrofuran, pyrroline, pyrrolidine, pyrrolidone, pyrrolidione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, and 1,3-oxathiolane.

The term "arylalkyl" refers to a group comprising an aryl group bound to an alkyl group.

The term "ring" refers to any covalently closed structure. Rings include, for example, carbocycles (e.g., aryls and cycloalkyls), heterocycles (e.g., heteroaryls and non-aromatic heterocycles), aromatics (e.g., aryls and heteroaryls), and non-aromatics (e.g., alicyclics and non-aromatic heterocycles). In certain embodiments, rings are optionally substituted. Rings may form part of a ring system.

The term "ring system" refers to two or more rings, wherein two or more of the rings are fused. The term "fused" refers to structures in which two or more rings share one or more bonds.

The substituent "R" appearing by itself and without a number designation refers to a substituent selected from alkyl, alkenyl, alkynyl, cycloalkyl, cycloalkenyl, cycloalkynyl, aryl, heteroaryl (bonded through a ring carbon) and non-aromatic heterocycle (bonded through a ring carbon).

The term "null" refers to a group being absent from a structure. For example, in the structure

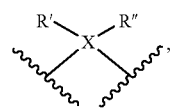

if X is C, then both R' and R" exist, but if X is N, then one of those R groups is null, meaning that only three groups are bound to the N.

The term "O-carboxy" refers to a group of formula RC(=O)O—.

The term "C-carboxy" refers to a group of formula —C(=O)OR.

The term "acetyl" refers to a group of formula —C(=O)CH$_3$.

The term "trihalomethanesulfonyl" refers to a group of formula X$_3$CS(=O)$_2$— where X is a halogen.

The term "cyano" refers to a group of formula —CN.

The term "isocyanato" refers to a group of formula —NCO.

The term "thiocyanato" refers to a group of formula —CNS.

The term "isothiocyanato" refers to a group of formula —NCS.

The term "sulfonyl" refers to a group of formula —S(=O)$_2$—R.

The term "S-sulfonamido" refers to a group of formula —S(=O)$_2$NR.

The term "N-sulfonamido" refers to a group of formula RS(=O)$_2$NH—.

The term "trihalomethanesulfonamido" refers to a group of formula X$_3$CS(=O)$_2$NR—.

The term "O-carbamyl" refers to a group of formula —OC(=O)—NR.

The term "N-carbamyl" refers to a group of formula ROC(=O)NH—.

The term "O-thiocarbamyl" refers to a group of formula —OC(=S)—NR.

The term "N-thiocarbamyl" refers to a group of formula ROC(=S)NH—.

The term "C-amido" refers to a group of formula —C(=O)—NR$_2$.

The term "N-amido" refers to a group of formula RC(=O)NH—.

The term "ester" refers to a chemical moiety with formula —(R)$_n$—COOR', where R and R' are independently selected from alkenyl, alkynyl, cycloalkyl, cycloalkenyl, cycloalkynyl, aryl, heteroaryl (bonded through a ring carbon) and non-aromatic heterocycle (bonded through a ring carbon), where n is 0 or 1.

The term "amide" refers to a chemical moiety with formula —(R)$_n$—C(O)NHR' or —(R)$_n$—NHC(O)R', where R and R' are independently selected from alkyl, alkenyl, alkynyl, cycloalkyl, cycloalkenyl, cycloalkynyl, aryl, heteroaryl (bonded through a ring carbon) and heteroalicyclic (bonded through a ring carbon), where n is 0 or 1. In certain embodiments, an amide may be an amino acid or a peptide.

The term "alkoxy," refers to an alkyl ether radical. Examples of alkoxy radicals include, but are not limited to, methoxy, ethoxy, n-propoxy, isopropoxy, n-butoxy, iso-butoxy, sec-butoxy, tert-butoxy and the like.

The term "formyl" includes aldehydes attached to a compound via an alkyl, aryl, heteroaryl, arylalkyl or heteroarylalkyl group (e.g., -alkyl-CHO, -aryl-CHO, -arylalkyl-CHO or -heteroarylalkyl-CHO, etc.).

The term "oxime" refers to a group of formula:

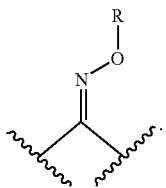

The term "hydrazone" refers to a group of formula:

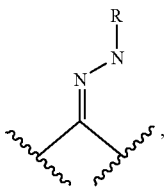

The term "hydroxylamine" refers to a group of formula:

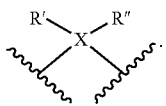

The term sulfonamide refers to a group of formula:

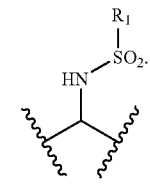

The term "halogen" includes, but is not limited to, F, Cl, Br, and I

The terms "amine," "hydroxy," and "carboxyl" include such groups that have been esterified or amidified. Procedures and specific groups used to achieve esterification and amidification are known to those of skill in the art and can readily be found in reference sources such as Greene and Wuts, *Protective Groups in Organic Synthesis,* 3rd Ed., John Wiley & Sons, New York, N.Y., 1999, which is incorporated by reference herein in its entirety.

Unless otherwise indicated, the term "optionally substituted," refers to a group in which none, one, or more than one of the hydrogen atoms has been replaced with one or more group(s) individually and independently selected from: alkyl, alkenyl, alkynyl, heteroalkyl, heteroalkenyl, heteroalkynyl, haloalkyl, haloalkenyl, haloalkynyl, heterohaloalkyl, cycloalkyl, cycloalkenyl, cycloalkynyl, aryl, arylalkyl, arylalkenyl, arylalkynyl, arylalkyl, heteroaryl, non-aromatic heterocycle, hydroxy, alkoxy, aryloxy, mercapto, alkylthio, alkenylthio, alkynylthio, arylthio, cyano, halo, carbonyl, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, isothiocyanato, nitro, silyl, trihalomethanesulfonyl, and amino, including mono- and di-substituted amino groups, and the protected derivatives of amino groups. Such protective derivatives (and protecting groups that may form such protective derivatives) are known to those of skill in the art and may be found in references such as Greene and Wuts, supra. In embodiments in which two or more hydrogen atoms have been substituted, the substituent groups may together form a ring.

The term "carrier" refers to a compound that facilitates the incorporation of another compound into cells or tissues. For example, dimethyl sulfoxide (DMSO) is a commonly used carrier for improving incorporation of certain organic compounds into cells or tissues.

The term "pharmaceutical agent" refers to a chemical compound or composition capable of inducing a desired therapeutic effect in a patient. In certain embodiments, a pharmaceutical agent comprises an active agent, which is the agent that induces the desired therapeutic effect. In certain embodiments, a pharmaceutical agent comprises a prodrug. In certain embodiments, a pharmaceutical agent comprises inactive ingredients such as carriers, excipients, and the like.

The term "pharmaceutical composition" refers to a preparation suitable for pharmaceutical application. Pharmaceutical compositions of the invention typically comprise one or more compounds of the present invention together with at least one pharmaceutically acceptable carrier, diluent or excipient or the like.

The term "therapeutically effective amount" refers to an amount of a pharmaceutical agent sufficient to achieve a desired therapeutic effect.

The term "prodrug" refers to a pharmaceutical agent that is converted from a less active form into a corresponding more active form in vivo.

The term "pharmaceutically acceptable" refers to a formulation of a compound that does not significantly abrogate a biological activity, a pharmacological activity and/or other properties of the compound when the formulated compound is administered to a patient. In certain embodiments, a pharmaceutically acceptable formulation does not cause significant irritation to a patient.

The term "co-administer" refers to administering more than one pharmaceutical agent to a patient. In certain embodiments, co-administered pharmaceutical agents are administered together in a single dosage unit. In certain embodiments, co-administered pharmaceutical agents are administered separately. In certain embodiments, co-administered pharmaceutical agents are administered at the same time. In certain embodiments, co-administered pharmaceutical agents are administered at different times.

The term "patient" includes human and animal subjects.

The term "substantially pure" means an object species (e.g., compound) is the predominant species present (i.e., on a molar basis it is more abundant than any other individual species in the composition). In certain embodiments, a substantially pure refers to a composition wherein the object species comprises at least about 50 percent (on a molar basis)

of all species present. In certain embodiments, a substantially pure composition is a composition wherein the object species comprises more than about 80%, 85%, 90%, 95%, or 99% of all species present in the composition. In certain embodiments, a substantially pure object species is purified to essential homogeneity (contaminant species cannot be detected in the composition by conventional detection methods) wherein the composition consists essentially of the single object species.

The term "tissue-selective" refers to the ability of a compound to modulate a biological activity in one tissue to a greater or lesser degree than it modulates a biological activity in another tissue. The biological activities modulated in the different tissues may be the same or they may be different. The biological activities modulated in the different tissues may be mediated by the same type of target receptor. For example, in certain embodiments, a tissue-selective compound may modulate an androgen receptor-mediated biological activity in one tissue and fail to modulate, or modulate to a lesser degree, an androgen receptor-mediated biological activity in another tissue type.

The term "monitoring" refers to observing an effect or absence of any effect. In certain embodiments, cells are monitored after contacting those cells with a compound of the present invention. Examples of effects that may be monitored include, but are not limited to, changes in cell phenotype, cell proliferation, an androgen receptor activity, or the interaction between an androgen receptor and a natural or synthetic binding partner.

The term "cell phenotype" refers to physical or biological characteristics of a cell. Examples of characteristics that constitute phenotype included, but are not limited to, cell size, cell proliferation, cell differentiation, cell survival, apoptosis (cell death), or the utilization of a metabolic nutrient (e.g., glucose uptake). Certain changes or the absence of changes in cell phenotype are readily monitored using techniques known in the art.

The term "cell proliferation" refers to the rate at which cells divide. The number of cells growing in a vessel can be quantified by a person skilled in the art (e.g., by counting cells in a defined area using a light microscope, or by using laboratory apparatus that measure the density of cells in an appropriate medium). One skilled in that art can calculate cell proliferation by determining the number of cells in a sample at two or more times.

The term "contacting" refers to bringing two or more materials into close enough proximity that they may interact. In certain embodiments, contacting can be accomplished in a vessel such as a test tube, a petri dish, or the like. In certain embodiments, contacting may be performed in the presence of additional materials. In certain embodiments, contacting may be performed in the presence of cells. In certain of such embodiments, one or more of the materials that are being contacted may be inside a cell. Cells may be alive or may be dead. Cells may or may not be intact.

Certain Compounds

Certain compounds that bind to androgen receptors and/or modulate an activity of such receptors play a role in health (e.g., normal growth, development, and/or absence of disease). In certain embodiments, selective androgen receptor modulators and/or binding compounds are useful for treating any of a variety of diseases or conditions.

Certain compounds have been previously described as receptor modulators or as possible receptor modulators. See e.g., U.S. Pat. Nos. 6,462,038, 5,693,646; 6,380,207; 6,506,766; 5,688,810; 5,696,133; 6,569,896, 6,673,799; 4,636,505; 4,097,578; 3,847,988; U.S. application Ser. No. 10/209,461 (Pub. No. US 2003/0055094); International Patent Application Nos. WO 01/27086 and WO 02/22585; Zhi, et al. *Bioorganic & Medicinal Chemistry Letters* 2000, 10, 415-418; Pooley, et al., *J. Med. Chem.* 1998, 41, 3461; Hamann, et al. *J. Med. Chem.* 1998, 41(4), 623; and Yin, et al., *Molecular Pharmacology*, 2003, 63 (1), 211-223 the entire disclosures of which are incorporated by reference herein in their entirety.

In certain embodiments, the present invention provides selective androgen receptor modulators. In certain embodiments, the invention provides selective androgen receptor binding agents. In certain embodiments, the invention provides methods of making and methods of using selective androgen receptor modulators and/or selective androgen binding agents. In certain embodiments, selective androgen modulators are agonists, partial agonists, and/or antagonists for the androgen receptor.

Certain compounds of the present invention may be represented by the formula:

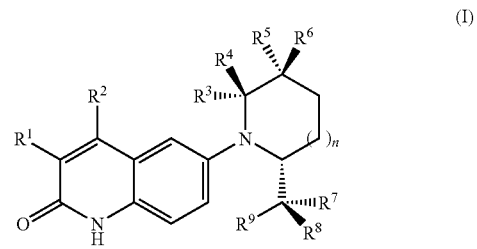

(I)

or a pharmaceutically acceptable salt, ester, amide, or prodrug thereof.

In certain embodiments, $R^1$ is selected from hydrogen, F, Cl, and $C_1$-$C_3$ aliphatic. In certain of such embodiments, $R^1$ is selected from $C_1$-$C_3$ alkyl.

In certain embodiments, $R^2$ is selected from hydrogen, F, Cl, Br, $C_1$-$C_4$ aliphatic, $C_1$-$C_4$ haloaliphatic, and $C_1$-$C_4$ heteroaliphatic. In certain of such embodiments, R2 is selected from $C_1$-$C_4$ alkyl, $C_1$-$C_4$ haloalkyl, and $C_1$-$C_4$ heteroalkyl.

In certain embodiments, $R^3$ and $R^4$ are each independently selected from hydrogen, $C_1$-$C_4$ aliphatic, $C_1$-$C_4$ haloaliphatic, $C_1$-$C_4$ heteroaliphatic, optionally substituted aryl and heteroaryl. In certain of such embodiments, $R^3$ and $R^4$ are each independently selected from $C_1$-$C_4$ alkyl, $C_1$-$C_4$ haloalkyl, and $C_1$-$C_4$ heteroalkyl.

In certain embodiments, $R^5$ and $R^6$ are each independently selected from hydrogen, F, Cl, $OR^{10}$, $C_1$-$C_4$ aliphatic, $C_1$-$C_4$ haloaliphatic, $C_1$-$C_4$ heteroaliphatic. In certain of such embodiments, $R^5$ and $R^6$ are each independently selected from $C_1$-$C_4$ alkyl, $C_1$-$C_4$ haloalkyl, and $C_1$-$C_4$ heteroalkyl.

In certain embodiments, $R^7$ and $R^8$ are each independently selected from hydrogen, F, Cl, $C_1$-$C_4$ aliphatic, $C_1$-$C_4$ haloaliphatic, $C_1$-$C_4$ heteroaliphatic. In certain of such embodiments, $R^7$ and $R^8$ are each independently selected from $C_1$-$C_4$ alkyl, $C_1$-$C_4$ haloalkyl, and $C_1$-$C_4$ heteroalkyl. In certain embodiments, $R^7$ and $R^8$ taken together form a carbonyl group.

In certain embodiments, $R^9$ is selected from halogen, $OR^{10}$, $SR^{10}$, $NR^{10}R^{11}$, $C_1$-$C_4$ haloaliphatic, $C_1$-$C_4$ heteroaliphatic, and $C_1$-$C_4$ heterohaloaliphatic. In certain embodiments, $R^9$ is haloalkyl. In certain embodiments $R^9$ is $C_1$-$C_4$ heteroalkyl. In certain embodiments $R^9$ is $C_1$-$C_4$ heterohaloalkyl.

In certain embodiments, $R^{10}$ and $R^{11}$ are each independently selected from hydrogen, $C_1$-$C_4$ aliphatic, phenyl, and benzyl. In certain embodiments, $R^{10}$ and $R^{11}$ are each independently selected from $C_1$-$C_4$ alkyl.

In certain embodiments, n is 0 or 1.

In embodiments in which two or more of a particular variable are present, the identities of those two or more particular variables are selected independently and, thus, may be the same or different from each other. For example, certain compounds of the invention comprise two or more $R^{10}$ groups. The identities of those two or more $R^{10}$ groups are each selected independently. Thus, in certain embodiments, those $R^{10}$ groups are all the same as each other; in certain embodiments, those $R^{10}$ groups are all different from each other; and in certain embodiments, some of those $R^{10}$ groups are the same as at least one other $R^{10}$ group and some are different from at least one other $R^{10}$ group.

Certain compounds of the present inventions may exist as stereoisomers including optical isomers. The present disclosure is intended to include all stereoisomers and both the racemic mixtures of such stereoisomers as well as the individual enantiomers that may be separated according to methods that are known in the art.

In certain embodiments, a compound of Formula I is a selective androgen receptor modulator. In certain embodiments, a compound of Formula I is a selective androgen receptor agonist. In certain embodiments, a compound of Formula I is a selective androgen receptor antagonist. In certain embodiments, a compound of Formula I is a selective androgen receptor partial agonist. In certain embodiments, a compound of Formula I is a tissue-specific selective androgen modulator. In certain embodiments, a compound of Formula I is a gene-specific selective androgen modulator. In certain embodiments, a compound of Formula I is a selective androgen receptor binding compound. In certain embodiments, a compound of Formula I is a selective androgen receptor modulator that also modulates one or more other nuclear receptor.

Representative androgen receptor modulator compounds according to the present invention include, for example:

(R)-6-(2-(2,2,2-Trifluoroethyl)-1-pyrrolidinyl)-4-trifluoromethyl-2(1H)-quinolinone (Compound 101);

(R)-6-(2-Phenylthiomethyl-1-pyrrolidinyl)-4-trifluoromethyl-2(1H)-quinolinone (Compound 102);

(R)-6-(2-(2,2,2-Trifluoroethyl)-1-piperidinyl)-4-trifluoromethyl-2(1H)-quinolinone (Compound 103);

(R)-6-(2-Benzyloxymethyl)-1-piperidinyl)-4-trifluoromethyl-2(1H)-quinolinone (Compound 104);

(R)-6-(2-Diethylaminomethyl-1-pyrrolidinyl)-4-trifluoromethyl-2(1H)-quinolinone (Compound 105);

6-(2(R)-Hydroxymethyl-5(S)-methyl-1-pyrrolidinyl)-4-trifluoromethyl-2(1H)-quinolinone (Compound 106);

6-(2(R)-Fluoromethyl-5(R)-methyl-1-pyrrolidinyl)-4-trifluoromethyl-2(1H)-quinolinone (Compound 107);

6-(2(R)-Fluoromethyl-5(S)-methyl-1-pyrrolidinyl)-4-trifluoromethyl-2(1H)-quinolinone (Compound 108);

6-(2(R)-Difluoromethyl-5(R)-methyl-1-pyrrolidinyl)-4-trifluoromethyl-2(1H)-quinolinone (Compound 109);

6-(2(R)-Fluoromethyl-5(S)-methyl-1-pyrrolidinyl)-4-trifluoromethyl-2(1H)-quinolinone (Compound 110);

6-(2(R)-(1(R)-Hydroxy-2,2,2-trifluoroethyl)-5(S)-methyl-1-pyrrolidinyl)-4-trifluoromethyl-2(1H)-quinolinone (Compound 111);

6-(2(R)-(1(S)-Hydroxy-2,2,2-trifluoroethyl)-5(S)-methyl-1-pyrrolidinyl)-4-trifluoromethyl-2(1H)-quinolinone (Compound 112);

6-(2(R)-(1(S)-Hydroxy-2,2,2-trifluoroethyl)-5(R)-methyl-1-pyrrolidinyl)-4-trifluoromethyl-2(1H)-quinolinone (Compound 113);

6-(2(R)-(1 (R)-Hydroxy-2,2,2-trifluoroethyl)-5(R)-methyl-1-pyrolidinyl)-4-trifluoromethyl-2(1H)-quinolinone (Compound 114);

6-(2(R)-(2,2,2-Trifluoroethyl)-5(R)-methyl-1-pyrrolidinyl)-4-trifluoromethyl-2(1H)-quinolinone (Compound 115);

6-(2(R)-(1(S)-Hydroxy-2,2,2-trifluoroethyl)-4(R)-hydroxy-1-pyrrolidinyl)-4-trifluoromethyl-2(1H)-quinolinone (Compound 116);

6-(2(R)-(1(R)-Hydroxy-2,2,2-trifluoroethyl)-4(R)-hydroxy-1-pyrrolidinyl)-4-trifluoromethyl-2(1H)-quinolinone (Compound 117);

6-(2(R)-(1(S)-Fluoro-2,2,2-trifluoroethyl)-4(S)-fluoro-1-pyrrolidinyl)-4-trifluoromethyl-2(1H)-quinolinone (Compound 118);

6-(2(R)-(1(R)-Fluoro-2,2,2-trifluoroethyl)-4(S)-fluoro-1-pyrrolidinyl)-4-trifluoromethyl-2(1H)-quinolinone (Compound 119);

6-(2(R)-(1(S)-Hydroxy-2,2,2-trifluoroethyl)-4(R)-methyl-1-pyrrolidinyl)-4-trifluoromethyl-2(1H)-quinolinone (Compound 120);

6-(2(R)-(1(R)-Hydroxy-2,2,2-trifluoroethyl)-4(R)-methyl-1-pyrrolidinyl)-4-trifluoromethyl-2(1H)-quinolinone (Compound 121);

6-(2(R)-(1(S)-Hydroxy-2,2,2-trifluoroethyl)-4(S)-methyl-1-pyrrolidinyl)-4-trifluoromethyl-2(1H)-quinolinone (Compound 122);

6-(2(R)-1(R)-Hydroxy-2,2,2-trifluoroethyl)-4(S)-methyl-1-pyrrolidinyl)-4-trifluoromethyl-2(1H)-quinolinone (Compound 123);

6-(2(R)-(1(S)-Hydroxy-2,2,2-trifluoroethyl)-4(R)-methoxy-1-pyrrolidinyl)-4-trifluoromethyl-2(1H)-quinolinone (Compound 124);

6-(2(R)-(1(R)-Hydroxy-2,2,2-trifluoroethyl)-4(R)-methoxy-1-pyrrolidinyl)-4-trifluoromethyl-2(1H)-quinolinone (Compound 125);

6-(2(R)-(1 (R)-Hydroxy-2,2,2-trifluoroethyl)-4(S)-methoxy-1-pyrrolidinyl)-4-trifluoromethyl-2(1H)-quinolinone (Compound 126);

6-(2(R)-(1(S)-Hydroxy-2,2,2-trifluoroethyl)-4(S)-methoxy-1-pyrrolidinyl)-4-trifluoromethyl-2(1H)-quinolinone (Compound 127);

4-Chloro-6-(2(R)-(1(S)-hydroxy-2,2,2-trifluoroethyl)-5(R)-methyl-1-pyrrolidinyl)-2(1H)-quinolinone (Compound 128);

4-Chloro-6-(2(R)-(1 (R)-hydroxy-2,2,2-trifluoroethyl)-5(R)-methyl-1-pyrrolidinyl)-2(1H)-quinolinone (Compound 129);

4-Chloro-6-(2(R)-(1(S)-hydroxy-2,2,2-trifluoroethyl)-1-pyrrolidinyl)-2(1H)-quinolinone (Compound 130);

4-Chloro-6-(2(R)-(1 (R)-hydroxy-2,2,2-trifluoroethyl)-1-pyrrolidinyl)-2(1H)-quinolinone (Compound 131);

6-(2(R)-(1 (R)-Hydroxy-1-methyl-2,2,2-trifluoroethyl)-5(R)-methyl-1-pyrrolidinyl)-4-trifluoromethyl-2(1H)-quinolinone (Compound 132);

6-(2(R)-(1(S)-Hydroxy-1-methyl-2,2,2-trifluoroethyl)-5(R)-methyl-1-pyrrolidinyl)-4-trifluoromethyl-2(1H)-quinolinone (Compound 133);

6-(2(R)-(1-Hydroxy-1-trifluoromethyl-2,2,2-trifluoroethyl)-5(R)-methyl-1-pyrrolidinyl)-4-trifluoromethyl-2(1H)-quinolinone (Compound 134);

6-(2(R)-(1 (R)-Ethoxy-2,2,2-trifluoroethyl)-1-pyrrolidinyl)-4-trifluoromethyl-2(1H)-quinolinone (Compound 135);

6-(2(R)-(1 (R)-Hydroxy-2,2,2-trifluoroethyl)-1-pyrrolidinyl)-4-propyl-2(1H)-quinolinone (Compound 136);

6-(2(R)-(1(S)-Hydroxy-2,2,2-trifluoroethyl)-1-pyrrolidinyl)-4-propyl-2(1H)-quinolinone (Compound 137);

6-(2(R)-(1(S)-Hydroxy-2,2,2-trifluoroethyl)-1-pyrrolidinyl)-4-ethyl-2(1H)-quinolinone (Compound 138);
6-(2(R)-(1(R)-Hydroxy-2,2,2-trifluoroethyl)-1-pyrrolidinyl)-4-ethyl-2(1H)-quinolinone (Compound 139);
6-(2(R)-Chloromethyl-5-(R)-methyl-1-pyrrolidinyl)-4-trifluoromethyl-2(1H)-quinolinone (Compound 140);
6-(2(R)-Chloromethyl-5-(S)-methyl-1-pyrrolidinyl)-4-trifluoromethyl-2(1H)-quinolinone (Compound 141);
6-(2(R)-(1(S)-Hydroxy-2,2,2-trifluoroethyl)-5(S)-phenyl-1-pyrrolidinyl)-4-trifluoromethyl-2(1H)-quinolinone (Compound 142);
6-(2(R)-(1(R)-Hydroxy-2,2,2-trifluoroethyl)-5(S)-phenyl-1-pyrrolidinyl)-4-trifluoromethyl-2(1H)-quinolinone (Compound 143);
6-(2(R)-(1(S)-Hydroxy-2,2,2-trifluoroethyl)-5,5-dimethyl-1-pyrrolidinyl)-4-trifluoromethyl-2(1H)-quinolinone (Compound 144);
6-(2(R)-(1(R)-Hydroxy-2,2,2-trifluoroethyl)-5,5-dimethyl-1-pyrrolidinyl)-4-trifluoromethyl-2(1H)-quinolinone (Compound 145);
6-(2(R)-(1(S)-Hydroxy-2,2,2-trifluoroethyl)-5(R)-phenyl-1-pyrrolidinyl)-4-trifluoromethyl-2(1H)-quinolinone (Compound 146);
6-(2(R)-(1 (R)-Hydroxy-2,2,2-trifluoroethyl)-5(R)-phenyl-1-pyrrolidinyl)-4-trifluoromethyl-2(1H)-quinolinone (Compound 147);
6-(2(R)-(1(R),2-Dihydroxyethyl)-1-pyrrolidinyl)-4-trifluoromethyl-2(1H)-quinolinone (Compound 148);
6-(2(R)-(1(S),2-dihydroxyethyl)-1-pyrrolidinyl)-4-trifluoromethyl-2(1H)-quinolinone (Compound 149);
6-(2(R)-(1(R)-Hydroxybenzyl)-5(S)-methyl-1-pyrrolidinyl)-4-trifluoromethyl-2(1H)-quinolinone (Compound 150);
6-(2(R)-(1(S)-Hydroxybenzyl)-5(R)-methyl-1-pyrrolidinyl)-4-trifluoromethyl-2(1H)-quinolinone (Compound 151);
6-(2(R)-(1(R)-Hydroxybenzyl)-5(R)-methyl-1-pyrrolidinyl)-4-trifluoromethyl-2(1H)-quinolinone (Compound 152);
6-(2(R)-((2-1,3-Dithianyl)-1 (R)-hydroxymethyl)-5(R)-methyl-1-pyrrolidinyl)-4-trifluoromethyl-2(1H)-quinolinone (Compound 153);
6-(2(R)-((2-1,3-Dithianyl)-1(S)-hydroxymethyl)-5(R)-methyl-1-pyrrolidinyl)-4-trifluoromethyl-2(1H)-quinolinone (Compound 154);
6-(2(R)-Difluoromethyl-5,5-dimethyl-1-pyrrolidinyl)-4-trifluoromethyl-2(1H)-quinolinone (Compound 155);
6-(2(R)-Fluoromethyl-5,5-dimethyl-1-pyrrolidinyl)-4-trifluoromethyl-2(1H)-quinolinone (Compound 156);
6-(2(R)-Hydroxymethyl-5,5-dimethyl-1-pyrrolidinyl)-4-trifluoromethyl-2(1H)-quinolinone (Compound 157);
6-(2(R)-Hydroxymethyl-1-piperidinyl)-4-trifluoromethyl-2(1H)-quinolinone (Compound 158);
6-(2(R)-(1(S)-Hydroxyethyl-1-piperidinyl)-4-trifluoromethyl-2(1H)-quinolinone (Compound 159);
6-(2(R)-(1 (R)-Hydroxyethyl-1-piperidinyl)-4-trifluoromethyl-2(1H)-quinolinone (Compound 160);
6-(2(R)-Trifluoroacetyl-1-piperidinyl)-4-trifluoromethyl-2(1H)-quinolinone (Compound 161);
6-(2(R)-(1(S)-Hydroxypentyl-1-piperidinyl)-4-trifluoromethyl-2(1H)-quinolinone (Compound 162);
6-(2(R)-(1(R)-Hydroxypentyl-1-piperidinyl)-4-trifluoromethyl-2(1H)-quinolinone (Compound 163);
6-(2(R)-(1(R)-Hydroxyethyl)-5(R)-methyl-1-pyrrolidinyl)-4-trifluoromethyl-2(1H)-quinolinone (Compound 164);
6-(2(R)-(1-Hydroxy-1-methylethyl)-5(R)-methyl-1-pyrrolidinyl)-4-trifluoromethyl-2(1H)-quinolinone (Compound 165);
6-(2(R)-(1(S)-Hydroxy-1-cyclopropylmethyl)-5(R)-methyl-1-pyrrolidinyl)-4-trifluoromethyl-2(1H)-quinolinone (Compound 166);
6-(2(R)-(1(R)-Hydroxy-1-cyclopropylmethyl)-5(R)-methyl-1-pyrrolidinyl)-4-trifluoromethyl-2(1H)-quinolinone (Compound 167);
6-(2(R)-(1(S)-Hydroxypropyl)-5(R)-methyl-1-pyrrolidinyl)-4-trifluoromethyl-2(1H)-quinolinone (Compound 168);
6-(2(R)-(1(R)-Hydroxypropyl)-5(S)-methyl-1-pyrrolidinyl)-4-trifluoromethyl-2(1H)-quinolinone (Compound 169);
6-(2(R)-(1(R)-Hydroxypropyl)-5(R)-methyl-1-pyrrolidinyl)-4-trifluoromethyl-2(1H)-quinolinone (Compound 170);
6-(2(R)-(1(S)-Hydroxypropyl)-5(S)-methyl-1-pyrrolidinyl)-4-trifluoromethyl-2(1H)-quinolinone (Compound 171);
6-(2(R)-(1(R)-Hydroxy-2-methylpropyl)-5(R)-methyl-1-pyrrolidinyl)-4-trifluoromethyl-2(1H)-quinolinone (Compound 172);
6-(2(R)-(1 (R)-Hydroxy-2-acetoxyethyl)-1-pyrrolidinyl)-4-trifluoromethyl-2(1H)-quinolinone (Compound 173);
6-(2(R)-(1(R)-Hydroxy-2-chloroethyl)-1-pyrrolidinyl)-4-trifluoromethyl-2(1H)-quinolinone (Compound 174);
6-(2(R)-(2-Hydroxyethyl)-1-pyrrolidinyl)-4-trifluoromethyl-2(1H)-quinolinone (Compound 175);
6-(2(R)-(2-Oxoethyl)-1-pyrrolidinyl)-4-trifluoromethyl-2(1H)-quinolinone (Compound 176);
6-(2(R)-Acetyloxymethyl-6(R)-methyl-1-piperidinyl)-4-trifluoromethyl-2(1H)-quinolinone (Compound 177);
6-(2(R)-(1(R)-Chloro-2-hydroxyethyl)-1-pyrrolidinyl)-4-trifluoromethyl-2(1H)-quinolinone (Compound 178);
6-(2(R)-Hydroxymethyl-6(R)-methyl-1-piperidinyl)-4-trifluoromethyl-2(1H)-quinolinone (Compound 179);
6-(2(R)-(1 (R)-Hydroxy-2,2,2-trifluoroethyl)-6(R)-methyl-1-piperidinyl)-4-trifluoromethyl-2(1H)-quinolinone (Compound 180);
6-(2(R)-(1(S)-Hydroxy-2,2,2-trifluoroethyl)-5(R)-methyl-1-pyrrolidinyl)-4-chlorodifluoromethyl-2(1H)-quinolinone (Compound 181);
6-(2(R)-(1 (R)-Hydroxy-2,2,2-trifluoroethyl)-5(R)-methyl-1-pyrrolidinyl)-4-chlorodifluoromethyl-2(1H)-quinolinone (Compound 182);
6-(2(R)-(1(S)-Hydroxy-2,2,2-trifluoroethyl)-5(S)-methyl-1-pyrrolidinyl)-4-chlorodifluoromethyl-2(1H)-quinolinone (Compound 183);
6-(2(R)-(2(S)-Hydroxy-3,3,3-trifluoropropyl)-1-pyrrolidinyl)-4-trifluoromethyl-2(1H)-quinolinone (Compound 184);
6-(2(R)-(2(R)-hydroxy-3,3,3-trifluoropropyl)-1-pyrrolidinyl)-4-trifluoromethyl-2(1H)-quinolinone (Compound 185),
6-(2(R)-Acetyloxymethyl-6(R)-methyl-1-piperidinyl)-4-trifluoromethyl-2(1H)-quinolinone (Compound 186);
6-(2(R)-(2-Hydroxyethyl)-5(R)-methyl-1-pyrrolidinyl)-4-trifluoromethyl-2(1H)-quinolinone (Compound 187);
6-(2(R)-(2-Hydroxyethyl)-5(S)-methyl-1-pyrrolidinyl)-4-trifluoromethyl-2(1H)-quinolinone (Compound 188);
6-(2(R)-Acetyloxyethyl-5(R)-methyl-1-pyrrolidinyl)-4-trifluoromethyl-2(1H)-quinolinone (Compound 189);

6-(2(R)-(1(S)-Hydroxy-2,2,2-trifluoroethyl)-4(S)-fluoro-1-pyrrolidinyl)-4-trifluoromethyl-2(1H)-quinolinone (Compound 190);
6-(2(R)-(1 (R)-Hydroxy-2,2,2-trifluoroethyl)-4(S)-fluoro-1-pyrrolidinyl)-4-trifluoromethyl-2(1H)-quinolinone (Compound 191);

and pharmaceutically acceptable salts, esters, amides, and/or prodrugs of any of those compounds.

The following table provides examples of certain variables from various Markush groups in this application. One of ordinary skill in the art will recognize that the variables and groups of variables may selected in any combination. One of ordinary skill in the art will also recognize that this table is merely illustrative of certain combinations and does not limit the invention in any way.

| | Markush Group A | Markush Group B | Markush Group C | Markush Group D |
|---|---|---|---|---|
| $R^1$ | hydrogen, F, Cl and $C_1$-$C_3$ aliphatic | hydrogen and $C_1$-$C_2$ alkyl | F and Cl | hydrogen |
| $R^2$ | hydrogen, F, Cl, Br, $C_1$-$C_4$ aliphatic, $C_1$-$C_4$ haloaliphatic and $C_1$-$C_4$ heteroaliphatic | hydrogen, , $C_1$-$C_2$ alkyl, $C_1$-$C_2$ haloalkyl, and $C_1$-$C_2$ heteroalkyl | F, Cl and Br | hydrogen |
| $R^3$ | hydrogen, $C_1$-$C_4$ aliphatic, $C_1$-$C_4$ haloaliphatic, $C_1$-$C_4$ heteroaliphatic, optionally substituted aryl, optionally substituted heteroaryl | hydrogen, $C_1$-$C_2$ alkyl, $C_1$-$C_2$ haloalkyl, and $C_1$-$C_2$ heteroalkyl | optionally substituted aryl and heteroaryl | hydrogen |
| $R^4$ | hydrogen, $C_1$-$C_4$ aliphatic, $C_1$-$C_4$ haloaliphatic, $C_1$-$C_4$ heteroaliphatic, optionally substituted aryl, optionally substituted heteroaryl | hydrogen, $C_1$-$C_2$ alkyl, $C_1$-$C_2$ haloalkyl, and $C_1$-$C_2$ heteroalkyl | optionally substituted aryl and heteroaryl | hydrogen |
| $R^5$ | hydrogen, F, Cl, $OR^{10}$, $C_1$-$C_4$ aliphatic, $C_1$-$C_4$ haloaliphatic and $C_1$-$C_4$ heteroaliphatic | hydrogen, $OR^{10}$, $C_1$-$C_2$ alkyl, $C_1$-$C_2$, $C_1$-$C_2$ haloalkyl and $C_1$-$C_2$ heteroalkyl | F and Cl | hydrogen |
| $R^6$ | hydrogen, F, Cl, $OR^{10}$, $C_1$-$C_4$ aliphatic, $C_1$-$C_4$ haloaliphatic and $C_1$-$C_4$ heteroaliphatic | hydrogen, $OR^{10}$, $C_1$-$C_2$ alkyl, $C_1$-$C_2$, $C_1$-$C_2$ haloalkyl and $C_1$-$C_2$ heteroalkyl | F and Cl | hydrogen |
| $R^7$ | hydrogen, F, Cl, $C_1$-$C_4$ aliphatic, $C_1$-$C_4$ haloaliphatic and $C_1$-$C_4$ heteroaliphatic or $R_7$ and $R_8$ taken together form a carbonyl group | hydrogen, $C_1$-$C_2$ alkyl, $C_1$-$C_2$ haloalkyl and $C_1$-$C_2$ heteroalkyl | F and Cl | hydrogen |
| $R^8$ | hydrogen, F, Cl, $C_1$-$C_4$ aliphatic, $C_1$-$C_4$ haloaliphatic and $C_1$-$C_4$ heteroaliphatic or $R_7$ and $R_8$ taken together form a carbonyl group | hydrogen, $C_1$-$C_2$ alkyl, $C_1$-$C_2$ haloalkyl and $C_1$-$C_2$ heteroalkyl | F and Cl | hydrogen |
| $R^9$ | halogen, $OR^{10}$, $SR^{10}$, $NR^{10}R^{11}$, $C_1$-$C_4$ heteroaliphatic $C_1$-$C_4$, haloaliphatic and $C_1$-$C_4$ heterohaloaliphatic | $OR^{10}$, $SR^{10}$, $NR^{10}R^{11}$ and $C_1$-$C_2$, haloalkyl | $OR^{10}$ and $SR^{10}$, | halogen |
| $R^{10}$ | halogen, $C_1$-$C_4$ aliphatic, phenyl and benzyl, | hydrogen and $C_1$-$C_2$ alkyl | phenyl and benzyl | hydrogen |
| $R^{11}$ | halogen, $C_1$-$C_4$ aliphatic, phenyl and benzyl, | hydrogen and $C_1$-$C_2$ alkyl | phenyl and benzyl | hydrogen |
| $R^{12}$ | 0 or 1 | 0 | 1 | |

Certain Synthesis Methods

Certain synthetic schemes are now provided. The synthetic schemes are provided only to illustrate possible ways to prepare compounds of the invention and do not limit the invention in any way. One of skill in the art will recognize that compounds of the present invention may be synthesized through any of a variety of schemes using a variety of different starting materials. In Scheme I the R groups (e.g., $R^1$, $R^2$, etc.) correspond to the specific substitution patterns noted in the Examples. However, it will be understood by those skilled in the art that other functionalities disclosed herein at the indicated positions of compounds of formula I also comprise potential substituents for the analogous positions on the structures within Scheme I.

Scheme I

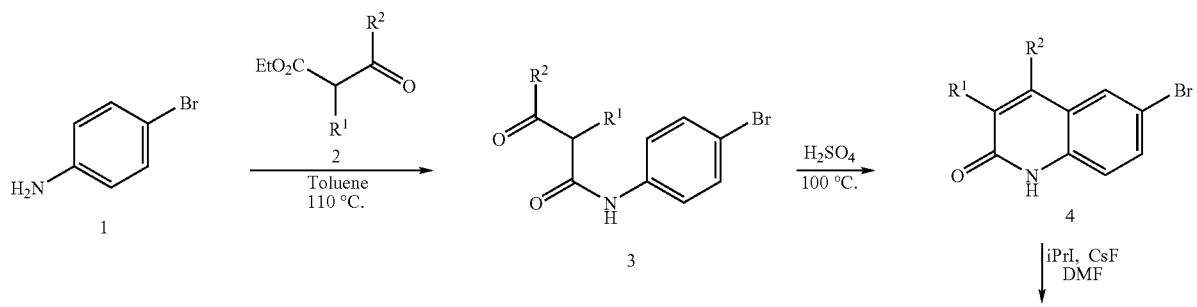

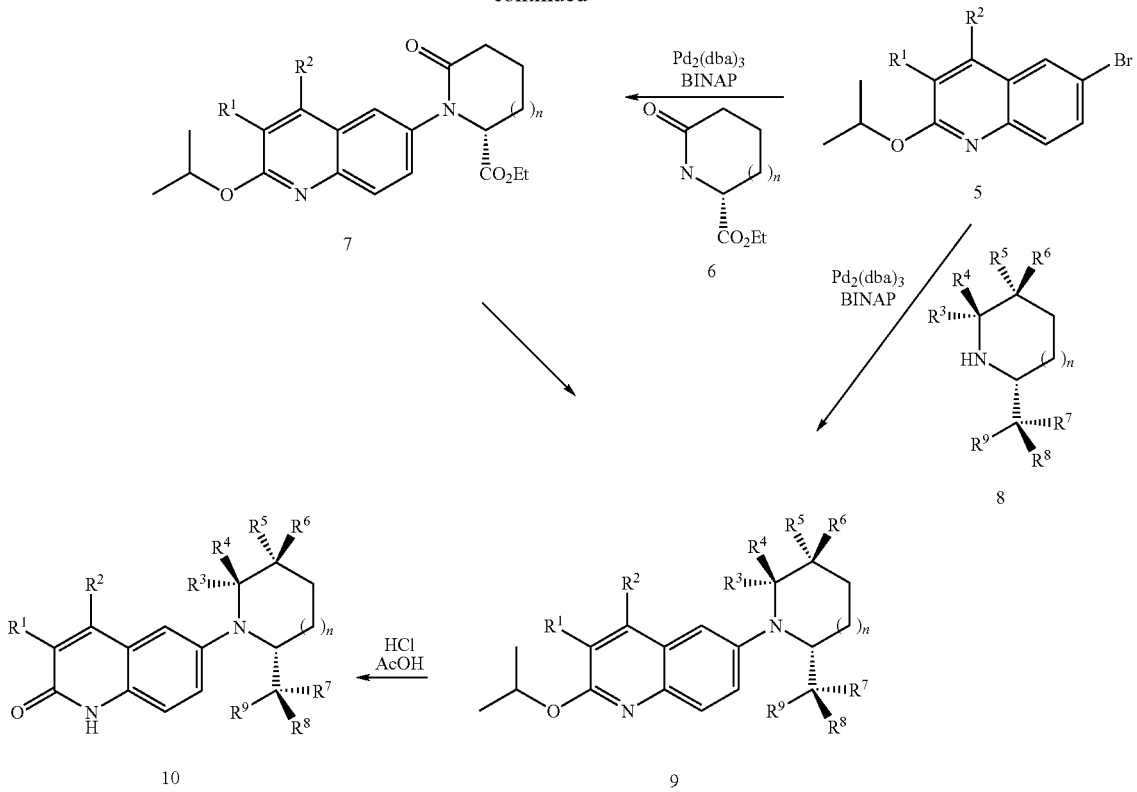

Scheme I describes the synthesis of 6-cycloamino compounds of Structure 10. The process begins with a step-wise Knorr reaction, in which 4-Bromoaniline (Structure 1) and a 3-ketoester (Structure 2) such as the trifluoroacetoacetate are heated in reflux in toluene to provide an amide (Structure 3) and heating of the amide in concentrated sulfuric acid affords 4-bromoquinolinones of Structure 4. Treatment of quinolinones of Structure 4 with 2-iodopropane, catalyzed by cesium fluoride in DMF affords alkoxyquinoline compounds of Structure 5. Palladium-catalyzed coupling reaction between bromoquinolines of Structure 5 and cycloalkylamines of Structure 6 gives compounds of Structure 7. Manipulation of the substitution pattern of Structure 7 affords intermediates of Structure 9. Alternately, palladium catalyzed coupling of bromoquinolines of Structure 5 and cycloalkylamines of Structure 8 directly gives compounds of Structure 9. Hydrolysis of the quinoline compounds (Structure 9) in acidic conditions provides compounds of Structure 10.

In certain embodiments, the invention provides a salt corresponding to any of the compounds provided herein. In certain embodiments, the invention provides a salt corresponding to a selective androgen receptor modulator. In certain embodiments, the invention provides a salt corresponding to a selective androgen receptor binding agent. In certain embodiments, a salt is obtained by reacting a compound with an inorganic acid, such as hydrochloric acid, hydrobromic acid, sulfuric acid, nitric acid, phosphoric acid, methanesulfonic acid, ethanesulfonic acid, p-toluenesulfonic acid, salicylic acid, and the like. In certain embodiments, a salt is obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like.

In certain embodiments, one or more carbon atoms of a compound of the present invention is replaced with silicon. See e.g., International Patent Application No. WO 03/037905A1; Tacke & Zilch, *Endeavour, New Series*, 10:191-197 (1986); Bains & Tacke, *Curr. Opin. Drug Discov Devel.* 6:52643 (2003). In certain embodiments, compounds of the present invention comprising one or more silicon atoms possess certain desired properties, including, but not limited to, greater stability and/or longer half-life in a patient, when compared to the same compound in which none of the carbon atoms have been replaced with a silicon atom.

Protecting groups that may be used in the present invention include those that are commonly known to those skilled in the art. Such groups include, but are not limited to TBDMS, TBS and Benzyl.

The compounds of the present invention also include isotopically labeled and radio-labeled compounds, which can be prepared by those of skilled in the art.

Certain Assays

In certain embodiments, compounds of the present invention are capable of modulating activity of androgen receptors in a "co-transfection" assay (also called a "cis-trans" assay), which has been discussed previously. See e.g., Evans et al., *Science*, 240:889-95 (1988); U.S. Pat. Nos. 4,981,784 and 5,071,773; Pathirana et al., *Mol. Pharm.* 47:630-35 (1995)). Modulating activity in a co-transfection assay has been shown to correlate with in vivo modulating activity. Thus, in certain embodiments, co-transfection assays are predictive of in vivo activity. See, e.g., Berger et al., *J. Steroid Biochem. Molec. Biol.* 41:773 (1992).

In certain co-transfection assays, two different co-transfection plasmids are prepared. In the first co-transfection plasmid, cloned cDNA encoding an intracellular receptor (e.g., androgen receptor) is operatively linked to a constitutive promoter (e.g., an SV 40 promoter). In the second co-transfection plasmid, cDNA encoding a reporter protein, such as firefly luciferase (LUC), is operatively linked to a promoter that is activated by a receptor-dependant activation factor. Both co-transfection plasmids are co-transfected into the same cells. Expression of the first co-transfection plasmid results in production of the intracellular receptor protein. Activation of that intracellular receptor protein (e.g., by binding of an agonist) results in production of a receptor-dependant activation factor for the promoter of the second co-transfection plasmid. That receptor-dependant activation factor in turn results in expression of the reporter protein encoded on the second co-transfection plasmid. Thus, reporter protein expression is linked to activation of the receptor. Typically, that reporter activity can be conveniently measured (e.g., as luciferase production).

Certain co-transfection assays can be used to identify agonists, partial agonists, and/or antagonists of intracellular receptors. In certain embodiments, to identify agonists, co-transfected cells are exposed to a test compound. If the test compound is an agonist or partial agonist, reporter activity is expected to increase compared to co-transfected cells in the absence of the test compound. In certain embodiments, to identify antagonists, the cells are exposed to a known agonist (e.g., an androgen for the androgen receptor) in the presence and absence of a test compound. If the test compound is an antagonist, reporter activity is expected to decrease relative to that of cells exposed only to the known agonist.

In certain embodiments, compounds of the invention are used to detect the presence, quantity and/or state of receptors in a sample. In certain of such embodiments, samples are obtained from a patient. In certain embodiments, compounds are radio- or isotopically-labeled. For example, compounds of the present invention that selectively bind androgen receptors may be used to determine the presence of such receptors in a sample, such as cell homogenates and lysates.

Certain Pharmaceutical Compositions

In certain embodiments, at least one selective androgen receptor modulator, or pharmaceutically acceptable salt, ester, amide, and/or prodrug thereof, either alone or combined with one or more pharmaceutically acceptable carriers, forms a pharmaceutical composition. Techniques for formulation and administration of compounds of the present invention may be found for example, in "Remington's Pharmaceutical Sciences," Mack Publishing Co., Easton, Pa., 18th edition, 1990.

In certain embodiments, a pharmaceutical composition comprising one or more compounds of the present invention is prepared using known techniques, including, but not limited to mixing, dissolving, granulating, dragee-making, levigating, emulsifying, encapsulating, entrapping or tabletting processes.

In certain embodiments, a pharmaceutical compositions comprising one or more compounds of the present invention is a liquid (e.g., a suspension, elixir and/or solution). In certain of such embodiments, a liquid pharmaceutical composition comprising one or more compounds of the present invention is prepared using ingredients known in the art, including, but not limited to, water, glycols, oils, alcohols, flavoring agents, preservatives, and coloring agents.

In certain embodiments, a pharmaceutical composition comprising one or more compounds of the present invention is a solid (e.g., a powder, tablet, and/or capsule). In certain of such embodiments, a solid pharmaceutical composition comprising one or more compounds of the present invention is prepared using ingredients known in the art, including, but not limited to, starches, sugars, diluents, granulating agents, lubricants, binders, and disintegrating agents.

In certain embodiments, a pharmaceutical composition comprising one or more compounds of the present invention is formulated as a depot preparation. Certain of such depot preparations are typically longer acting than non-depot preparations. In certain embodiments, such preparations are administered by implantation (for example subcutaneously or intramuscularly) or by intramuscular injection. In certain embodiments, depot preparations are prepared using suitable polymeric or hydrophobic materials (for example an emulsion in an acceptable oil) or ion exchange resins, or as sparingly soluble derivatives, for example, as a sparingly soluble salt.

In certain embodiments, a pharmaceutical composition comprising one or more compounds of the present invention comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition comprising one or more compounds of the present invention comprises one or more tissue-specific delivery molecules designed to deliver the pharmaceutical agent to specific tissues or cell types. For example, in certain embodiments, pharmaceutical compositions include liposomes coated with a tissue-specific antibody.

In certain embodiments, a pharmaceutical composition comprising one or more compounds of the present invention comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™, and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the percentage of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition comprising one or more compounds of the present invention comprises a sustained-release system. A non-limiting example of such a sustained-release system is a semipermeable matrix of solid hydrophobic polymers. In certain embodiments, sustained-release systems may, depending on their chemical nature, release compounds over a period of hours, days, weeks or months.

Certain compounds used in pharmaceutical composition of the present invention may be provided as pharmaceutically acceptable salts with pharmaceutically compatible counterions. Pharmaceutically compatible salts may be formed with many acids, including but not limited to hydrochloric, sulfuric, acetic, lactic, tartaric, malic, succinic, etc.

In certain embodiments, a pharmaceutical composition comprising one or more compounds of the present invention comprises an active ingredient in a therapeutically effective amount. In certain embodiments, the therapeutically effective amount is sufficient to prevent, alleviate or ameliorate symptoms of a disease or to prolong the survival of the subject being treated. Determination of a therapeutically effective amount is well within the capability of those skilled in the art.

In certain embodiments, a pharmaceutical composition comprising one or more compounds of the present invention is formulated as a prodrug. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, a prodrug is an ester. In certain embodiments, such prodrugs are less water soluble than the corresponding active form. In certain instances, such prodrugs possess superior transmittal across cell membranes, where water solubility is detrimental to mobility. In certain embodiments, the ester in such prodrugs is metabolically hydrolyzed to carboxylic acid. In certain instances the carboxylic acid containing compound is the corresponding active form. In certain embodiments, a prodrug comprises a short peptide (polyaminoacid) bound to an acid group. In certain of such embodiments, the peptide is metabolized to form the corresponding active form.

In certain embodiments, a pharmaceutical composition comprising one or more compounds of the present invention is useful for treating a conditions or disorder in a mammalian, and particularly in a human patient. Suitable administration routes include, but are not limited to, oral, rectal, transmucosal, intestinal, enteral, topical, suppository, through inhalation, intrathecal, intraventricular, intraperitoneal, intranasal, intraocular and parenteral (e.g., intravenous, intramuscular, intramedullary, and subcutaneous). In certain embodiments, pharmaceutical intrathecals are administered to achieve local rather than systemic exposures. For example, pharmaceutical compositions may be injected directly in the area of desired effect (e.g., in the renal or cardiac area).

In certain embodiments, a pharmaceutical composition comprising one or more compounds of the present invention is administered in the form of a dosage unit (e.g., tablet, capsule, bolus, etc.). In certain embodiments, such dosage units comprise a selective androgen receptor modulator in a dose from about 1 µg/kg of body weight to about 50 mg/kg of body weight. In certain embodiments, such dosage units comprise a selective androgen receptor modulator in a dose from about 2 µg/kg of body weight to about 25 mg/kg of body weight. In certain embodiments, such dosage units comprise a selective androgen receptor modulator in a dose from about 10 µg/kg of body weight to about 5 mg/kg of body weight. In certain embodiments, pharmaceutical compositions are administered as needed, once per day, twice per day, three times per day, or four or more times per day. It is recognized by those skilled in the art that the particular dose, frequency, and duration of administration depends on a number of factors, including, without limitation, the biological activity desired, the condition of the patient, and tolerance for the pharmaceutical composition.

In certain embodiments, a pharmaceutical composition comprising a compound of the present invention is prepared for oral administration. In certain of such embodiments, a pharmaceutical composition is formulated by combining one or more compounds of the present invention with one or more pharmaceutically acceptable carriers. Certain of such carriers enable compounds of the invention to be formulated as tablets, pills, dragees, capsules, liquids, gels, syrups, slurries, suspensions and the like, for oral ingestion by a patient. In certain embodiments, pharmaceutical compositions for oral use are obtained by mixing one or more compounds of the present invention and one or more solid excipient. Suitable excipients include, but are not limited to, fillers, such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). In certain embodiments, such a mixture is optionally ground and auxiliaries are optionally added. In certain embodiments, pharmaceutical compositions are formed to obtain tablets or dragee cores. In certain embodiments, disintegrating agents (e.g., cross-linked polyvinyl pyrrolidone, agar, or alginic acid or a salt thereof, such as sodium alginate) are added.

In certain embodiments, dragee cores are provided with coatings. In certain of such embodiments, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to tablets or dragee coatings.

In certain embodiments, pharmaceutical compositions for oral administration are push-fit capsules made of gelatin. Certain of such push-fit capsules comprise one or more compounds of the present invention in admixture with one or more filler such as lactose, binders such as starches, and/or lubricants such as talc or magnesium stearate and, optionally, stabilizers. In certain embodiments, pharmaceutical compositions for oral administration are soft, sealed capsules made of gelatin and a plasticizer, such as glycerol or sorbitol. In certain soft capsules, one or more compounds of the present invention are be dissolved or suspended in suitable liquids, such as fatty oils, liquid paraffin, or liquid polyethylene glycols. In addition, stabilizers may be added.

In certain embodiments, pharmaceutical compositions are prepared for buccal administration. Certain of such pharmaceutical compositions are tablets or lozenges formulated in conventional manner.

In certain embodiments, a pharmaceutical composition is prepared for administration by injection (e.g., intravenous, subcutaneous, intramuscular, etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory compositions such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the compounds to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition is prepared for administration by inhalation. Certain of such pharmaceutical compositions for inhalation are prepared in the form of an aerosol spray in a pressurized pack or a nebulizer. Certain of such pharmaceutical compositions comprise a propellant, e.g., dichlorodifluoromethane, trichlorofluoromethane, dichlorotetrafluoroethane, carbon dioxide or other suitable gas. In certain embodiments using a pressurized aerosol, the dosage unit may be determined with a valve that delivers a metered amount. In certain embodiments, capsules and cartridges for use in an inhaler or insufflator may be formulated. Certain of such formulations comprise a powder mixture of a compound of the invention and a suitable powder base such as lactose or starch.

In certain embodiments, a pharmaceutical composition is prepared for rectal administration, such as a suppositories or retention enema. Certain of such pharmaceutical compositions comprise known ingredients, such as cocoa butter and/or other glycerides.

In certain embodiments, a pharmaceutical composition is prepared for topical administration. Certain of such pharmaceutical compositions comprise bland moisturizing bases, such as ointments or creams. Exemplary suitable ointment bases include, but are not limited to, petrolatum, petrolatum plus volatile silicones, lanolin and water in oil emulsions such as Eucerin™, available from Beiersdorf (Cincinnati, Ohio). Exemplary suitable cream bases include, but are not limited to, Nivea™ Cream, available from Beiersdorf (Cincinnati, Ohio), cold cream (USP), Purpose Cream™, available from Johnson & Johnson (New Brunswick, N.J.), hydrophilic ointment (USP) and Lubriderm™, available from Pfizer (Morris Plains, N.J.).

In certain embodiments, the formulation, route of administration and dosage for a pharmaceutical agent of the present invention can be chosen in view of a particular patient's condition. (See e.g., Fingl et al. 1975, in "The Pharmacological Basis of Therapeutics", Ch. 1 p. 1). In certain embodiments, a pharmaceutical agent is administered as a single dose. In certain embodiments, a pharmaceutical agent is administered as a series of two or more doses administered over one or more days.

In certain embodiments, a pharmaceutical agent of the present invention is administered to a patient between about 0.1% and 500%, more preferably between about 25% and 75% of an established human dosage. Where no human dosage is established, a suitable human dosage may be inferred from ED50 or ID50 values, or other appropriate values derived from in vitro or in vivo studies.

In certain embodiments, a daily dosage regimen for a patient comprises an oral dose of between 0.1 mg and 2000 mg of a compound of the present invention. In certain embodiments, a daily dosage regimen is administered as a single daily dose. In certain embodiments, a daily dosage regimen is administered as two, three, four, or more than four doses.

In certain embodiments, a pharmaceutical agent of the present invention is administered by continuous intravenous infusion. In certain of such embodiments, from 0.1 mg to 500 mg of a composition of the present invention is administered per day.

In certain embodiments, a pharmaceutical agent of the invention is administered for a period of continuous therapy. For example, a pharmaceutical agent of the present invention may be administered over a period of days, weeks, months, or years.

Dosage amount, interval between doses, and duration of treatment may be adjusted to achieve a desired effect. In certain embodiments, dosage amount and interval between doses are adjusted to maintain a desired concentration on compound in a patient. For example, in certain embodiments, dosage amount and interval between doses are adjusted to provide plasma concentration of a compound of the present invention at an amount sufficient to achieve a desired effect. In certain of such embodiments the plasma concentration is maintained above the minimal effective concentration (MEC). In certain embodiments, pharmaceutical agents and compositions of the present invention are administered with a dosage regimen designed to maintain a concentration above the MEC for 10-90% of the time, between 30-90% of the time, or between 50-90% of the time.

In certain embodiments in which a pharmaceutical agent or composition is administered locally, the dosage regimen is adjusted to achieve a desired local concentration of a compound of the present invention.

In certain embodiments, a pharmaceutical composition may be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

In certain embodiments, a pharmaceutical composition is in powder form for constitution with a suitable vehicle, e.g., sterile pyrogen-free water, before use.

Certain Combination Therapies

In certain embodiments, one or more pharmaceutical agents of the present invention are co-administered with one or more other pharmaceutical agents. In certain embodiments, such one or more other pharmaceutical agents are designed to treat the same disease or condition as the one or more pharmaceutical agents of the present invention. In certain embodiments, such one or more other pharmaceutical agents are designed to treat a different disease or condition as the one or more pharmaceutical agents of the present invention. In certain embodiments, such one or more other pharmaceutical agents are designed to treat an undesired effect of one or more pharmaceutical agents of the present invention. In certain embodiments, one or more pharmaceutical agents of the present invention is co-administered with another pharmaceutical agent to treat an undesired effect of that other pharmaceutical agent. In certain embodiments, one or more pharmaceutical agents of the present invention and one or more other pharmaceutical agents are administered at the same time. In certain embodiments, one or more pharmaceutical agents of the present invention and one or more other pharmaceutical agents are administered at the different times. In certain embodiments, one or more pharmaceutical agents of the present invention and one or more other pharmaceutical agents are prepared together in a single formulation. In certain embodiments, one or more pharmaceutical agents of the present invention and one or more other pharmaceutical agents are prepared separately.

Examples of pharmaceutical agents that may be co-administered with a pharmaceutical agent of the present invention include, but are not limited to, analgesics (e.g., acetaminophen); anti-inflammatory agents, including, but not limited to non-steroidal anti-inflammatory drugs (e.g., ibuprofen, COX-1 inhibitors, and COX-2, inhibitors); salicylates; antibiotics; antivirals; antifungal agents; antidiabetic agents (e.g., biguanides, glucosidase inhibitors, insulins, sulfonylureas, and thiazolidinediones); adrenergic modifiers; diuretics; hormones (e.g., anabolic steroids, androgen, estrogen, calcitonin, progestin, somatostatin, and thyroid hormones); immunomodulators; muscle relaxants; antihistamines; osteoporosis agents (e.g., biphosphonates, calcitonin, and estrogens); prostaglandins, antineoplastic agents; psychotherapeutic agents; sedatives; poison oak or poison sumac products; antibodies; and vaccines.

Certain Indications

In certain embodiments, the invention provides methods of treating a patient comprising administering one or more compounds of the present invention. In certain embodiments, such patient suffers from a androgen receptor mediated condition. In certain embodiments, a patient is treated prophylactically to reduce or prevent the occurrence of a condition.

Exemplary conditions that may be treated with one or more compounds of the present invention included, but are not limited to, acne, male-pattern baldness, wasting diseases, hirsutism, hypogonadism, osteoporosis, infertility, impotence, obesity, and cancer. In certain embodiments, one or more compounds of the present invention are used to stimulate hematopoiesis. In certain embodiments, one or more compounds of the present invention are used for contraception.

In certain embodiments, one or more compounds of the present invention are used to treat cancer. Certain exemplary cancers include, but are not limited to, breast cancer, colorectal cancer, gastric carcinoma, glioma, head and neck squamous cell carcinoma, papillary renal carcinoma, leukemia, lymphoma, Li-Fraumeni syndrome, malignant pleural mesothelioma, melanoma, multiple myeloma, non-small cell lung cancer, synovial sarcoma, thyroid carcinoma, transitional cell carcinoma of urinary bladder, and prostate cancer, including, but not limited to prostatic hyperplasia.

In certain embodiments, one or more compounds of the present invention are used to improve athletic performance. In certain of such embodiments, one or more compounds of the present invention are used, for example to shorten the time normally needed to recover from physical exertion or to increase muscle strength. Athletes to whom one or more compounds of the present invention may be administered include, but are not limited to, horses, dogs, and humans. In certain embodiments, one or more compounds of the present invention are administered to an athlete engaged in a professional or recreational competition, including, but not limited to weight-lifting, body-building, track and field events, and any of various team sports.

In certain embodiments, the invention provides methods for treating a patient comprising administering one or more selective androgen receptor agonists and/or partial agonists. Exemplary conditions that may be treated with such selective androgen receptor agonists and/or partial agonist include, but are not limited to, hypogonadism, wasting diseases, cancer cachexia, frailty, infertility, and osteoporosis. In certain embodiments, a selective androgen receptor agonist or partial agonist is used for male hormone replacement therapy. In certain embodiments, one or more selective androgen receptor agonists and/or partial agonists are used to stimulate hematopoiesis. In certain embodiments, a selective androgen receptor agonist or partial agonist is used as an anabolic agent. In certain embodiments, a selective androgen receptor agonist and/or partial agonist is used to improve athletic performance.

In certain embodiments, the invention provides methods for treating a patient comprising administering one or more selective androgen receptor antagonists and/or partial agonists. Exemplary conditions that may be treated with such one or more selective androgen receptor antagonists and/or partial agonists include, but are not limited to, hirsutism, acne, male-pattern baldness, prostatic hyperplasia, and cancer, including, but not limited to, various hormone-dependent cancers, including, without limitation, prostate and breast cancer.

EXAMPLES

The following examples, including experiments and results achieved, are provided for illustrative purposes only and are not to be construed as limiting the present invention.

Example 1

(R)-6-(2-(2,2,2-Trifluoroethyl)-1-pyrrolidinyl)-4-trifluoromethyl-2(1H)-quinolinone (Compound 101, Structure 10 of Scheme I, where $R^1=R^3=R^4=R^5=R^6=R^7=R^8=H$, $R^2=R^9=$trifluoromethyl, n=0)

This compound was prepared by the general procedure illustrated in Scheme I as a yellow solid: $^1H$ NMR (500 MHz, $CDCl_3$) 11.78 (bs, 1H), 7.36 (d, 2H, J=8.9), 7.08 (s, 1H), 6.99 (dd, 1H, J=2.4 and 8.9), 6.89 (bs, 1H), 4.08 (bt, 1H, J=8.9), 3.52 (m, 1H), 3.24 (m, 1H), 2.49 (m, 1H), 2.22-2.07 (m, 5H).

Example 2

(R)-6-(2-Phenylthiomethyl-1-pyrrolidinyl-4-trifluoromethyl-2(1H)-quinolinone (Compound 102, Structure 10 of Scheme I, where $R^1=R^3=R^4=R^5=R^6=R^7=R^8=H$, $R^2=$trifluoromethyl, $R^9=$phenylthio, n=0)

This compound was prepared by the general procedure illustrated in Scheme I as a solid: $^1H$ NMR ($CDCl_3$, 500 MHz)

Example 3

(R)-6-(2-(2,2,2-Trifluoroethyl)-1-piperidinyl)-4-trifluoromethyl-2(1H)-quinolinone (Compound 103, Structure 10 of Scheme I, where $R^1=R^3=R^4=R^5=R^6=R^7=R^8=H$, $R^2=R^9=$trifluoromethyl, n=1)

This compound was prepared by the general procedure illustrated in Scheme I as a yellow solid: $^1H$ NMR ($CDCl_3$, 500 M&) 11.65 (bs, 1H), 7.37-7.27 (m, 2H), 7.21 (m, 1H), 7.08 (bs, 1H), 4.14 (m, 1H), 3.31 (m, 1H), 2.93 (m, 1H), 2.43 (m, 1H), 2.15-1.69 (m, 7H).

Example 4

(R)-6-(2-Benzyloxymethyl)-1-piperidinyl-4-trifluoromethyl-2(1)-quinolinone (Compound 104, Structure 10 of Scheme I, where $R^1=R^3=R^4=R^5=R^6=R^7=R^8=H$, $R^2$=trifluoromethyl, $R^9$=benzyloxy, n=1

This compound was prepared by the general procedure illustrated in Scheme I as a yellow solid: $^1$H NMR (CDCl$_3$, 500 MHz) 7.40-7.19 (m, 8H), 7.07 (s, 1H), 4.41 (dd, 2H, J=7.9 and 11.9), 4.05 (m, 1H), 3.57 (dd, 1H, J=7.6 and 9.5), 3.48 (dd, 1H, J=5.2 and 9.5), 3.32-3.29 (m, 1H), 3.03 (m, 1H), 1.95 (m, 1H), 1.88-1.78 (m, 3H), 1.69-1.61 (m, 2H).

Example 5

(R)-6-(2-Diethylaminomethyl-pyrrolidinyl)-4-trifluoromethyl-2(1H)-quinolinone (Compound 105, Structure 10 of Scheme I, where $R^1=R^3$, $R^4=R^5=R^6=R^7=R^8=H$, $R^2$=trifluoromethyl, $R^9$=diethylamino, n=0)

This compound was prepared by the general procedure illustrated in Scheme I as a solid: $^1$H NMR (CDCl$_3$, 500 MHz) 12.38 (bs, 1H), 7.36 (d, 1H, J=8.9), 7.07 (s, 1H), 7.05 (dd, 1H, J=2.7 and 9.2), 7.08 (s, 1H), 6.89 (bs, 1H), 3.50 (m, 1H), 3.46 (m, 1H), 3.19 (m, 1H), 2.69 (m, 2H), 2.53 (m, 3H), 2.29-1.95 (m, 5H), 1.06 (d, 3H, J=7.0), 1.05 (d, 3H, J=7.0).

Example 6

6-(2(R)-Hydroxymethl-5(S)-methyl-1-pyrrolidinyl)-4-trifluoromethyl-2(1H)-quinolinone (Compound 106, Structure 10 of Scheme I, where $R^1=R^4=R^5=R^6=R^7=R^8=H$, $R^7$=trifluoromethyl, $R^3$=methyl, $R^9$=hydroxy, n=0)

This compound was prepared by the general procedure illustrated in Scheme I as a solid: $^1$H NMR (CDCl$_3$, 500 MHz) 11.80 (bs, 1H), 7.31 (d, 1H, J=9.2), 7.18 (d, 1H, J=8.9), 7.06 (s, 1H), 7.03 (s, 1H), 3.90-3.69 (m, 4H), 1.78-1.44 (m, 4H), 1.34 (d, 3H, J=6.1).

Example 7

6-(2(R)-Fluoromethyl-5(R)-methyl-1-pyrrolidinyl)-4-trifluoromethyl-2(1H)-quinolinone (Compound 107, Structure 10 of Scheme I, where $R^1=R^3=R^5=R^6=R^7=R^8=H$, $R^2$=trifluoromethyl, $R^4$=methyl, $R^9$=fluorine, n=0) and 6-(2(R)-Fluoromethyl-5(S)-methyl-1-pyrrolidinyl)-4-trifluoromethyl-2(1H-quinolinone (Compound 108, Structure 10 of Scheme I, where $R^1=R^4=R^5=R^6=R^7=R^8=H$, $R^2$=trifluoromethyl, $R^3$=methyl, $R^9$=fluorine, n=0)

These compounds were prepared by the general procedure illustrated in Scheme I as solids.

Compound 107: $^1$H NMR (CDCl$_3$, 500 M ) 11.62 (bs, 1H), 7.33 (m, 2H), 7.24 (bs, 1H), 7.07 (bs, 1H), 4.76-4.65 (m, 1H), 3.82 (m, 1H), 3.48 (dt, 1H, J=4.9 and 11.6), 3.10 (m, 1H), 2.04 (m, 1H), 1.92 (m, 2H), 1.81 (m, 1H), 1.04 (d, 3H, J=6.4).

Compound 108: $^1$H NMR (500 MHz, CDCl$_3$) 11.44 (bs, 1 μl), 7.30 (d, 1H, J=9.2), 7.10 (dd, 1H, J=2.7 and 9.2), 7.07 (s, 1H), 6.99 (bs, 1H), 4.55-4.43 (m, 1H), 4.46-4.34 (m, 1H), 4.02 (m, 1H), 3.84 (m, 1H), 2.22 (m, 2H), 2.04 (m, 2H), 1.78 (m, 1H), 1.32 (d, 3H, J=6.0).

Example 8

6-(2(R)-Difluoromethyl-5(R)-methyl-1-pyrrolidinyl)-4-trifluoromethyl-2(1H)-quinolinone (Compound 109, Structure 10 of Scheme I, where $R^1=R^3=R^5=R^6=R^7=H$, $R^2$=trifluoromethyl, $R^4$=methyl, $R^8=R^9$=fluorine, n=0) and 6-(2(R)-Fluoromethyl-5(O-methyl-1-pyrrolidinyl)-4-trifluoromethyl-2(1H)-quinolinone (Compound 110, Structure 10 of Scheme I, where $R^1=R^4=R^5=R^6=R^7=H$, $R^2$=trifluoromethyl, $R^3$=methyl, $R^8=R^9$=fluorine, n=0)

These compounds were prepared by the general procedure illustrated in Scheme I as solids.

Compound 109: $^1$H NMR (500 M, CDCl$_3$) 11.97 (bs, 1H), 7.36 (d, 1H, J=8.9), 7.11 (dd, 1H, J=2.1 and 9.1), 7.08 (s, 1H), 6.98 (bs, 1H), 5.81 (dt, 1H, J=2.4 and 57.1), 4.29-4.17 (m, 2), 2.30-2.18 (m, 3H), 1.12 (d, 3H, J=6.1).

Compound 110: $^1$H NMR (500 MHz, CDCl$_3$) 12.36 (bs, if), 7.39 (d, 1H, J=8.9), 7.16 (dd, 1H, J=2.4, 8.9), 7.09 (s, 1H), 7.08 (bs, 1H), 5.83 (dt, 1H, J=4.0 and 56.2), 3.99 (m, 1H), 3.90 (m, 1H), 2.29-2.15 (m, 2H), 2.01 (m, 1H), 1.82 (m, 1H), 1.35 (d, 3H, J=6.1).

Example 9

6-(2(R)-(1(R)-Hydroxy-2,2,2-trifluoroethyl)-5(S)-methyl-1-pyrrolidinyl)-4-trifluoromethyl-2(1H)-quinolinone (Compound 111, Structure 10 of Scheme I, where $R^1=R^3=R^5=R^6=R^8=H$, $R^2$=trifluoromethyl, $R^4$=methyl, $R^7$=trifluoromethyl, $R^9$=hydroxy, n=0), 6-(2(R)-(1(S-Hydroxy-2,2,2-trifluoroethyl)-5(S)-methyl-1-pyrrolidinyl)-4-trifluoromethyl-2(1H)-quinolinone (Compound 112, Structure 10 of Scheme I, where $R^1=R^3=R^5=R^6=R^7=H$, $R^2$=trifluoromethyl, $R^4$=methyl, $R^8$=trifluoromethyl, $R^9$=hydroxy, n=0), 6-(2(R)-(1(S)-Hydroxy-2,2,2-trifluoroethyl)-5(R)-methyl-1-pyrrolidinyl)-4-trifluoromethyl-2(1H-quinolinone (Compound 113, Structure 10 of Scheme I, where $R^1=R^4=R^5=R^6=R^7=H$, $R^2$=trifluoromethyl, $R^3$=methyl, $R^8$=trifluoromethyl, $R^9$=hydroxy, n=0), and 6-(2(R)-(1(R-Hydroxy-2,2,2-trifluoroethyl)-5(R)-methyl-1-pyrrolidinyl)-4-trifluoromethyl-2(1H-quinolinone (Compound 114. Structure 10 of Scheme I, where $R^1=R^4=R^5=R^6=R^3=H$, $R^2$=trifluoromethyl, $R^3$=methyl, $R^7$=trifluoromethyl, $R^9$=hydroxy, n=0)

These compounds were prepared by the general procedure illustrated in Scheme I as solids.

Compound 111: $^1$H NMR (CDCl$_3$, 500 MHz) 12.36 (br, 1H), 7.35 (d, 1H, J=9.0), 7.09 (dd, 1H, J=9.5 and 2.5), 6.97 (s, 1H), 6.79 (br, 1H), 4.38 (m, 1H), 4.18 (m, 2H), 3.97 (br, 1H), 2.38 (m, 2H), 2.17 (m, 2H), 1.04 (d, 3H, J=6.0).

Compound 112: $^1$H NMR (500 MHz, CDCl$_3$) 10.80 (br, 1H), 7.17-7.23 (m, 2H), 7.01 (m, 1H), 6.98 (s, 1H), 4.31 (t, 1H, J=7.5), 4.25 (m, 1H), 3.88 (m, 1H), 3.75 (br, 1H), 2.35 (m, 1H), 2.25 (m, 1H), 1.98 (m, 1H), 1.81 (m, 1H), 1.09 (d, 3H, J=6.5); Compound 113: $^1$H NMR (500 MHz, CDCl$_3$) 11.59 (br, 1H), 7.35 (d, 1H, J=9.0), 7.28 (dd, 1H, J=9.5, 3.0), 7.25 (m, 1H), 7.08 (s, 1H), 4.04 (t, 1H, J=7.5), 3.79 (m, 1H), 3.71 (m, 1H), 3.45 (s, 1H), 2.32 (m, 1H), 2.05 (m, 1H), 1.91 (m, 1H), 1.72 (m, 1H), 1.40 (d, 3H, J=6.0); Compound 114: $^1$H NMR (500 MHz, CDCl$_3$) 12.20 (br, 1H), 7.33 (d, 1H, J=9.5), 7.08 (dd, 1H, J=9.5 and 2.5), 6.98 (s, 1H), 6.84 (m, 1H), 4.39

(m, 1H), 4.09 (m, 1H), 3.82 (m, 1H), 3.42 (br, 1H), 2.49 (m, 1H), 2.01-2.09 (m, 2H), 1.78 (m, 1H), 1.32 (d, 3H, J=6.5).

Example 10

6-(2(R)-(2,2,2-Trifluoroethyl)-5(R)-methyl-1-pyrrolidinyl)-4-trifluoromethyl-2(1H)-quinolinone (Compound 115. Structure 10 of Scheme I, where $R^1=R^4=R^5=R^6=R^7=R^8=R^2=R^9=$trifluoromethyl, $R^3=$methyl, n=0)

This compound was prepared by the general procedure illustrated in Scheme I as a solid: $^1$H NMR (CDCl$_3$, 500 MHz) 12.78(br, 1H), 7.42 (d, 1H, J=9.0), 7.08 (s, 1H), 7.04 (dd, 1H, J=9.0 and 2.5), 6.92 (m, 1H), 4.00 (m, 1H), 3.85 (m, 1H), 2.67 (m, 1H), 2.10-2.30 (m, 3H), 2.02 (m, 1H), 1.78 (m, 1H), 1.31 (d, 3H, J=6.5).

Example 11

6-(2(R)-(1(S)-Hydroxy-2,2,2-trifluoroethyl)-4(R)-hydroxy-1-pyrrolidinyl)-4-trifluoromethyl-2(1H)-quinolinone (Compound 116 Structure 10 of Scheme I, where $R^1=R^3=R^4=R^6=R^7=$H $R^5=R^9=$hydroxy, $R^2=R^8=$trifluoromethyl, n=0) and 6-(2(R)-(1 (R)-Hydroxy-2,2,2-trifluoroethyl)-4(R)-hydroxy-1-1-pyrolidinyl)-4-trifluoromethyl-2(1H)-quinolinone (Compound 117, Structure 10 of Scheme I, where $R^1=R^3=R^1=R^6=R^8=$H, $R^5=R^9=$hydroxy, $R^2=R^7=$trifluoromethyl, n=0

These compounds were prepared by the general procedure illustrated in Scheme I as solids. Compound 116: $^1$H NMR (CDCl$_3$, 500 MHz) 10.70 (br, 1H), 7.26-7.30 (m, 1H), 7.21 (d, 1H, J=9.0), 7.03 (m, 1H), 6.99 (s, 1H), 5.56 (t, 1H, J=5.0), 4.28 (m, 2H), 3.80 (br, 1H), 3.70 (d, 1H, J=12.0), 3.57 (dd, 1H, J=12.0 and 5.5), 2.35 (m, 1H), 2.25 (d, J=15.0);

Compound 117: $^1$H NMR (500 MHz, CD$_3$COCD$_3$) 7.48 (d, 2H, J=9.0), 7.18 (dd, 1H, J=9.0 and 2.5), 6.91 (s, 1H), 6.89 (m, 1H), 4.65 (t, 1H, J=5.0), 4.45 (m, 1H), 4.39 (d, 1H, J=10.0), 3.67(d, 1H, J=10.0), 3.47 (dd, 1H, J=10.0, 5.0), 2.52 (m, 1H), 2.36 (d, 1H, J=14.5).

Example 12

6-(2(R)-(1(S)-Fluoro-2,2,2-trifluoroethyl)-4(S)-fluoro-1-pyrrolidinyl)-4-trifluoromethyl-2(1H)-quinolinone (Compound 118, Structure 10 of Scheme I, where $R^1=R^3$, $R^4=R^5=R^7=$H, $R^6=R^9=$fluorine, $R^2=R^8=$trifluoromethyl, n=0) and 6-(2(R)-(1(R)-fluoro-2,2,2-trifluoroethyl)-4(S)-fluoro-1-pyrrolidinyl)-4-trifluoromethyl-2(1H)-quinolinone (Compound 119, Structure 10 of Scheme I, where $R^1=$=$R^4=R^5=R^8=$H, $R^6=R^9=$fluorine, $R^2=R^7=$trifluoromethyl, n=0)

These compounds were prepared by the general procedure illustrated in Scheme I as solids.

Compound 118: $^1$H NMR (CDCl$_3$, 500 MHz) 11.69 (br, 1H), 7.26-7.38 (m, 3H), 7.11 (s, 1H), 5.22-5.31(m, 1H), 4.96-5.08 (m, 1H), 4.42 (m, 1H), 3.89 (m, 1H), 3.46 (m, 2H), 2.74 (m, 1H), 2.02-2.13 (m, 1H).

Compound 119: $^1$H NMR (CDCl$_3$, 500 MHz) 11.78 (br, 1H), 7.32-7.38 (m, 3H), 7.10 (s, 1H), 5.28-5.38 (m, 1H), 5.07-5.16 (m, 1H), 4.56 (m, 1H), 3.54-3.83 (m, 2H), 2.27-2.53(m, 2H).

Example 13

6-(2(R)-(1(S)-Hydroxy-2,2,2-trifluoroethyl)-4(R)-methyl-1-pyrrolidinyl)-4-trifluoromethyl-2(1H)-quinolinone (Compound 120, Structure 10 of Scheme I, where $R^1=R^3=R^4=R^6=R^7=$H, $R^5=$methyl, $R^9=$hydroxy, $R^2=R^8=$trifluoromethyl, n=0), 6-(2(R)-(1(R)-Hydroxy-2,2,2-trifluoroethyl)-4(R)-methyl-1-pyrrolidinyl)-4-trifluoromethyl-2(1H)-quinolinone (Compound 121, Structure 10 of Scheme I, where $R^1=R^3=R^4=R^6=R^8=$H, $R^5=$methyl, $R^9=$hydroxy, $R^2=R^7=$trifluoromethyl, n=0), 6-(2(R)-(1(S)-Hydroxy-2,2,2-trifluoroethyl)-4(S)-methyl-1-pyrrolidinyl)-4-trifluoromethyl-2(1)-quinolinone (Compound 122, Structure 10 of Scheme I, where $R^1=R^3=R^4=R^5=R^7=$H, $R^6=$methyl, $R^9=$hydroxy $R^2=R^8=$trifluoromethyl, n=0), and 6-(2(R)-(1(R)-Hydroxy-2,2,2-trifluoroethyl)-4(S)-methyl-1-pyrrolidinyl)-4-trifluoromethyl-2(1H)-quinolinone (Compound 123. Structure 10 of Scheme I, where $R^1=R^3=R^4=R^5=R^8=$H, $R^6=$methyl, $R^9=$hydroxy, $R^2=R^7=$trifluoromethyl, n=0)

These compounds were prepared by the general procedure illustrated in Scheme I as solids.

Compound 120: $^1$H NMR (CDCl$_3$, 500 MHz) 12.1 (bs, 1H), 7.26 (bs, 1H), 7.24 (bs, 1H), 7.04 (bs, 1H), 6.93 (s, 1H), 4.45 (bs, 1H), 4.22 (m, 1H), 4.04 (m, 1H), 3.49 (m, 1H), 3.23 (m, 1H), 2.42 (m, 1H), 2.34 (m, 1H), 1.68 (m, 1H), 1.16 (d, 3H, J=6.5).

Compound 121: $^1$H NMR (500 MHz, CDCl$_3$) 12.45 (bs, 1H), 7.32 (d, 1H, J=9.0), 6.92 (dd, 1H, J=2.5, 9.0), 6.87 (bs, 1H), 6.69 (bs, 1H), 4.54 (m, 1H), 4.43 (bs, 1H), 4.20 (m, 1H), 3.40 (m, 1H), 2.93 (m, 1H), 2.21 (m, 1H), 2.10 (m, 1H), 1.80 (m, 1H), 1.07 (d, 3H, J=6.0);

Compound 122: $^1$H NMR (500 MHz, CDCl$_3$) 11.64 (bs, 1H), 7.26 (bs, 1H), 7.23 (bs, 1H), 7.21 (bs, 1H), 7.01 (bs, 1H), 4.11 (dd, 1H, J=7.9 and 15.9), 4.03 (bs, 1H), 3.85 (m, 1H), 3.68 (dd, 1H, J=7.4 and 7.6), 2.76 (dd, 1H, J=8.9 and 10.4), 2.55 (m, 1H), 2.05 (m, 1H), 1.70 (m, 1H), 1.19 (d, 3H, J=6.4).

Compound 123: $^1$H NMR (500 MHz, CDCl$_3$) 7.26 (bs, 1H), 7.05 (s, 1H), 7.01 (dd, 1H), 6.98 (bs, 1H), 4.38 (m, 1H), 4.18 (m, 1H), 4.08 (m, 1H), 3.78 (m, 1H), 2.95-2.25 (m, 2H), 2.65 (m, 1H), 1.17 (d, 3H).

Example 14

6(2(R)-(1(S)-Hydroxy-2,2,2-trifluoroethyl)-4(R)-methoxy-1-pyrrolidinyl)-4-trifluoromethyl-2(1)-quinolinone (Compound 124, Structure 10 of Scheme I, where $R^1=R^3=R^4=R^6=R^7=$H, $R^5=$methoxy, $R^9=$hydroxy $R^2=R^8=$trifluoromethyl, n=0), 6-(2(R)-(1 (R)-Hydroxy-2,2,2-trifluoroethyl-4 (R)-methoxy-1-pyrrolidinyl)-4-trifluoromethyl-2 (1H)-quinolinone (Compound 125, Structure 10 of Scheme I, where $R^1=R^3=R^4=R^6=R^8=$H, $R^5=$methoxy, $R^9=$hydroxy, $R^2=R^7=$trifluoromethyl, n=0), 6-(2(R)-(1(R)-Hydroxy-2,2,2-trifluoroethyl)-4 (S)-methoxy-1-pyrrolidinyl)-4-trifluoromethyl-2 (1H)-quinolinone (Compound 126, Structure 10 of Scheme I, where $R^1=R^3=R^4=R^5=R^8=$H, $R^6=$methoxy, $R^9=$hydroxy, $R^2=R^7=$trifluoromethyl, n=0) and 6-(2(R)-(1(S)-Hydroxy-2,2,2-trifluoroethyl)-4(S)-methoxy-1-pyrrolidinyl)-4-trifluoromethyl-2(1H)-quinolinone (Compound 127, Structure 10 of Scheme I, where $R^1=R^3=R^4=R^5=R^7=$H, $R^6=$methoxy, $R^9=$hydroxy, $R^2=R^8=$trifluoromethyl, n=0)

These compounds were prepared by the general procedure illustrated in Scheme I as solids.

Compound 124: $^1$H NMR (500 MHz, CDCl$_3$) 11.48 (bs, 1H), 7.24 (bs, 1H), 7.23 (bs, 1H), 7.05 (s, 1H), 7.02 (s, 1H), 4.31 (m, 1H), 4.21 (m, 1H), 4.16 (m, 1H), 3.90 (bs, 1H), 3.74 (d, 1H, J=10.7), 3.41 (s, 3H), 3.36 (m, 1H), 2.28 (d, 1H, J=14.0), 2.15 (m, 1H, J=6.6).

Compound 125: $^1$H NMR (500, CDCl$_3$) 11.95 (bs, 1H), 7.39 (d, 1H, J=8.9), 7.09 (s, 1H), 7.03 (dd, 1H, J=2.7 and 9.1), 6.95 (bs, 1H), 5.12 (d, 1H, J=4.0), 4.39 (d, 1H, J=9.8), 4.37 (bs, 1H), 4.20 (dd, 1H, J=4.7 and 4.9), 3.83 (d, 1H, J=10.7), 3.52 (s, 3H), 3.37 (m, 1H), 2.58 (d, 1H, J=15.3), 2.32 (m, 1H).

Compound 126: $^1$H NMR (500 MHz, CDCl$_3$) 11.13 (bs, 1H), 7.24 (s, 2H), 7.09 (s, 1H), 7.01 (s, 1H), 4.33 (dt, 1H, J=3.1 and 7.0), 4.21 (m, 1H), 3.90 (m, 1H), 3.80 (dd, 1H, J=5.8 and 9.8), 3.69 (bs, 1H), 3.38 (s, 3H), 3.29 (dd, 1H, J=5.8 and 9.7), 2.30-2.19 (m, 2H).

Compound 127: $^1$H NMR (500 MHz, CDCl$_3$) 11.49 (bs, 1H), 7.29 (d, 1H, J=8.9), 6.99 (m, 2H), 6.84 (bs, 1H), 4.45 (m, 1H), 4.33 (t, 1H, J=6.7), 4.22 (m, 1H), 3.72 (dd, 1H, J=5.2 and 9.8), 3.34-3.56 (m, 4H).

Example 15

4-Chloro-6-(2(R)-(1(S)-hydroxy-2,2,2-trifluoroethyl)-5(R)-methyl-1-pyrrolidinyl)-2(1H-quinolinone (Compound 128, Structure 10 of Scheme I, where $R^1=R^4=R^5=R^6=R^7=H$, $R^3$=methyl, $R^9$=hydroxy, $R^2$=chlorine. $R^8$=trifluoromethyl, n=0) and 4-Chloro-6-(2(R)-(1(R)-hydroxy-2,2,2-trifluoroethyl)-5(R)-methyl-1-pyrrolidinyl)-2(1H)-quinolinone (Compound 129, Structure 10 of Scheme I, where $R^1=R^4=R^5=R^6=R^8=H$, $R^3$=methyl, $R^9$=hydroxy, $R^2$=chlorine, $R^7$=trifluoromethyl, n=0)

These compounds were prepared by the general procedure illustrated in Scheme I as solids.

Compound 128: $^1$H NMR (500 MHz, CDCl$_3$) 12.29 (br, 1H), 7.30-7.33 (m, 2H), 7.24 (dd, 1H, J=9.5, 2.5), 6.80 (s, 1H), 4.06 (m, 1H), 3.82 (m, 1H), 3.73 (m, 1H), 2.30 (m, 1H), 2.05 (m, 1H), 1.90 (m, 1H), 1.74 (m, 1H), 1.40 (d, 3H, J=6.0).

Compound 129: $^1$H NMR (500 MHz, CD$_3$COCD$_3$) 10.82 (br, 1H), 7.37 (d, 1H, J=9.0), 7.11 (dd, 1H, J=9.5 and 3.0), 6.99 (d, 1H, J=3.0), 6.66 (s, 1H), 5.75 (d, 1H, J=7.0), 4.47 (m, 1H), 4.14(t, 1H, J=6.5), 3.90 (m, 1H), 2.50 (m, 1H), 1.95-2.15 (m, 2H), 1.85 (m, 1H), 1.36 (d, 3H, J=6.0).

Example 16

4-Chloro-6-(2(R)-(1(S)-hydroxy-2,2,2-trifluoroethyl)-1-pyrrolidinyl-2(1H)-quinolinone (Compound 130, Structure 10 of Scheme I, where $R^1=R^3=R^4=R^5=R^6=R^7=H$, $R^9$=hydroxy, $R^2$=chlorine, $R^8$=trifluoromethyl, n=0) and 4-Chloro-6-(2(R)-(1(R)-hydroxy-2,2,2-trifluoroethyl)-1-pyrrolidinyl)-2(1H)-quinolinone (Compound 131, Structure 10 of Scheme I, where $R^1=R^3=R^4=R^5=R^6=R^8=H$, $R^9$=hydroxy, $R^2$=chlorine, $R^7$=trifluoromethyl, n=0)

These compounds were prepared by the general procedure illustrated in Scheme I as solids.

Compound 130: $^1$H NMR (500 MHz, CD$_3$COCD$_3$) 10.69 (br, 1H), 7.34 (d, 1H, J=8.5), 7.24 (dd, 1H, J=9.0 and 3.0), 7.16 (d, 1H, J=3.0), 6.68 (s, 1H), 5.41 (d, 1H, J=4.5), 4.17 (m, 1H), 4.12 (m, 1H), 3.62 (t, 1H, J=8.0), 3.22 (m, 1H), 2.00-2.20 (m, 4H).

Compound 131: $^1$H NMR (500 MHz, CD$_3$COCD$_3$) 10.76 (br, 1H), 7.38 (d, 1H, J=9.0), 7.09 (dd, 1H, J=9.0 and 2.5), 6.98 (d, 1H, J=3.0), 6.69 (s, 1H), 5.61 (br, 1H), 4.45 (m, 1H), 4.17 (d, 1H, J=8.0), 3.66 (m, 1H), 3.25 (m, 1H), 2.42 (m, 1H), 2.31 (m, 1H), 2.00-2.20 (m, 2H).

Example 17

6-(2(R)-(1(R)-Hydroxy-1-methyl-2,2,2-trifluoroethyl)-5(R)-methyl-1-pyrrolidinyl)-4-trifluoromethyl-2 (1H)-quinolinone (Compound 132. Structure 10 of Scheme I, where $R^1=R^4=R^5=R^6=H$, $R^3=R^8$=methyl, $R^9$=hydroxy, $R^2=R^7$-trifluoromethyl, n=0) and 6-(2 (R)-(1(S)-Hydroxy-1-methyl-2,2,2-trifluoroethyl)-5 (R)-methyl-1-pyrrolidinyl)-4-trifluoromethyl-2(1H-quinolinone (Compound 133. Structure 10 of Scheme I, where $R^1=R^4=R^5=R^6=H$, $R^3=R^7$=methyl, $R^9$=hydroxy, $R^2=R^8$ trifluoromethyl n=0)

These compounds were prepared by the general procedure illustrated in Scheme I as solids.

Compound 132: $^1$H NMR (500, Acetone-D$_6$) 10.91 (bs, 1H), 7.47 (d, 1H, J=9.3), 7.28 (dd, 1H, J=2.9 and 9.3), 7.05 (bs, 1H), 6.91 (s, 1H), 5.08 (s, 1H), 4.18 (d, 1H, J=7.8), 3.84 (m, 1H), 2.41 (m, 1H), 2.24 (m, 1H), 1.90 (m, 1H), 1.45 (s, 3H), 1.43 (d, 3H, J=10.3);

Compound 133: $^1$H NMR (500 MHz, Acetone-D$_6$) 10.91 (bs, 1H), 7.56 (dd, 1H, J=2.9 and 9.3), 7.44 (m, 1H), 7.40 (d, 1H, J=8.9), 6.89 (s, 1H), 4.97 (s, 1H), 4.27 (dd, 1H, J=3.4 and 8.3), 3.77 (m, 1H), 2.23 (m, 1H), 2.06 (m, 1H), 1.85 (m, 1H), 1.49 (s, 3H), 1.43 (d, 3H, J=6.3).

Example 18

6-(2(R)-(1-Hydroxy-1-trifluoromethyl-2,2,2-trifluoroethyl)-5(R)-methyl-1-pyrrolidinyl)-4-trifluoromethyl-2(1H)-quinolinone (Compound 134. Structure 10 of Scheme I, where $R^1=R^4=R^5=R^6=H$, $R^3$=methyl, $R^9$=hydroxy, $R^2=R^7=R^8$-trifluoromethyl, n=0)

This compound was prepared by the general procedure illustrated in Scheme I as a solid: $^1$H NMR (500 MHz, Acetone-D$_6$) 10.99 (bs, 1H), 7.54-7.44 (m, 3H), 6.76 (bs, 1H), 4.52 (d, 1H, J=7.3), 3.65 (m, 1H), 2.40 (m, 1H), 2.26 (m, 2H), 1.88 (m, 1H), 1.37 (d, 3H, J=5.9).

Example 19

6-(2(R)-(1 (R)-Ethoxy-2,2,2-trifluoroethyl)-1-pyrrolidinyl)-4-trifluoromethyl-2(1H)-quinolinone (Compound 135, Structure 10 of Scheme I, where $R^1=R^3=R^4=R^5=R^6=R^8=H$, $R^9$=ethoxy, $R^2=R^7$=trifluoromethyl, n=1)

This compound was prepared by the general procedure illustrated in Scheme I as a solid: $^1$H NMR (500 MHz, CD$_3$COCD$_3$) 7.50 (d, 1H, J=8.5), 7.18 (dd, 1H, J=9.5 and 3.0), 6.94 (s, 1H), 6.88 (m, 1H), 4.15 (m, 2H), 3.77 (m, 1H), 3.65(m, 1H), 3.56 (m, 1H), 3.29 (m, 1H), 2.23-2.37 (m, 2H), 2.00-2.18 (m, 2H), 1.11 (t, 3H, J=7.0).

Example 20

6-(2(R)-(1(R)-Hydroxy-2,2,2-trifluoroethyl)-1-pyrrolidinyl)-4-propyl-2(1H)-quinolinone (Compound 136, Structure 10 of Scheme I, where $R^1=R^3=R^4=R^5=R^6=R^8=H$, $R^9$=hydroxy, $R^2$=propyl $R^7$=trifluoromethyl, n=0) and 6-(2(R)-(1(S)-Hydroxy-2,2,2-trifluoroethyl)-1-pyrrolidinyl-4-propyl-2 (1H)-quinolinone (Compound 137, Structure 10 of Scheme I, where $R^1=R^3=R^4=R^5=R^6=R^7=H$, $R^9$=hydroxy $R^2$=propyl, $R^8$=trifluoromethyl, n=0)

These compounds were prepared by the general procedure illustrated in Scheme I as solids.

Compound 136: $^1$H NMR (500 MHz, CD$_3$ OD) 7.26 (d, 1H, J=8.8), 7.16 (dd, 1H, J=2.9 and 8.8), 7.09 (d, 1H, J=2.9), 6.45 (s, 1H), 4.08 (t, 1H, J=7.3), 3.93 (t, 1H, J=7.3), 3.61 (m, 1H), 3.20 (m, 1H), 2.84 (m, 2H), 2.13-1.98 (m, 4H), 1.81-1.75 (m, 2H), 1.06 (t, 3H, J=7.3).

Compound 137: $^1$H NMR (500 MHz, CD$_3$ OD) 7.31 (d, 1H, J=9.3), 7.05 (dd, 1H, J=2.9 and 9.3), 6.84 (d, 1H, J=2.4), 6.48 (s, 1H), 4.31 (q, 1H, J=8.3), 4.11 (d, 1H, J=5.9), 3.65 (dt, 1H, J=2.4 and 7.3), 3.22 (m, 1H), 2.82 (m, 2H), 2.39 (m, 1H), 2.27 (m, 1H), 2.03-1.97 (m, 2H), 1.74 (m, 2H), 1.05 (t, 3H, J=7.3).

Example 21

6-(2(R)-(1(S)-Hydroxy-2,2,2-trifluoroethyl)-1-pyrrolidinyl)-4-ethyl-2(1H)-quinolinone (Compound 138, Structure 10 of Scheme I, where $R^1=R^3=R^4=R^5=R^6=R^7=H$, $R^9$=hydroxy, $R^2$=ethyl, $R^8$=trifluoromethyl, n=0) and 6-(2(R)-(1(R)-Hydroxy-2,2,2-trifluoroethyl)-1-pyrrolidinyl-4-ethyl-2 (1H-quinolinone (Compound 139, Structure 10 of Scheme I, where $R^1=R^3=R^4=R^5=R^6=R^8=H$, $R^9$=hydroxy, $R^2$=ethyl, $R^7$=trifluoromethyl, n=0)

These compounds were prepared by the general procedure illustrated in Scheme I as solids.

Compound 138: $^1$H NMR (500 MHz, CD$_3$ OD) 7.25 (d, 1H), 7.18 (dd, 1H), 7.07 (d, 1H), 6.48 (s, 1H), 4.10 (m, 1H), 3.95 (t, 1H), 3.63 (m, 1H), 3.22 (m, 1H), 2.91 (q, 2H), 2.15-1.98 (m, 4H), 1.05 (t, 3H).

Compound 139: $^1$H NMR (500 MHz, CD$_3$ OD) 7.32 (d, 1H), 7.04 (dd, 1H), 6.86 (d, 1H), 6.48 (s, 1H), 4.30 (q, 1H), 4.12 (d, 1H), 3.64 (dt, 1H), 3.22 (m, 1H), 2.88 (q, 2H), 2.45-2.22 (m, 2H), 2.02 (m, 2H), 1.35 (t, 3H).

Example 22

6-(2(R)-Chloromethyl-5-(R)-methyl-1-pyrrolidinyl)-4-trifluoromethyl-2(1H)-quinolinone (Compound 140, Structure 10 of Scheme I, where $R^1=R^4$, $R^5=R^6=R^7=R^8=H$, $R^3$=methyl, $R^9$=chlorine, $R^2$=trifluoromethyl, n=) and 6-(2(R)-Chloromethyl-5-(S)-methyl-1-pyrrolidinyl)-4-trifluoromethyl-2 (1H)-quinolinone (Compound 141, Structure 10 of Scheme I, where $R^1=R^3=R^5=R^6$, $R^7=R^8=H$, $R^4$=methyl, $R^9$=chlorine, $R^2$=trifluoromethyl, n=0)

These compounds were prepared by the general procedure illustrated in Scheme I as solids.

Compound 140: $^1$H NMR (500 MHz, CD$_3$ OD) 7.41 (d, 1H, J=8.8), 7.23 (dd, 1H, J=2.4 and 9.3), 7.01 (s, 1H), 6.95 (bs, 1H), 3.97 (m, 1H), 3.88 (m, 1H), 3.77 (dd, 1H, J=2.9 and 10.7), 3.53 (dd, 1H, J=9.3 and 10.7), 2.25 (m, 1H), 2.17-2.05 (m, 2H), 1.86 (m, 1H), 1.35 (t, 3H, J=6.3).

Compound 141: $^1$H NMR (CDCl$_3$, 500 MHz) 12.84 (bs, 1H), 7.45 (dd, 1H, J=4.9 and 9.3), 7.33 (dd, 1H, J=2.4 and 8.8), 7.20 (s, 1H), 7.13 (s, 1H), 4.10-4.01 (m, 2H), 3.63 (dd, 1H, J=3.4 and 11.7), 3.19 (dd, 1H, J=10.2 and 11.7), 2.20 (m, 1H), 2.16-1.94 (m, 2H), 1.83 (m, 1H), 1.11 (d, 3H, J=6.8).

Example 23

6-(2(R)-(1(S)-Hydroxy-2,2,2-trifluoroethyl)-5(S)-phenyl-1-pyrrolidinyl)-4-trifluoromethyl-2(1H)-quinolinone (Compound 142, Structure 10 of Scheme I, where $R^1=R^4=R^5=R^6=R^7=H$, $R^2$=trifluoromethyl $R^3$=phenyl, $R^8$=trifluoromethyl, $R^9$=hydroxy, n=0) and 6-(2(R)-(1(R)-Hydroxy-2,2,2-trifluoroethyl)-5(S)-phenyl-1-pyrrolidinyl)-4-trifluoromethyl-2(1H)-quinolinone (Compound 143, Structure 10 of Scheme I, where $R^1=R^4=R^5=R^6=R^8=H$, $R^2$=trifluoromethyl, $R^3$=phenyl $R^7$=trifluoromethyl, $R^9$=hydroxy, n=0)

These compounds were prepared by the general procedure illustrated in Scheme I as solids.

Compound 142: $^1$H NMR (500 MHz, CD$_3$ OD) 7.52 (s, 1H), 7.50 (s, 1H), 7.38-7.33 (m, 3H), 7.28-7.23 (m, 2H), 7.09 (bs, 1H), 6.89 (s, 1H), 4.70 (dd, 1H, J=6.8 and 10.3), 4.29 (m, 1H), 4.10 (m, 1H), 2.58 (m, 1H), 2.15 (m, 2H), 2.00 (m, 1H).

Compound 143: $^1$H NMR (500 MHz, CD$_3$ OD) 7.53 (s, 1H), 7.51 (s, 1H), 7.35 (m, 2H), 7.28-7.23 (m, 2H), 7.02 (dd, 1H, J=2.9, 9.3), 6.97 (bs, 1H), 6.93 (s, 1H), 4.65 (dd, 1H, J=7.3, 7.8), 4.55 (m, 1H), 4.25 (m, 1H), 2.50-2.43 (m, 2H), 2.28-2.22 (m, 1H), 2.07 (m, 1H).

Example 24

6-(2(R)-(1(S)-Hydroxy-2,2,2-trifluoroethyl)-5,5-dimethyl-1-pyrrolidinyl)-4-trifluoromethyl-2(1)-quinolinone (Compound 144, Structure 10 of Scheme I, where $R^1=R^5=R^6=R^7=H$, $R^2$=trifluoromethyl, $R^3=R^4$=methyl, $R^8$=trifluoromethyl, $R^9$=hydroxy, n=0) and 6-(2(R)-(1(R)-Hydroxy-2,2,2-trifluoroethyl)-5,5-dimethyl-1-pyrrolidinyl)-4-trifluoromethyl-2(1H)-quinolinone (Compound 145. Structure 10 of Scheme I, where $R^1=R^5=R^6=R^8=H$, $R^2$=trifluoromethyl, $R^3=R^4$=methyl, $R^7$=trifluoromethyl, $R^9$=hydroxy, n=0)

These compounds were prepared by the general procedure illustrated in Scheme I as solids.

Compound 144: $^1$H NMR (500 MHz, CD$_3$ OD) 7.55 (dd, 1H, J=2.4 and 8.8), 7.49 (bs, 1H), 7.38 (d, 1H, J=9.3), 7.01 (s, 1H), 4.31 (m, 1H), 3.90 (m, 1H), 2.30 (m, 1H), 2.04 (m, 2H), 1.89 (m, 1H), 1.46 (s, 3H), 1.07 (s, 3H).

Compound 145: $^1$H NMR (500 MHz, CD$_3$ OD) 7.44 (dd, 1H, J=2.4, 9.3), 7.49 (d, 1H, J=8.8), 7.26 (bs, 1H), 7.01 (s, 1H), 4.27 (t, 1H, J=6.3), 4.07 (m, 1H), 2.33 (m, 1H), 2.09-1.96 (m, 2H), 1.87 (m, 1H), 1.52 (s, 3H), 1.22 (s, 3H).

Example 25

6-(2(R)-(1(S)-Hydroxy-2,2,2-trifluoroethyl)-5(R)-phenyl-1-pyrrolidinyl)-4-trifluoromethyl-2(1H)-quinolinone (Compound 146 Structure 10 of Scheme I, where $R^1=R^4=R^5=R^6=R^7=H$, $R^2$=trifluoromethyl, $R^3$=phenyl, $R^1$=trifluoromethyl, $R^9$=hydroxy n=0) and 6-(2(R)-(1(R)-Hydroxy-2,2,2-trifluoroethyl, (R)-phenyl-1-pyrrolidinyl)-4-trifluoromethyl-2(1H)-quinolinone (Compound 147, Structure 10 of Scheme I, where $R^1=R^4=R^5=R^6=R^8=H$, $R^2$=trifluoromethyl, $R^3$=methyl, $R^7$=trifluoromethyl, $R^9$=hydroxy, n=0)

These compounds were prepared by the general procedure illustrated in Scheme I as solids.

Compound 146: $^1$H NMR (500 MHz, CD$_3$OD) 7.51 (dd, J=7.3 and 1.3 Hz, 2H), 7.35 (t, J=7.3 Hz, 2H), 7.26 (tt, J=7.3 and 1.3 Hz, 1H), 7.24 (d, J=9.2 Hz, 1H), 7.09 (m, 1H), 6.89 (s, 1H), 4.70 (dd, J=9.9 and 7.0 Hz, 1H), 4.29 (m, 1H), 4.11 (dq, J=9.2 and 6.8 Hz, 1H), 2.58 (m, 1H), 2.21-2.10 (m, 2H), 2.00 (m, 1H).

Compound 147: $^1$H NMR (500MHz, CD$_3$ OD) 7.52 (dd, J=7.4, 1.3 Hz, 2H), 7.35 (t, J=7.4 Hz, 2H), 7.26 (tt, J=7.4, 1.3 Hz, 1H), 7.02 (dd, J=9.0, 2.7 Hz, 1H), 6.97 (m, 1H), 6.93 (s, 1H), 4.65 (t, J=7.4 Hz, 1H), 4.55 (dq, J=0.9, 8.0 Hz, 1H), 4.26 (m, 1H), 2.50-2.42 (m, 2H), 2.25 (m, 1H), 2.08 (m, 1H).

Example 26

6-(2(R)-(1(R),2-Dihydroxyethyl)-1-pyrrolidinyl)-4-trifluoromethyl-2(1H)-quinolinone (Compound 148. Structure 10 of Scheme I, where $R^1=R^3=R^4=R^5=R^6=R^7=H$, $R^2$=trifluoromethyl, $R^8$=hydroxymethyl, $R^9$=hydroxy, n=0) and 6-(2(R)-(1(S),2-dihydroxyethyl)-1-pyrrolidinyl)-4-trifluoromethyl-2(1H)-quinolinone (Compound 149 Structure 10 of Scheme I, where $R^1=R^3=R^4=R^5=R^6=R^9=H$, $R^2$=trifluoromethyl $R^8$ hydroxymethyl, $R^7$=hydroxy n=0)

These compounds were prepared by the general procedure illustrated in Scheme I as solids.

Compound 148: $^1$H NMR (500 MHz, acetone-d$_6$) 11.93 (s, 1H), 7.46 (d, J=9.1 Hz, 1H), 7.23 (dd, J=9.1, 2.6 Hz, 1H), 6.97 (m, 1H), 6.86 (s, 1H), 4.03-3.96 (m, 2H), 3.90 (m, 1H), 3.61 (m, 2H), 3.57 (dt, J=10.2, 5.6 Hz, 1H), 2.25 (m, 2H), 1.95-1.86 (m, 2H).

Compound 149: $^1$H NMR (500 MHz, CD$_3$ OD) 7.34 (dd, J=9.1, 2.2 Hz, 1H), 7.32 (d, J=9.1 Hz, 1H), 6.98 (m, 1H), 6.94 (s, 1H), 3.95 (m, 1H), 3.78 (td, J=6.6, 3.3 Hz, 1H), 3.63 (dd, J=11.2, 3.3 Hz, 1H), 3.61-3.53 (m, 3H), 3.17 (m, 1H), 2.09-2.02 (m, 2H), 2.01-1.94 (m, 1H).

Example 27

6-(2(R)-(1(R)-Hydroxybenzyl)-5(S)-methyl-1-pyrolidinyl)-4-trifluoromethyl-2(1H)-quinolinone (Compound 150, Structure 10 of Scheme I, where $R^1=R^3=R^5=R^6=R^7=H$, $R^2$=trifluoromethyl, $R^4$=methyl, $R^8$=phenyl, $R^9$=hydroxy, n=0), 6-(2(R)-(1(S)-Hydroxybenzyl)-5(R)-methyl-1-pyrrolidinyl 4-trifluoromethyl-2(1H)-quinolinone (Compound 151, Structure 10 of Scheme I, where $R^1=R^4=R^5=R^6=R^9=H$, $R^2$=trifluoromethyl, $R^3$=methyl $R^8$=phenyl, $R^7$=hydroxy, n=0), and 6-(2(R)-(1 (B)-Hydroxybenzyl)-5(R$^3$-methyl-1-pyrrolidinyl)-4-trifluoromethyl-1-2(1H)-quinolinone (Compound 152, Structure 10 of Scheme I, where $R^1=R^4=R^5=R^6=R^7=H$, $R^2$ trifluoromethyl, $R^3$=methyl, $R^8$=phenyl, $R^9$=hydroxy, n=0)

These compounds were prepared by the general procedure illustrated in Scheme I as solids.

Compound 150: $^1$H NMR (500 z, CDCl$_3$) 11.32 (s, 1H), 7.48 (d, J=7.7 Hz, 2H), 7.47 (t, J=7.7 Hz, 1H), 7.41 (t, J=7.7 Hz, 2H), 7.36 (dd, J=9.2, 2.2 Hz, 1H), 7.34 (m, 1H), 7.32 (d, J=9.2 Hz, 1H), 7.08 (s, 1H), 4.60 (d, J=8.7 Hz, 1H), 3.95 (m, 1H), 3.80 (m, 1H), 2.22 (m, 1H), 2.12 (m, 1H), 1.80-1.73 (m, 2H), 1.36 (d, J=5.9 Hz, 3H).

Compound 151: $^1$H NMR (500 MHz, CDCl$_3$) 10.46 (s, 1H), 7.50-7.47 (m, 2H), 7.43-7.34 (m, 5H), 7.29 (d, J=9 Hz, 1H), 7.07 (s, 1H), 4.60 (d, J=8.8 Hz, 1H), 3.95 (m, 1H), 3.80 (m, 1H), 2.71 (m, 1H), 2.22 (m, 1H), 1.81-1.72 (m, 3H) and 1.36 (d, J=6.1 Hz, 3H).

Compound 152: $^1$H NMR (500 MHz, CDCl$_3$) 12.67 (s, 1H), 7.46 (dd, J=7.6, 1.2 Hz, 2H), 7.39 (td, J=7.6, 1.2 Hz, 2H), 7.41 (d, J=9.5 Hz, 1H), 7.29 (ft, J=7.6, 1.2 Hz, 1H), 7.17 (dd, J=9.5, 2.3 Hz, 1H), 7.17 (m, 1H), 7.08 (s, 1H), 5.19 (d, J=2.8 Hz, 1H), 3.98 (td, J=7.4, 2.8 Hz, 1H), 3.86 (m, 1H), 2.53 (m, 1H), 2.26 (ddt, J=12.5, 9.9, 7.4 Hz, 1H), 1.95 (ddt, J=12.0, 9.9, 7.4 Hz, 1H), 1.69 (m, 1H), 1.55 (ddt, J=12.5, 4.2, 7.4 Hz, 1H), 1.41 (d, J=6.3 Hz, 3H).

Example 28

6-(2(R)-((2-1,3-Dithianyl)-1(R)-hydroxymethyl)-5(R)-methyl-1-pyrrolidinyl)-4-trifluoromethyl-2(1H)-quinolinone (Compound 153, Structure 10 of Scheme I, where $R^3=R^4=R^5=R^6=R^7=H$, $R^2$=trifluoromethyl, $R^3$=methyl, $R^8$=2-1,3-dithiane, $R^9$=hydroxy, n=0) and 6-(2(R)-((2-1,3-Dithianyl)-1(S)-hydroxymethyl)-5(R)-methyl-1-pyrrolidinyl)-4-trifluoromethyl-2(1H)-quinolinone (Compound 154, Structure 10 of Scheme I, where $R^1=R^4=R^5=R^6=R^9=H$, $R^2$=trifluoromethyl, $R^3$=methyl, $R^8$=2-1,3-dithiane, $R^7$=hydroxy, n=0)

These compounds were prepared by the general procedure illustrated in Scheme I as solids.

Compound 153: $^1$H NMR (500 MHz, CDCl$_3$) 11.02 (s, 1H), 7.32 (dd, J=9.2, 2.4 Hz, 1H), 7.25 (d, J=9.2 Hz, 1H), 7.17 (m, 1H), 7.05 (s, 1H), 3.75 (m, 1H), 3.62 (m, 1H), 3.43 (m, 1H), 2.46 (m, 1H), 2.22 (m, 1H), 1.89 (m, 1H), 1.80-1.70 (m, 3H), 1.49-1.38 (m, 4H), 1.37 (d, J=6.0 Hz, 3H), 0.96 (t, J=7.2 Hz, 3H).

Compound 154: $^1$H NMR (500 MHz, CDCl$_3$) 10.84 (s, 1H), 7.25 (d, J=9.0 Hz, 1H), 7.09 (dd, J=9.0, 2.4 Hz, 1H), 7.05 (s, 1H), 6.99 (m, 1H), 3.98 (m, 1H), 3.81 (m, 1H), 3.74 (m, 1H), 2.23 (m, 1H), 2.01 (m, 1H), 1.90 (m, 1H), 1.70 (m, 1H), 1.40 (m, 1H), 1.34 (d, J=6.3 Hz, 3H).

Example 29

6-(2(R)-Difluoromethyl-5,5-dimethyl-1-pyrrolidinyl)-4-trifluoromethyl-2(1H)-quinolinone (Compound 155, Structure 10 of Scheme I, where $R^1=R^5=R^6=R^7=H$, $R^1$=trifluoromethyl, $R^3=R^4$=methyl, $R^8=R^9$=fluorine, n=0)

This compound was prepared by the general procedure illustrated in Scheme I as solid.

Compound 155: $^1$H NMR (500 MHz, acetone-d$_6$) 11.09 (s, 1H), 7.54 (dd, J=9.0, 2.2 Hz, 1H), 7.45 (d, J=9.0 Hz, 1H), 7.41 (qn, J=2.2 Hz, 1H), 6.92 (s, 1H), 5.78 (ddd, J=56.9, 56.1, 4.1 Hz, 1H), 4.27 (m, 1H), 2.24 (m, 1H), 2.00 (m, 2H), 1.91 (m, 1H), 1.41 (s, 3H), 1.10 (s, 3H).

Example 30

6-(2(R)-Fluoromethyl-5,5-dimethyl-1-pyrrolidinyl)-4-trifluoromethyl-2(1H)-quinolinone (Compound 156, Structure 10 of Scheme L, where $R^1=R^5=R^6=R^7=R^8=H$, $R^2$=trifluoromethyl, $R^3=R^4$=methyl, $R^9$=fluorine, n=0)

This compound was prepared by the general procedure illustrated in Scheme I as solid.

Compound 156: $^1$H NMR (500 MHz, CDCl$_3$) 12.32 (s, 1H), 7.36 (d, J=9.0 Hz, 1H), 7.27-7.24 (m, 2H), 7.07 (s, 1H), 4.38 (ddd, J=46.5, 9.3, 3.7 Hz, 1H), 4.28 (ddd, J=47.4, 9.3, 6.3

Hz, 1H), 4.15 (m, 1H), 2.16 (m, 1H), 2.04-1.93 (m, 2H), 1.88 (m, 1H), 1.49 (s, 3H), 1.23 (s, 3H).

Example 31

6-(2(R)-Hydroxymethyl-5,5-dimethyl-1-pyrrolidinyl-4-trifluoromethyl-2(1H)-quinolinone (Compound 157, Structure 10 of Scheme I, where $R^1=R^5=R^6=R^7=R^8=H$, $R^2$=trifluoromethyl, $R^3=R^4$=methyl $R^9$=hydroxy, n=0)

This compound was prepared by the general procedure illustrated in Scheme I as solid.

Compound 157: $^1$H NMR (500 MHz, CDCl$_3$) 12.23 (s, 1H), 7.36 (d, J=8.9 Hz, 1H), 7.32 (s, if), 7.32 (d, J=8.9 Hz, 1H), 7.07 (s, 1H), 3.98 (m, 1H), 3.58 (dd, J=11.1, 4.3 Hz, 1H), 3.53 (d, J=11.1 Hz, 1H), 2.11-2.00 (m, 2H), 1.94 (m, 1H), 1.83 (dt, J=12.1, 6.9 Hz, 1H), 1.44 (s, 3H), 1.12 (s, 3H).

Example 32

6-(2(R)-Hydroxymethyl-1-piperidinyl)-4-trifluoromethyl-2(1H)-quinolinone (Compound 158, Structure 10 of Scheme I, where $R^1=R^3=R^4=R^5=R^6=R^7=R^8=H$, $R^2$=trifluoromethyl, $R^9$=hydroxy, n=1)

This compound was prepared by the general procedure illustrated in Scheme I as solid.

Compound 158: $^1$H NMR (500 MHz, CDCl$_3$) 12.60 (s, 1H), 7.39 (d, J=9.3 Hz, 1H), 7.35 (dd, J=9.3, 2.0 Hz, 1H), 7.20 (qn, J=2.0 Hz, 1H), 7.08 (s, 1H), 4.31 (dd, J=10.4, 5.7 Hz, 1H), 4.10 (m, 1H), 4.06 (dd, J=10.4, 6.8 Hz, 1H), 3.34 (m, 1H), 3.12 (m, 1H), 1.91-1.81 (m, 3H), 1.72-1.65 (m, 3H).

Example 33

6-2(R)-(1(S)-Hydroxyethyl-1-piperidinyl)-4-trifluoromethyl-2(1H)-quinolinone (Compound 159, Structure 10 of Scheme I, where $R^1=R^3=R^4=R^5=R^6=R^8=H$, $R^2$=trifluoromethyl, $R^7$=methyl, $R^9$=hydroxy, n=1) and 6-(2(R)-(1(R)-Hydroxyethyl-1-piperidinyl)-4-trifluoromethyl-2(1H)-quinolinone (Compound 160, Structure 10 of Scheme I, where $R^1=R^3=R^5=R^6=R^7=H$, $R^2$=trifluoromethyl, $R^8$=methyl, $R^9$=hydroxy, n=1)

These compounds were prepared by the general procedure illustrated in Scheme I as solids.

Compound 159: $^1$H NMR (500 MHz, CDCl$_3$) 12.36 (s, 1H), 7.36 (d, J=9.0 Hz, 1H), 7.27 (dd, J=9.0, 2.0 Hz, 1H), 7.16 (qn, J=2.0 Hz, 1H), 7.07 (s, 1H), 5.38 (dq, J=8.5, 6.4 Hz, 1H), 3.75 (m, 1H), 3.45 (m, 1H), 3.14 (m, 1H), 1.81-1.65 (m, 4H), 1.26 (m, 2H), 1.13 (d, J=6.4 Hz, 3H).

Compound 160: $^1$H NMR (500 MHz, CDCl$_3$) 11.62 (s, 1H), 7.29-7.28 (m, 2H), 7.11 (m, 1H), 7.05 (s, 1H), 3.86 (m, 1H), 3.35 (m, 1H), 3.24 (m, 1H), 3.16 (m, 1H), 1.84-1.73 (m, 4H), 1.67-1.60 (m, 2H), 1.21 (d, J=6.3 Hz, 3H).

Example 34

6-(2(R)-Trifluoroacetyl-1-piperidinyl-4-trifluoromethyl-2(1H)-quinolinone (Compound 161, Structure 10 of Scheme I, where $R^1=R^3=R^4=R^5=R^6=H$, $R^2$=trifluoromethyl-1, $R^7$, $R^8$=carbonyl, $R^9$=trifluoromethyl, n=1)

This compound was prepared by the general procedure illustrated in Scheme I as solid.

Compound 161: $^1$H NMR (500 MHz, CDCl$_3$) 7.54 (d, J=9.0 Hz, III), 7.49 (dd, J=8.8 and 2.4 Hz, 1H), 7.39 (br s, 1H), 6.99 (br s, 1H), 5.86 (t, J=3.5 Hz), 4.31 (q, J=6.7 Hz), 3.76 (dt, J=13 and 3.5 Hz), 3.45 (ddd, J=13.0, 11.1, and 2.2 Hz, 2H), 2.28-2.24 (m, 2H).

Example 35

6-(2(R)-(1(S)-Hydroxypentyl-1-piperidinyl)-4-trifluoromethyl-2(1H)-quinolinone (Compound 162, Structure 10 of Scheme I, where $R^1=R^3=R^4=R^5=R^6=R^8=H$, $R^2$=trifluoromethyl, $R^7$=n-butyl, $R^9$=hydroxy, n=1) and 6-(2(R)-(1(R)-Hydroxypentyl-1-piperidinyl)-4-trifluoromethyl-1-2 (1H)-quinolinone (Compound 163. Structure 10 of Scheme I, where $R^1=R^3=R^4=R^5=R^6=R^7=H$, $R^2$=trifluoromethyl-1. $R^8$=n-butyl, $R^9$=hydroxy, n=1

These compounds were prepared by the general procedure illustrated in Scheme I as solids.

Compound 162: $^1$H NMR (500 MHz, CDCl$_3$) 12.79 (s, 1H), 7.46-7.39 (m, 3H), 7.10 (s, 1H), 3.72 (dt, J=8.0, 4.2 Hz, 1H), 3.25 (dt, J=7.5, 4.2 Hz, 1H), 3.19 (dt, J=12.2, 5.0 Hz, 1H), 3.05 (ddd, J=12.2, 6.9, 5.1 Hz, 1H), 2.10 (s, 1H), 1.91-1.79 (m, 2), 1.77-1.66 (m, 2), 1.50 (m, 1H), 1.45-1.30 (m, 3H), 1.30-1.17 (m, 4H), 0.84 (t, J=7.1 Hz, 3H).

Compound 163: $^1$H NMR (500 MHz, CDCl$_3$) 12.40 (s, 1H), 7.36 (m, 2H), 7.30 (m, 1H), 7.08 (s, 1H), 4.08 (ddd, J=9.5, 8.4, 2.3 Hz, 1H), 3.59 (m, 1H), 3.50 (dd, J=9.5, 3.7 Hz, 1H), 3.32 (ddd, J=14.5, 12.2, 2.7 Hz, 1H), 2.82 (s, 1H), 1.77-1.64 (m, 6H), 1.50-1.34 (m, 5H), 0.95 (t, J=7.3 Hz, 3H).

Example 36

6-(2(R&-(1(R)-Hydroxyethyl)-5(R)-methyl-1-pyrrolidinyl)-4-trifluoromethyl-2(1H)-quinolinone (Compound 164, Structure 10 of Scheme I, where $R^1=R^4=R^5=R^6=R^7=H$, $R^2$=trifluoromethyl, $R^3=R^8$=methyl, $R^9$=hydroxy, n=°

This compound was prepared by the general procedure illustrated in Scheme I as solid.

Compound 164: $^1$H NMR (500 MHz, CDCl$_3$) 12.23 (s, 1H), 7.36 (d, J=9.1 Hz, 1H), 7.10 (dd, J=9.1, 2.2 Hz, 1H), 7.07 (s, 1H), 6.99 (qn, J=2.2 Hz, 1H), 4.17 (dq, J=2.5, 6.3 Hz, 1H), 3.81 (m, 1H), 3.70 (td, J=7.4, 2.5 Hz, 1H), 2.23 (m, 1H), 2.02 (m, 1H), 1.96-1.88 (m, 2H), 1.71 (m, 1H), 1.35 (d, J=6.3 Hz, 3H), 1.24 (d, J=6.3 Hz, 3H).

Example 37

6-(2(R)-(1-Hydroxy-1-methylethyl)-5(R)-methyl-1-pyrrolidinyl)-4-trifluoromethyl-2(1H)-quinolinone (Compound 165, Structure 10 of Scheme I, where $R^1=R^4=R^5=R^6=H$, $R^2$=trifluoromethyl, $R^3=R^7=R^8$=methyl, $R^9$=hydroxy, n=0)

This compound was prepared by the general procedure illustrated in Scheme I as solid.

Compound 165: $^1$H NMR (500 MHz, CDCl$_3$) 12.37 (s, 1H), 7.43 (dd, J=9.2, 2.0 Hz, 1H), 7.35 (d, J=9.2 Hz, 1H), 7.30 (qn, J=2.0 Hz, 1H), 7.06 (s, 1H), 3.82 (dd, J=7.6, 4.1 Hz, 1H), 3.71 (sext, J=6.5 Hz, 1H), 2.12 (m, 1H), 2.00-1.88 (m, 3H), 1.77 (m, 1H), 1.41 (d, J=6.5 Hz, 3H), 1.26 (s, 6H).

Example 38

6-(2(R)-(1(S)-Hydroxy-1-cyclopropylmethyl)-5(R)-methyl-1-pyrrolidinyl-4-trifluoromethyl-2(1H-quinolinone (Compound 166. Structure 10 of Scheme I, where $R^1=R^4=R^5=R^6=R^8=H$, $R^2$=trifluoromethyl $R^3$=methyl, $R^7$=cyclopropyl, $R^9$=hydroxy, n=0) and 6-(2(R)-(1(R)-Hydroxy-1-cyclopropylmethyl)-5(R)-methyl-1-pyrrolidinyl-4-trifluoromethyl-2(1H)-quinolinone (Compound 167, Structure 10 of Scheme I, where $R^1=R^1=R^5=R^6=R^7=H$, $R^2$=trifluoromethyl, $R^3$=methyl, $R^8$=cyclopropyl, $R^9$=hydroxy, n=0)

These compounds were prepared by the general procedure illustrated in Scheme I as solids.

Compound 166: $^1$H NMR (500 MHz, CDCl$_3$) 7.24 (d, J=9.0 Hz, 1H), 7.09 (dd, J=9.0, 2.7 Hz, 1H), 7.04 (s, 1H), 6.95 (m, 1H), 3.93 (m, 1H), 3.82 (m, 1H), 3.20 (dd, J=8.8, 2.4 Hz, 1H), 2.09-2.01 (m, 2H), 1.78-1.69 (m, 2H), 1.36 (d, J=6.3 Hz, 3H)

Compound 167: $^1$H NMR (500 MHz, CDCl$_3$) 7.33 (dd, J=9.0, 2.5. Hz, 1H), 7.20 (d, J=9.0 Hz, 1H), 7.18 (m, 1H), 7.04 (s, 1H), 3.86 (m, 1H), 3.75 (m, 1H), 3.66 (m, 1H), 2.33-2.19 (m, 2H), 2.00 (m, 1H), 1.92 (m, 1H), 1.37 (d, J=5.9 Hz, 3H), 0.65-0.56 (m, 2H), 0.48 (m, 1H), 0.41 (m, 1H).

Example 39

6-(2(R)-(1(S)-Hydroxypropyl)-5(R)-methyl-1-pyrolidinyl)-4-trifluoromethyl-2(1H)quinolinone (Compound 168, Structure 10 of Scheme I, where R=$R^4$, $R^5=R^6=R^8=H$, $R^2$=trifluoromethyl, $R^3$=methyl, $R^7$=ethyl, $R^9$=hydroxy, n=0), 6-(2(R)-(1 (R)-hydroxypropyl)-5(S)-methyl-1-pyrrolidinyl)-4-trifluoromethyl-2(1H)-quinolinone (Compound 169, Structure 10 of Scheme I, where $R^1=R^3=R^5=R^6=R^7=H$, $R^2$=trifluoromethyl, $R^4$=methyl $R^8$=ethyl, $R^9$=hydroxy, n=0), 6-(2(R)-(1(R)-Hydroxypropyl)-5 (R)-methyl-1-pyrrolidinyl)-4-trifluoromethyl-2(1H)-quinolinone (Compound 170, Structure 10 of Scheme I, where $R^1=R^4=R^5=R^6=R^7=H$, $R^2$=trifluoromethyl $R^3$=methyl, $R^8$=ethyl, $R^9$=hydroxy, n=0), and 6-(2(R)-(1(S)-Hydroxypropyl-5(R)-methyl-1-pyrrolidinyl)-4-trifluoromethyl-2 (1H)-quinolinone (Compound 171, Structure 10 of Scheme I, where $R^1=R^3=R^5==R^8=H$, $R^2$-trifluoromethyl, $R^4$=methyl, $R^7$=ethyl $R^9$=hydroxy, n=0)

These compounds were prepared by the general procedure illustrated in Scheme I as solids.

Compound 168: $^1$H NMR (500 MHz, CDCl$_3$) 7.47 (d, J=8.9 Hz, 1H), 7.29 (d, J=8.9 Hz, 1H), 7.19 (m, 1H), 7.13 (s, 1H), 3.90 (m, 1H), 3.86-3.77 (m, 2H), 2.33 (m, 1H), 2.09 (m, 1H), 1.97 (m, 1H), 1.82 (m, 1H), 1.59 (m, 1H), 1.50 (m, 1H), 1.37 (d, J=6.3 Hz, 3H), 1.05 (t, J=7.4 Hz, 3H).

Compound 169: $^1$H NMR (500 MHz, CDCl$_3$) 12.06 (s, 1H), 7.35 (d, J=9.0 Hz, 1H), 7.11 (dd, J=9.0, 2.3 Hz, 1H), 7.05 (s, 1H), 6.89 (qn, J=2.3 Hz, 1H), 4.27 (m, 1H), 3.96 (t, J=6.5 Hz, 1H), 3.83 (m, 1H), 2.27 (m, 1H), 2.16-2.03 (m, 2H), 1.67 (m, 1H), 1.60 (m, 1H), 1.51 (m, 1H), 1.06 (t, J=7.5 Hz, 3H), 1.03 (d, J=6.2 Hz, 3H).

Compound 170: $^1$H NMR (500 MHz, CDCl$_3$) 7.68 (dd, J=9.0, 2.2 Hz, 1H), 7.54 (m, 1H), 7.21 (d, J=9.0 Hz, 1H), 7.02 (s, 1H), 4.08 (m, 1H), 3.84 (m, 1H), 3.69 (m, 1H), 2.37-2.29 (m, 2H), 2.07 (m, 1H), 1.91 (m, 1H), 1.71-1.57 (m, 2H), 1.38 (d, J=6.3 Hz, 3H), 1.04 (t, J=7.3 Hz, 3H).

Compound 171: $^1$H NMR (500 MHz, CDCl$_3$) 7.23 (d, J=8.9 Hz, 1H), 7.14 (dd, J=8.9, 2.2 Hz, 1H), 7.03 (s, 1H), 7.00 (qn, J=2.2 Hz, 1H), 4.22 (m, 1H), 3.98 (t, J=6.8 Hz, 1H), 3.62 (m, 1H), 2.19 (m, 2H), 1.90 (d, J=5.6 Hz, 1H), 1.39 (m, 4H), 1.07 (d, J=6.1 Hz, 3H), 0.97 (t, J=7.4 Hz, 3H).

Example 40

6-(2(R)-(1(R)-Hydroxy-2-methylpropyl)-5(R)-methyl-1-pyrrolidinyl-4-trifluoromethyl-2(1H)-quinolinone (Compound 172, Structure 10 of Scheme I, where $R^1=R^4=R^5=R^6=R^7=H$, $R^2$=trifluoromethyl, $R^3$=methyl, $R^8$=isopropyl, $R^9$=hydroxy, n Compound 172 was prepared according to the general procedure described in Scheme I as a solid, $^1$H NMR (500 MHz, CDCl$_3$) 11.86 (s, 1H), 7.33 (d, J=9.0 Hz, 1H), 7.30 (dd, J=9.0, 2.0 Hz, 1H), 7.22 (qn, J=2.0 Hz, 1H), 7.06 (s, 1H), 3.79-3.72 (m, 2H), 3.20 (dd, J=9.7, 3.4 Hz, 1H), 2.23 (m, 1H), 1.93-1.66 (m, 5H), 1.37 (d, J=5.9 Hz, 3H), 1.13 (d, J=6.8 Hz, 3H), 1.11 (d, J=6.8 Hz, 3H).

Example 41

6-(2(R)-(1 (R)-Hydroxy-2-acetoxyethyl)-1-pyrrolidinyl)-4-trifluoromethyl-2(1H)-quinolinone (Compound 173, Structure 10 of Scheme I, where $R^1=R^3=R^4=R^5=R^6=R^7=H$, $R^2$=trifluoromethyl, $R^8$=acetoxymethyl, $R^9$=hydroxy n=0)

Compound 173 was prepared according to the general procedure described in Scheme I as a solid, $^1$H NMR (500 MHz, CDCl$_3$) 12.06 (s, 1H), 7.34 (d, J=9.0 Hz, 1H), 7.06 (dd, J=9.0, 2.4 Hz, 1H), 7.04 (s, 1H), 6.90 (m, 1H), 4.26-4.19 (m, 2H), 4.13 (m, 1H), 3.89 (m, 1H), 3.64 (m, 1H), 3.23 (m, 1H), 2.23-2.17 (m, 2H), 2.14 (s, 3H), 2.02-1.95 (m, 2H).

Example 42

6-(2(R)-(1 (R)-Hydroxy-2-chloroethyl)-1-pyrrolidinyl)-4-trifluoromethyl-2(1H)-quinolinone (Compound 174, Structure 10 of Scheme I, where $R^1=R^3=R^4=R^5=R^6=R^7=H$, $R^2$=trifluoromethyl, $R^8$=chloromethyl, $R^9$=hydroxy, n=0)

Compound 174 was prepared according to the general procedure described in Scheme I as a solid, $^1$H NMR (500 MHz, Acetone-d$_6$) 10.89 (s, 1H), 7.42 (d, J=9.0 Hz, 1H), 7.18 (dd, J=9.0, 2.4 Hz, if), 6.89 (qn, J=2.4 Hz, 1H), 6.88 (s, 1H), 4.54 (m, if, 4.16 (m, 1H), 4.08 (m, 1H), 3.68 (dd, J=11.0, 6.1 Hz, 1H), 3.62 (dd, J=11.0, 6.9 Hz, 1H), 3.61 (m, 1H), 3.22 (m, 1H), 2.25 (m, 2H), 1.98 (m, 2H).

Example 43

6-(2(R)-(2-Hydroxyethyl)-1-pyrrolidinyl)-4-trifluoromethyl-2(1H)-quinolinone (Compound 175, Structure 10 of Scheme I, where $R^1=R^3=R^4==R^6=R^7=R^8=H$, $R^2$=trifluoromethyl, $R^9$=hydroxymethyl, n=0)

Compound 175 was prepared according to the general procedure described in Scheme I as a solid, $^1$H NMR (500 MHz, CDCl$_3$) 10.92 (s, 1H), 7.39 (d, J=9.1 Hz, 1H), 7.18 (dd, J=9.1, 2.3 Hz, 1H), 6.86 (s, 1H), 6.83 (qn, J=2.3 Hz, 1H), 3.97 (m, 1H), 3.77-3.65 (m, 3H), 3.47 (m, 1H), 3.17 (m, if), 2.14-2.06 (m, 2H), 1.98-1.90 (m, 3H), 1.52 (m, 1H).

Example 44

6-(2(R)-(2-Oxoethyl)-1-pyrrolidinyl)-4-trifluoromethyl-2(1H)-quinolinone (Compound 176, Structure 10 of Scheme I, where $R^1=R^3=R^4=R^5=R^6=R^7=R^8=H$, $R^2$=trifluoromethyl, $R^9$=formyl, n=0)

Compound 176 was prepared according to the general procedure described in Scheme I as a solid, $^1$H NMR (500 k, CDCl$_3$) 11.26 (s, 1H), 9.88 (t, J=1.6 Hz, 1Hz), 7.29 (d, J=8.9 Hz, 1H), 7.06 (s, if), 6.96 (dd, J=8.9, 2.0 Hz, 1H), 6.81 (qn, J=2.0 Hz, 1H), 4.32 (m, 1H), 3.51 (m, 1H), 3.26 (m, 1H), 2.85 (dd, J=17.3, 2.6 Hz, 1H), 2.57 (ddd, J=17.3, 9.5, 2.0 Hz, 1H), 2.22 (m, 1H), 2.05-2.15 (m, 2H), 1.86 (m, 1H).

Example 45

6-(2(R)-Acetyloxymethyl-6(R)-methyl-1-piperidinyl)-4-trifluoromethyl-2(1)-quinolinone (Compound 177, Structure 10 of Scheme I, where $R^1=R^4=R^5=R^6=R^7=R^8=H$, $R^2$=trifluoromethyl, $R^3$=methyl, $R^9$=acetyloxy n=1)

Compound 177 was prepared according to the general procedure described in Scheme I as a solid, $^1$H NMR (500 MHz, CDCl$_3$) 12.45 (s, 1H), 7.53 (qn, J=1.9 Hz, 1H), 7.47 (dd, J=8.8, 1.9 Hz, 1H), 7.44 (d, J=8.8 Hz, 1H), 7.09 (s, 1H), 3.80 (dd, J=11.3, 3.7 Hz, 1H), 3.69 (dd, J=11.3, 6.2 Hz, 1H), 3.23 (m, 1H), 3.10 (m, 1H), 1.94 (s, 3H), 1.90-1.76 (m, 3H), 1.62-1.44 (m, 3H), 0.81 (d, J=6.1 Hz, 3H).

Example 46

6-(2(R)-(1(R)-Chloro-2-hydroxyethyl)-1-pyrrolidinyl)-4-trifluoromethyl-2(1H)-quinolinone (Compound 178, Structure 10 of Scheme I, where $R^1=R^3=R^4=R^5=R^6=R^8=H$, $R^2$=trifluoromethyl, $R^7$=hydroxymethyl, $R^9$=chloro, n=0)

Compound 178 was prepared according to the general procedure described in Scheme I as a solid, $^1$H NMR (500 MHz, Acetone-d$_6$) 10.92 (s, 1H), 7.43 (d, J=9.0 Hz, 1H), 7.24 (dd, J=9.0, 2.4 Hz, 1H), 6.93 (qn, J=2.4 Hz, 1H), 6.88 (s, 1H), 4.50-4.39 (m, 2H), 3.82-3.79 (m, 2H), 3.64 (m, 1H), 3.26 (m, 1H), 2.26 (m, 2H), 2.12 (m, 2H).

Example 47

6-(2(R)-Hydroxymethyl-6(R)-methyl-1-piperidinyl)-4-trifluoromethyl-2(1H)-quinolinone (Compound 179, Structure 10 of Scheme I, where $R^1=R^4=R^5=R^6=R^7=R^8=H$, $R^2$=trifluoromethyl, $R^3$=methyl, $R^9$=hydroxy, n=1)

Compound 179 was prepared according to the general procedure described in Scheme I as a solid, $^1$H NMR (500 MHz, CDCl$_3$) 12.43 (s, 1H), 7.61 (qn, J=2.0 Hz, 1H), 7.51 (dd, J=8.8, 2.0 Hz, 1H), 7.46 (d, J=8.8 Hz, 1H), 7.11 (s, 1H), 3.25 (m, 2H), 3.05 (m, 1H), 2.97 (m, 1H), 1.91-1.75 (m, 4H), 1.57 (m, 1H), 1.40 (m, 1H), 0.78 (d, J=6.1 Hz, 3H).

Example 48

6-(2(R)-(1(R)-Hydroxy-2,2,2-trifluoroethyl)-6(R)-methyl-1-piperidinyl)-4-trifluoromethyl-2(1H)-quinolinone (Compound 180, Structure 10 of Scheme I, where $R^1=R^4=R^5=R^8=H$, $R^2$=trifluoromethyl, $R^3$=methyl, $R^7$=trifluoromethyl, $R^9$=hydroxy, n=1)

Compound 180 was prepared according to the general procedure described in Scheme I as a solid, $^1$H NMR (500 MHz, CDCl$_3$) 12.48 (s, 1H), 7.67 (qn, J=1.8 Hz, 1H), 7.54-7.49 (m, 2H), 7.13 (s, 1H), 3.55 (dq, J=1.8, 7.7 Hz, 1H), 3.32 (m, 1H), 2.95 (m, 1H), 2.89 (m, 1H), 1.95-1.88 (m, 2H), 1.82-1.70 (m, 2H), 1.61-1.50 (m, 1H), 1.42-1.33 (m, 1H), 0.77 (d, J=6.1 Hz, 3H).

Example 49

6-(2(R)-(1(S)-Hydroxy-2,2,2-trifluoroethyl)-5(R)-methyl-1-pyrrolidinyl)-4-chlorodifluoromethyl-2(1H)-quinolinone (Compound 181, Structure 10 of Scheme I, where $R^1=R^4=R^5=R^6=R^7=H$, $R^2$=chlorodifluoromethyl, $R^3$=methyl, $R^8$=trifluoromethyl, $R^9$=hydroxy, n=0), and 6-(2(R)-(1(R)-Hydroxy-2,2,2-trifluoroethyl)-5(R)-methyl-1-pyrrolidinyl)-4-chlorodifluoromethyl-2(1H)-quinolinone (Compound 182, Structure 10 of Scheme I, where $R^1=R^4=R^5=R^6=R^8=H$, $R^2$=chlorodifluoromethyl, $R^3$=methyl, $R^7$=trifluoromethyl, $R^9$=hydroxy, n=0), and 6-(2-(R)-(1(S)-Hydroxy-2,2,2-trifluoroethyl)-5(S)-methyl-1-pyrrolidinyl)-4-chlorodifluoromethyl-2(1H)-quinolinone (Compound 183, Structure 10 of Scheme I, where $R^1=R^3=R^5=R^6=R^7=H$, $R^2$=chlorodifluoromethyl, $R^4$=methyl, $R^8$=trifluoromethyl, $R^9$=hydroxy, n=0)

These compounds were prepared by the general procedure as described in Scheme I as solids.

Compound 181: $^1$H NMR (500 MHz, Acetone-d$_6$) 10.89 (s, 1H), 7.40 (dd, J=9.1, 0.6 Hz, 1H), 7.37 (dd, J=9.1, 2.0 Hz, 1H), 7.32 (q, J=2.0 Hz, 1H), 6.81 (s, 1H), 5.33 (d, J=3.7 Hz, 1H), 4.11-4.05 (m, 2H), 3.83 (m, 1H), 2.31 (m, 1H), 2.01 (m, 2H), 1.87 (m, 1H), 1.38 (d, J=6.0 Hz, 3H).

Compound 182: $^1$H NMR (500 MHz, Acetone-d$_6$) 7.45 (d, J=9.0 Hz, 1H), 7.15 (dd, J=9.0, 2.0 Hz, 1H), 7.00 (q, J=2.0 Hz, 1H), 6.82 (s, if), 5.63 (m, 1H), 4.46 (m, 1H), 4.13 (m, 1H), 3.90 (m, 1H), 2.50 (m, 1H), 2.12 (m, 1H), 2.00 (m, 1H), 1.85 (m, 1H), 1.34 (d, J=6.3 Hz, 3H).

Compound 183: $^1$H NMR (500 MHz, Acetone-d$_6$) 7.38 (d, J=9.1 Hz, 1H), 7.26 (dd, J=9.1, 2.4 Hz, 1H), 7.12 (m, 1H), 6.80 (s, 1H), 5.45 (d, J=6.0 Hz, 1H), 4.36 (m, 1H), 4.28-4.17 (m, 2H), 2.40-2.24 (m, 2H), 2.14 (m, 1H), 1.76 (m, 1H), 1.11 (d, J=6.3 Hz, 3H).

Example 50

6-(2(R)-(2(S)-Hydroxy-3,3,3-trifluoropropyl)-1-pyrrolidinyl)-4-trifluoromethyl-2(1H)-quinolinone (Compound 184, Structure 10 of Scheme I, where $R^1=R^3=R^4=R^5=R^6=R^7=R^8=H$, $R^2$=trifluoromethyl, $R^9$=1(S)-hydroxy-2,2,2-trifluoroethyl, n=0) and 6-(2(R)-(2(R)-hydroxy-3,3,3-trifluoropropyl)-1-pyrrolidinyl-4-trifluoromethyl-2(1H)-quinolinone (Compound 185, Structure 10 of Scheme I, where $R^1=R^3=R^4=R^5=R^6=R^7=R^8=H$, $R^2$=trifluoromethyl $R^9$=1(R)-hydroxy-2,2,2-trifluoroethyl, n=0)

These compounds were prepared by the general procedure as described in Scheme I as solids.

Compound 184: $^1$H NMR (500 MHz, CDCl$_3$) 12.00 (s, 1H), 7.35 (d, J=9.1 Hz, 1H), 7.11 (dd, J=9.1, 2.2 Hz, 1H), 7.06 (s, 1H), 6.93 (qn, J=2.2 Hz, 1H), 4.12-4.04 (m, 2H), 3.58 (m, 1H, 3.20 (m, 1H), 2.82 (br s, 1H), 2.17-2.07 (m, 3H), 2.05-1.97 (m, 2H), 1.76 (ddd, J=14.6, 9.8, 6.5 Hz, 1H).

Compound 185: $^1$H NMR (500 MHz, CDCl$_3$) 11.07 (s, 1H), 7.29 (d, J=9.0 Hz, 1H), 7.08 (dd, J=9.0, 2.2 Hz, 1H), 7.04 (s, 1H), 6.93 (m, 1H), 4.10 (m, 1H), 4.01 (m, 1H), 3.52 (m, 1H), 3.24 (m, 1H), 2.13-1.98 (m, 5H), 1.87 (m, 1H).

Example 51

6-(2(R)-Acetyloxymethyl-6(R)-methyl-1-piperidinyl)-4-trifluoromethyl-2(1H)-quinolinone (Compound 186, Structure 10 of Scheme I, where $R^1=R^4=R^5=R^6=R^7=R^8=H$, $R^2=$trifluoromethyl, $R^3=$methyl, $R^9=$acetyloxy, n=1)

Compound 186 was prepared by the general procedure as described in Scheme I as solid: $^1$H NMR (500 MHz, CDCl$_3$) 12.45 (s, 1H), 7.53 (qn, J=1.9 Hz, 1H), 7.47 (dd, J=8.8, 1.9 Hz, 1H), 7.44 (d, J=8.8 Hz, 1H), 7.09 (s, 1H), 3.80 (dd, J=11.3, 3.7 Hz, 1H), 3.69 (dd, J=11.3, 6.2 Hz, 1H), 3.23 (m, 1H), 3.10 (m, 1H), 1.94 (s, 3H), 1.90-1.76 (m, 3H), 1.62-1.44 (m, 3H), 0.81 (d, J=6.1 Hz, 3H).

Example 52

6-(2(R)-(2Hydroxyethyl)-5(R)-methyl-1-pyrrolidinyl)-4-trifluoromethyl-2(1H)-quinolinone (Compound 187, Structure 10 of Scheme I, where $R^1=R^4=R^5=R^6=R^7=R^8=H$, $R^2=$trifluoromethyl, $R^3=$methyl, $R^9=$hydroxymethyl, n=0) and 6-(2(R)-(2-Hydroxyethyl)-5(S)-methyl-1-prrolidinyl)-4-trifluoromethyl-2(1H)-quinolinone (Compound 188, Structure 10 of Scheme I, where $R^1=R^3=R^5=R^6=R^7=R^8=H$, $R^2=$trifluoromethyl, $R^4=$methyl, $R^9=$hydroxymethyl, n=0).

These compounds were prepared by the general procedure as described in Scheme I as solids.

Compound 187: $^1$H NMR (500 MHz, CDCl$_3$) 7.24 (d, J=9.0 Hz, 1H), 7.12 (dd, J=9.0, 2.4 Hz, 1H), 7.04 (s, 1H), 6.96 (m, 1H), 3.91 (m, 1H), 3.87-3.76 (m, 3H), 2.20-2.01 (m, 4H), 1.87 (m, 1H), 1.77 (m, 1H), 1.31 (d, J=6.1 Hz, 3H).

Compound 188: $^1$H NMR (500 MHz, CDCl$_3$) 9.51 (s, 1H), 7.13-7.11 (m, 1H), 7.04-7.01 (m, 2H), 6.87 (m, 1H), 4.09-4.01 (m, 2H), 3.82 (m, 1H), 3.72 (m, 1H), 2.27-2.20 (m, 2H), 1.97-1.84 (m, 2H), 1.79-1.67 (m, 1H), 1.45 (m, 1H), 1.11 (d, J=6.1 Hz, 3H).

Example 53

6-(2(R)-Acetyloxyethyl-5(R)-methyl-1-pyrrolidinyl)-4-trifluoromethyl-2(1H)-quinolinone (Compound 189, Structure 10 of Scheme I, where $R^1=R^4=R^5=R^6=R^7=R^8=H$, $R^2=$trifluoromethyl, $R^3=$methyl, $R^9=$acetyloxymethyl, n=0)

Compound 189 was prepared by the general procedure as described in Scheme I as solid: $^1$H NMR (500 MHz, CDCl$_3$) 11.54 (s, 1H), 7.30 (d, J=9.1 Hz, 1H), 7.06 (s, 1H), 7.03 (dd, J=9.1, 2.4 Hz, 1H), 6.91 (m, 1H), 4.21-4.18 (m, 2H), 3.85-3.79 (m, 2H), 2.27-2.20 (m, 1H), 2.19-2.08 (m, 2H), 2.12 (s, 3H), 1.87 (m, 1H), 1.75 (m, 1H), 1.66 (m, 1H), 1.30 (d, J=6.3 Hz, 3H)

Example 54

6-(2(R)-(1(S)-Hydroxy-2,2,2-trifluoroethyl)-4(S)-fluoro-1-pyrrolidinyl)-4-trifluoromethyl-2(1H)-quinolinone (Compound 190, Structure 10 of Scheme I, where $R^1=R^3=R^4=R^5=R^7=H$, $R^2=$trifluoromethyl, $R^6=$fluoro, $R^1=$trifluoromethyl, $R^9$-hydroxy, n=0) and 6-(2(R)-(1(R)-Hydroxy-2,2,2-trifluoroethyl)-4(S)-fluoro-1-pyrrolidinyl)-4-trifluoromethyl-2(1H)-quinolinone (Compound 191, Structure 10 of Scheme I, where $R^1=R^3=R^4=R^5=R^8=H$, $R^2=$trifluoromethyl, $R^6=$fluoro, $R^7=$trifluoromethyl, $R^9=$hydroxy, n=0)

These compounds were prepared by the general procedure as described in Scheme I as solids.

Compound 190: $^1$H NMR (500 MHz, CDCl$_3$) 11.66 (s, if), 7.32 (d, J=9.0 Hz, 1H), 6.99 (dd, J=9.0, 2.5 Hz, 1H), 6.96 (s, 1H), 6.84 (m, 1H), 5.38 (dm, J=54.2 Hz, 1H), 4.51 (q, J=7.6 Hz, if), 4.46 (m, 1H), 3.75 (ddd, J=33.6, 11.2, 3.8 Hz, 1H), 3.62 (ddt, J=23.6, 11.2, 1.7 Hz, 1H), 2.75 (dddd, J=35.4, 13.3, 7.8, 6.6 Hz, 1H), 2.42 (m, 1H).

Compound 191: $^1$H NMR (500 MHz, CDCl$_3$) 11.49 (s, 1H), 7.29-7.24 (m, 2H), 7.11 (m, 1H), 7.00 (s, 1H), 5.35 (dm, J=53.1 Hz, 1H), 4.55 (m, 1H), 3.98 (m, 1H), 3.83 (ddd, J=31.7, 12.0, 3.7 Hz, 1H), 3.69 (ddt, J=21.7, 12.0, 1.9 Hz, 1H), 2.60 (m, 1H), 2.30 (dddd, J=31.7, 14.2, 6.1, 4.8 Hz, 1H).

Example 55

Co-Transfection Assay

CV-1 cells (African green monkey kidney fibroblasts) were cultured in the presence of Dulbecco's Modified Eagle Medium (DMEM) supplemented with 10% charcoal resin-stripped fetal bovine serum then transferred to 96-well microtiter plates one day prior to transfection.

To determine androgen receptor (AR) agonist and antagonist activity of the compounds of the present invention, the CV-1 cells were transiently transfected by calcium phosphate coprecipitation according to the procedure of Berger et al., *J. Steroid Biochem. Mol. Biol.*, 41:733 (1992) with the following plasmids: pShAR (5 ng/well), MWV-LUC reporter (100 ng/well), pRS-β-Gal (50 ng/well) and filler DNA (pGEM; 45 ng/well). The receptor plasmid, pRShAR, contains the human AR under constitutive control of the SV-40 promoter, as more fully described in Simental et al., *J. Biol. Chem.*, 266:510 (1991).

The reporter plasmid, MWV-LUC, contains the cDNA for firefly luciferase (LUC) under control of the mouse mammary tumor virus (MTV) long terminal repeat, a conditional promoter containing an androgen response element. See e.g., Berger et al. supra. In addition, pRS-β-Gal, coding for constitutive expression of *E. coli* β-galactosidase (β-Gal), was included as an internal control for evaluation of transfection efficiency and compound toxicity.

Six hours after transfection, media was removed and the cells were washed with phosphate-buffered saline (PBS). Media containing reference compounds (i.e. progesterone as a PR agonist, mifepristone ((11beta, 17beta)-11-[4-(dimethylamino)phenyl]-17-hydroxy-17-(1-propynyl)estra-4,9-dien-3-one: RU486; Roussel Uclaf) as a PR antagonist; dihydrotestosterone (DHT; Sigma Chemical) as an AR agonist and 2-OH-flutamide (the active metabolite of 2-methyl-N-[4-nitro-3-(trifluoromethyl)phenyl]pronanamide; Schering-Plough) as an AR antagonist; estradiol (Sigma) as an ER agonist and ICI 164,384 (N-butyl-3,17-dihydroxy-N-methyl-(7-alpha,17-beta)-estra-1,3,5(10)-triene-7-undecanamide; ICI Americas) as an ER antagonist; dexamethasone (Sigma) as a GR agonist and RU486 as a GR antagonist; and aldosterone (Sigma) as a MR agonist and spironolactone ((7-alpha-[acetylthio]-17-alpha-hydroxy-3-oxopregn-4-ene-21-carboxylic acid gamma-lactone; Sigma) as an MR antagonist) and/or the modulator compounds of the present invention in concentrations ranging from $10^{-12}$ to $10^{-5}$ M were added to the cells. Three to four replicates were used for each sample. Transfections and subsequent procedures were performed on a Biomek 1000 automated laboratory work station.

After 40 hours, the cells were washed with PBS, lysed with a Triton X-100-based buffer and assayed for LUC and β-Gal activities using a luminometer or spectrophotometer, respectively. For each replicate, the normalized response (NR) was calculated as:

LUC response/β-Gal rate where β-Gal rate=β-Gal·1×$10^{-5}$/β-Gal incubation time.

The mean and standard error of the mean (SEM) of the NR were calculated. Data was plotted as the response of the compound compared to the reference compounds over the range of the dose-response curve. For agonist experiments, the effective concentration that produced 50% of the maximum response ($EC_{50}$) was quantified. Agonist efficacy was a function (%) of LUC expression relative to the maximum LUC production by the reference agonist for PR, AR, ER, GR or MR. Antagonist activity was determined by testing the amount of LUC expression in the presence of a fixed amount of DHT as an AR agonist and progesterone as a PR agonist at the $EC_{50}$ concentration. The concentration of test compound that inhibited 50% of LUC expression induced by the reference agonist was quantified ($IC_{50}$). In addition, the efficacy of antagonists was determined as a function (%) of maximal inhibition.

IR Binding Assay

AR Binding: For the whole cell binding assay, COS-1 cells in 96-well microtiter plates containing DMEM-10% FBS were transfected as described above with the following plasmid DNA: pRShAR (2 ng/well), pRS-β-Gal (50 ng/well) and pGEM (48 ng/well). Six hours after transfection, media was removed, the cells were washed with PBS and fresh media was added. The next day, the media was changed to serum-free DMEM to remove any endogenous ligand that might be complexed with the receptor in the cells.

After 24 hours in serum-free media, either a saturation analysis to determine the $K_d$ for tritiated dihydrotestosterone ($^3$H-DHT) on human AR, or a competitive binding assay to evaluate the ability of test compound to compete with 3H-DHT for AR, was performed. For the saturation analysis, media (DMEM-0.2% charcoal adsorbed-FBS) containing $^3$H-DHT (in concentrations ranging from 12 nM to 0.24 nM) in the absence (total binding) or presence (non-specific binding) of a 100-fold molar excess of unlabeled DHT were added to the cells. For the competitive binding assay, media containing 1 nM $^3$H-DHT and test compounds in concentrations ranging from $10^{-10}$ to $10^{-6}$ M were added to the cells. Three replicates were used for each sample. After three hours at 37° C., an aliquot of the total binding media at each concentration of $^3$H-DHT was removed to estimate the amount of free $^3$H-DHT. The remaining media was removed, the cells were washed three times with PBS to remove unbound ligand, and cells were lysed with a Triton X-100-based buffer. The lysates were assayed for amount of bound $^3$H-DHT and β-Gal activity using a scintillation counter and spectrophotometer, respectively.

For the saturation analyses, the difference between the total binding and the nonspecific binding, normalized by the β-Gal rate, was defined as specific binding. The specific binding was evaluated by Scatchard analysis to determine the $K_d$ for $^3$H-DHT. See e.g., D. Rodbard, "Mathematics and statistics of ligand assays: an illustrated guide" In: J. Langon and J. J. Clapp, eds., *Ligand Assay*, Masson Publishing U.S.A., Inc., New York, pp. 45-99, (1981), the disclosure of which is herein incorporated by reference. For the competition studies, the data was plotted as the amount of $^3$H-DHT (% of control in the absence of test compound) remaining over the range of the dose-response curve for a given compound. The concentration of test compound that inhibited 50% of the amount of $^3$H-DHT bound in the absence of competing ligand was quantified ($IC_{50}$) after log-logit transformation. The $K_i$ values were determined by application of the Cheng-Prusoff equation to the $IC_{50}$ values, where:

$$IC_{50}$$

$$K_i = (1 + [^3H\text{-}DHT])/K_d \text{ for } ^3H\text{-}DHT$$

After correcting for non-specific binding, $IC_{50}$ values were determined. The $IC_{50}$ value is defined as the concentration of competing ligand needed to reduce specific binding by 50%. The $IC_{50}$ value was determined graphically from a log-logit plot of the data. The $K_i$ values were determined by application of the Cheng-Prusoff equation to the $IC_{50}$ values, the labeled ligand concentration and the $K_d$ of the labeled ligand.

Example 56

Hard gelatin capsules are prepared using the following ingredients:
Quantity
(mg/capsules)
COMPOUND 145 140
Starch, dried 100
Magnesium stearate 10
Total 250 mg The above ingredients are mixed and filled into hard gelatin capsules in 250 mg quantities.

A tablet is prepared using the ingredients below:
Quantity
(mg/capsule)
COMPOUND 145 140
Cellulose, microcrystalline 200
Silicon dioxide, fumed 10
Stearic acid 10
Total 360 mg The components are blended and compressed to form tablets each weighing 360 mg.

Tablets, each containing 60 mg of active ingredient, are made as follows:
Quantity
(mg/capsule)
COMPOUND 145 60
Starch 45
Cellulose, microcrystalline Polyvinylpyrrolidone (PVP) 35
(as 10% solution in water) 4
Sodium carboxymethyl starch (SCMS) 4.5
Magnesium stearate 0.5
Talc 1.0
Total 150 mg The active ingredient, starch, and cellulose are passed through a No. 45 mesh U.S. sieve and mixed thoroughly. The solution of PVP is mixed with the resultant powders, which are then passed through a No. 14 mesh U.S. sieve. The granules so produced are dried at 50° C. and passed through a No. 18 mesh U.S. sieve. The SCMS, magnesium stearate, and talc, previously passed through a No. 60 mesh U.S. sieve, and then added to the granules which, after mixing, are compressed on a tablet machine to yield tablets each weighing 150 mg.

Suppositories, each containing 225 mg of active ingredient, may be made as follows:
COMPOUND 145 225 mg
Saturated fatty acid glycerides 2,000 mg
Total 2,225 mg The active ingredient is passed through a No. 60 mesh U.S. sieve and suspended in the saturated fatty acid glycerides previously melted using the minimum heat necessary. The mixture is then poured into a suppository mold of normal 2 g capacity and allowed to cool.

An intravenous formulation may be prepared as follows:
COMPOUND 145 100 mg
Saturated fatty acid glycerides 1,000 mL
Total 1,000 mL The compound is dissolved in the glycerol and then the solution is slowly diluted with isotonic saline. The solution of the above ingredients is then administered intravenously at a rate of 1 mL per minute to a patient.

While description of various embodiments and processing conditions has been provided, the scope of the invention is not to be limited thereto or thereby. Various modifications and alterations of the present invention will be apparent to those skilled in the art without departing from the scope and spirit of the present invention.

What is claimed is:

1. A compound having the formula:

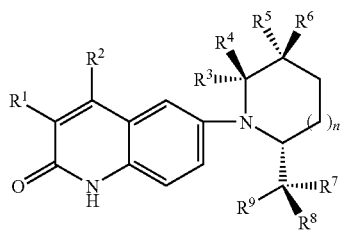

(I)

wherein:
$R^1$ is hydrogen, F, Cl, or $C_1$-$C_3$ aliphatic;
$R^2$ is hydrogen, F, Cl, Br, $C_1$-$C_4$ aliphatic, $C_1$-$C_4$ haloaliphatic or $C_1$-$C_4$ heteroaliphatic;
$R^3$ is $C_1$-$C_4$ aliphatic, $C_1$-$C_4$ haloaliphatic, $C_1$-$C_4$ heteroaliphatic, optionally substituted aryl or heteroaryl;
$R^4$ is hydrogen, $C_1$-$C_4$ aliphatic, $C_1$-$C_4$ haloaliphatic, $C_1$-$C_4$ heteroaliphatic, optionally substituted aryl or heteroaryl;
$R^5$ and $R^6$ each independently is hydrogen, F, Cl, $OR^{10}$, $C_1$-$C_4$ aliphatic, $C_1$-$C_4$ haloaliphatic or $C_1$-$C_4$ heteroaliphatic;
$R^7$ and $R^8$ each independently is hydrogen, F, Cl, $C_1$-$C_4$ aliphatic, $C_1$-$C_4$ haloaliphatic or $C_1$-$C_4$ heteroaliphatic; or
$R^7$ and $R^8$ taken together form a carbonyl group;
$R^9$ is halogen, $OR^{10}$, $SR^{10}$, $NR^{10}R^{11}$, $C_1$-$C_4$ haloaliphatic, $C_1$-$C_4$ heteroaliphatic, $C_1$-$C_4$ heterohaloaliphatic;
$R^{10}$ and $R^{11}$ each independently is hydrogen, $C_1$-$C_4$ aliphatic, phenyl or benzyl; and
n=0 or 1.

2. The compound of claim 1, wherein:
$R^1$ is hydrogen, F or Cl;
$R^2$ is F, Cl, Br, $C_1$-$C_4$ alkyl or $C_1$-$C_4$ haloalkyl;
$R^3$ is $C_1$-$C_4$ alkyl, $C_1$-$C_4$ haloalkyl or optionally substituted aryl;
$R^4$ is $C_1$-$C_4$ alkyl, $C_1$-$C_4$ haloalkyl or optionally substituted aryl;
$R^5$ and $R^6$ each independently is hydrogen, F, Cl, $OR^{10}$, $C_1$-$C_4$ alkyl or $C_1$-$C_4$ haloalkyl;
$R^7$ and $R^8$ each independently is hydrogen, F, Cl, $C_1$-$C_4$ alkyl or $C_1$-$C_4$ haloalkyl;
$R^9$ is halogen, $OR^{10}$, $C_1$-$C_4$ haloalkyl, $C_1$-$C_4$ heteroalkyl or $C_1$-$C_4$ heterohaloalkyl;
$R^{10}$ is hydrogen; and
n=0 or 1.

3. The compound of claim 1, wherein:
$R^1$ is hydrogen;
$R^2$ is Cl, Br, $CH_3$, $C_2H_5$, $CF_3$, $C_2F_5$ or $CF_2Cl$;
$R^3$ is $C_1$-$C_4$ alkyl, $C_1$-$C_4$ haloalkyl, $C_1$-$C_4$ heteroalkyl or optionally substituted aryl;
$R^4$ is hydrogen, $C_1$-$C_4$ alkyl, $C_1$-$C_4$ haloalkyl, $C_1$-$C_4$ heteroalkyl or optionally substituted aryl;

$R^5$ and $R^6$ each independently is hydrogen, F, Cl, $OR^{10}$, $C_1$-$C_4$ alkyl, $C_1$-$C_4$ haloalkyl or $C_1$-$C_4$ heteroalkyl;
$R^7$ and $R^8$ each independently is hydrogen, F, Cl, $C_1$-$C_4$ alkyl, $C_1$-$C_4$ haloalkyl or $C_1$-$C_4$ heteroalkyl;
$R^9$ is halogen, $OR^{10}$, $C_1$-$C_4$ haloalkyl, $C_1$-$C_4$ heteroalkyl or $C_1$-$C_4$ heterohaloalkyl;
$R^{10}$ is hydrogen or $C_1$-$C_4$ alkyl; and
n=0 or 1.

4. The compound of claim 1, wherein:
$R^1$ is hydrogen, F, Cl, or $C_1$-$C_3$ alkyl;
$R^2$ is hydrogen, F, Cl, Br, $C_1$-$C_4$ alkyl, $C_1$-$C_4$ haloalkyl or $C_1$-$C_4$ heteroalkyl;
$R^3$ is $C_1$-$C_4$ alkyl, $C_1$-$C_4$ haloalkyl, $C_1$-$C_4$ heteroalkyl, optionally substituted aryl or heteroaryl;
$R^4$ is hydrogen, $C_1$-$C_4$ alkyl, $C_1$-$C_4$ haloalkyl, $C_1$-$C_4$ heteroalkyl, optionally substituted aryl or heteroaryl;
$R^5$ and $R^6$ each is hydrogen;
$R^7$ and $R^8$ each independently is hydrogen, $C_1$-$C_4$ alkyl or $C_1$-$C_4$ haloalkyl;
$R^9$ is $OR^{10}$;
$R^{10}$ is hydrogen or $C_1$-$C_4$ alkyl; and
n=0.

5. The compound of claim 4, wherein:
$R^1$ is hydrogen;
$R^2$ is Cl, $CH_3$, $C_2H_5$, $CH_2F$, $CHF_2$, $CF_3$, $C_2F_5$ or $CF_2Cl$;
$R^3$ is $C_1$-$C_4$ alkyl;
$R^4$ is hydrogen or $C_1$-$C_4$ alkyl;
$R^7$ and $R^8$ each independently is hydrogen, $CH_3$, $C_2H_5$, $CF_3$, $C_2F_5$ or $CF_2Cl$; and
$R^9$ is OH.

6. The compound of claim 5, wherein:
$R^2$ is Cl, $CH_2F$, $CHF_2$, $CF_3$, $C_2F_5$ or $CF_2Cl$;
$R^3$ is $C_1$-$C_2$ alkyl;
$R^4$ is hydrogen or $C_1$-$C_2$ alkyl; and
$R^7$ and $R^8$ each independently is hydrogen, $CH_3$, $CF_3$, $C_2F_5$ or $CF_2Cl$.

7. The compound of claim 6, wherein:
$R^2$ is Cl, $CH_2F$, $CHF_2$, $CF_3$ or $CF_2Cl$;
$R^3$ is $CH_3$;
$R^4$ is hydrogen or $CH_3$; and
$R^7$ and $R^8$ each independently is hydrogen, $CH_3$, $CF_3$ or $CF_2Cl$.

8. The compound of claim 7, wherein:
$R^2$ is Cl, $CH_2F$, $CHF_2$, or $CF_3$;
$R^3$ is $CH_3$;
$R^4$ is hydrogen or $CH_3$; and
$R^7$ and $R^8$ each independently is hydrogen, $CH_3$ or $CF_3$.

9. The compound of claim 1, wherein the compound is an androgen receptor modulator.

10. The compound of claim 1, wherein the compound is an androgen receptor antagonist.

11. The compound of claim 1, wherein the compound is an androgen receptor agonist.

12. The compound of claim 1, wherein the compound is an androgen receptor partial agonist.

13. The compound of claim 1, wherein the compound is:
6-(2(R)-Hydroxymethyl-5(S)-methyl-1-pyrrolidinyl)-4-trifluoromethyl-2(1H)-quinolinone (Compound 106);
6-(2(R)-Fluoromethyl-5(R)-methyl-1-pyrrolidinyl)-4-trifluoromethyl-2(1H)- quinolinone (Compound 107);
6-(2(R)-Fluoromethyl-5(S)-methyl-1-pyrrolidinyl)-4-trifluoromethyl-2(1H)-quinolinone (Compound 108);
6-(2(R)-Difluoromethyl-5(R)-methyl-1-pyrrolidinyl)-4-trifluoromethyl-2(1H)-quinolinone (Compound 109);
6-(2(R)-Fluoromethyl-5(S)-methyl-1-pyrrolidinyl)-4-trifluoromethyl-2(1H)-quinolinone (Compound 110);

6-(2(R)-(1(R)-Hydroxy-2,2,2-trifluoroethyl)-5(S)-methyl-1-pyrrolidinyl)-4-trifluoromethyl-2(1H)-quinolinone (Compound 111);

6-(2(R)-(1(S)-Hydroxy-2,2,2-trifluoroethyl)-5(S)-methyl-1-pyrrolidinyl)-4-trifluoromethyl-21H)-quinolinone (Compound 112);

6-(2(R)-(1(S)-Hydroxy-2,2,2-trifluoroethyl)-5(R)-methyl-1-pyrrolidinyl)-4-trifluoromethyl-2(1H)-quinolinone (Compound 113);

6-(2(R)-(1(R)-Hydroxy-2,2,2-trifluoroethyl)-5(R)-methyl-1-pyrrolidinyl)-4-trifluoromethyl-2(1H)-quinolinone (Compound 114);

6-(2(R)-(2,2,2-Trifluoroethyl)-5(R)-methyl-1-pyrrolidinyl)-4-trifluoromethyl-2(1H)-quinolinone (Compound 115);

4-Chloro-6-(2(R)-(1(S)-hydroxy-2,2,2-trifluoroethyl)-5(R)-methyl-1-pyrrolidinyl)-2(1H)-quinolinone (Compound 128);

4-Chloro-6-(2(R)-(1(R)-hydroxy-2,2,2-trifluoroethyl)-5(R)-methyl-1-pyrrolidinyl)-2(1H)-quinolinone (Compound 129);

6-(2(R)-(1(R)-Hydroxy-1-methyl-2,2,2-trifluoroethyl)-5(R)-methyl-1-pyrrolidinyl)-4-trifluoromethyl-2(1H)-quinolinone (Compound 132);

6-(2(R)-(1(S)-Hydroxy-1-methyl-2,2,2-trifluoroethyl)-5(R)-methyl-1-pyrrolidinyl)-4-trifluoromethyl-2(1H)-quinolinone (Compound 133);

6-(2(R)-(1-Hydroxy-1-trifluoromethyl-2,2,2-trifluoroethyl)-5(R)-methyl-1-pyrrolidinyl )-4-trifluoromethyl-2(1H)-quinolinone (Compound 134);

6-(2(R)-Chloromethyl-5-(R)-methyl-1-pyrrolidinyl)-4-trifluoromethyl-2(1H)-quinolinone (Compound 140);

6-(2(R)-Chloromethyl-5-(S)-methyl-1-pyrrolidinyl)-4-trifluoromethyl-2(1H)-quinolinone (Compound 141);

6-(2(R)-(1(S)-Hydroxy-2,2,2-trifluoroethyl)-5(S)-phenyl-1-pyrrolidinyl)-4-trifluoromethyl-2(1H)-quinolinone (Compound 142);

6-(2(R)-(1(R)-Hydroxy-2,2,2-trifluoroethyl)-5(S)-phenyl-1-pyrrolidinyl)-4-trifluoromethyl-2(1H)-quinolinone (Compound 143);

6-(2(R)-(1(S)-Hydroxy-2,2,2-trifluoroethyl)-5,5-dimethyl-1-pyrrolidinyl)-4-trifluoromethyl-2(1H)-quinolinone (Compound 144);

6-(2(R)-(1(R)-Hydroxy-2,2,2-trifluoroethyl)-5,5-dimethyl-1-pyrrolidinyl)-4-trifluoromethyl-2(1H)-quinolinone (Compound 145);

6-(2(R)-(1(S)-Hydroxy-2,2,2-trifluoroethyl)-5(R)-phenyl-1-pyrrolidinyl)-4-trifluoromethyl-2(1H)-quinolinone (Compound 146);

6-(2(R)-(1(R)-Hydroxy-2,2,2-trifluoroethyl)-5(R)-phenyl-1-pyrrolidinyl)-4-trifluoromethyl-2(1H)-quinolinone (Compound 147);

6-(2(R)-(1(R)-Hydroxybenzyl)-5(S)-methyl-1-pyrrolidinyl)-4-trifluoromethyl-2(1H)-quinolinone (Compound 150);

6-(2(R)-(1(S)-Hydroxybenzyl)-5(R)-methyl-1-pyrrolidinyl)-4-trifluoromethyl-2(1H)-quinolinone (Compound 151);

6-(2(R)-(1(R)-Hydroxybenzyl)-5(R)-methyl-1-pyrrolidinyl)-4-trifluoromethyl-2(1H)-quinolinone (Compound 152);

6-(2(R)-((2-1,3-Dithianyl)-1(R)-hydroxymethyl)-5(R)-methyl-1-pyrrolidinyl)-4-trifluoromethyl-2(1H)-quinolinone (Compound 153);

6-(2(R)-((2-1,3-Dithianyl)-1(S)-hydroxymethyl)-5(R)-methyl-1-pyrrolidinyl)-4-trifluoromethyl-2(1H)-quinolinone (Compound 154);

6-(2(R)-Difluoromethyl-5,5-dimethyl-1-pyrrolidinyl)-4-trifluoromethyl-2(1H)-quinolinone (Compound 155);

6-(2(R)-Fluoromethyl-5,5-dimethyl-1-pyrrolidinyl)-4-trifluoromethyl-2(1H)-quinolinone (Compound 156);

6-(2(R)-Hydroxymethyl-5,5-dimethyl-1-pyrrolidinyl)-4-trifluoromethyl-2(1H)-quinolinone (Compound 157);

6-(2(R)-(1(R)-Hydroxyethyl)-5(R)-methyl-1-pyrrolidinyl)-4-trifluoromethyl-2(1H)-quinolinone (Compound 164);

6-(2(R)-(1-Hydroxy-1-methylethyl)-5(R)-methyl-1-pyrrolidinyl)-4-trifluoromethyl-2(1H)-quinolinone (Compound 165);

6-(2(R)-(1(S)-Hydroxy-1-cyclopropylmethyl)-5(R)-methyl-1-pyrrolidinyl)-4-trifluoromethyl-2(1H)-quinolinone (Compound 166);

6-(2(R)-(1(R)-Hydroxy-1-cyclopropylmethyl)-5(R)-methyl-1-pyrrolidinyl)-4-trifluoromethyl-2(1H)-quinolinone (Compound 167);

6-(2(R)-(1(S)-Hydroxypropyl)-5(R)-methyl-1-pyrrolidinyl)-4-trifluoromethyl-2(1H)-quinolinone (Compound 168), 6-(2(R)-(1(R)-Hydroxypropyl)-5(S)-methyl-1-pyrrolidinyl)-4-trifluoromethyl-2(1H)-quinolinone (Compound 169);

6-(2(R)-(1(R)-Hydroxypropyl)-5(R)-methyl-1-pyrrolidinyl)-4-trifluoromethyl-2(1H)-quinolinone (Compound 170);

6-2(R)-(1(S)-Hydroxypropyl)-5(S)-methyl-1-pyrrolidinyl)-4-trifluoromethyl-2(1H)-quinolinone (Compound 171);

6-(2(R)-(1(R)-Hydroxy-2-methylpropyl)-5(R)-methyl-1-pyrrolidinyl)-4-trifluoromethyl-2(1H)-quinolinone (Compound 172);

6-(2(R)-Acetyloxymethyl-6(R)-methyl-1-piperidinyl)-4-trifluoromethyl-2(1H)-quinolinone (Compound 177);

6-(2(R)-Hydroxymethyl-6(R)-methyl-1-piperidinyl)-4-trifluoromethyl-2(1H)-quinolinone (Compound 179);

6-(2(R)-(1(R)-Hydroxy-2,2,2-trifluoroethyl)-6(R)-methyl-1-piperidinyl)-4-trifluoromethyl-2(1H)-quinolinone (Compound 180);

6-(2(R)-(1(S)-Hydroxy-2,2,2-trifluoroethyl)-5(R)-methyl-1-pyrrolidinyl)-4-chloro-difluoromethyl-2(1H)-quinolinone (Compound 181);

6-(2(R)-(1(R)-Hydroxy-2,2,2-trifluoroethyl)-5(R)-methyl-1-pyrrolidinyl)-4-chloro-difluoromethyl-2(1H)-quinolinone (Compound 182);

6-(2(R)-(1(S)-Hydroxy-2,2,2-trifluoroethyl)-5(S)-methyl-1-pyrrolidinyl)-4-chloro-difluoromethyl-2(1H)-quinolinone (Compound 183);

6-(2(R)-Acetyloxymethyl-6(R)-methyl-1-piperidinyl)-4-trifluoromethyl-2(1H)-quinolinone (Compound 186);

6-(2(R)-(2-Hydroxyethyl)-5(R)-methyl-1-pyrrolidinyl)-4-trifluoromethyl-2(1H)-quinolinone (Compound 187);

6-(2(R)-(2-Hydroxyethyl)-5(S)-methyl-1-pyrrolidinyl)-4-trifluoromethyl-2(1H)-quinolinone (Compound 188); or 6-(2(R)-Acetyloxyethyl-5(R)-methyl-1-pyrrolidinyl)-4-trifluoromethyl-2(1H)-quinolinone (Compound 189).

14. A pharmaceutical composition, comprising a pharmaceutically acceptable carrier and compound of claim 1.

15. A pharmaceutical composition, comprising a pharmaceutically acceptable carrier and a compound of claim 2.

16. A pharmaceutical composition, comprising a pharmaceutically acceptable carrier and a compound of claim 7.

17. A pharmaceutical composition, comprising a pharmaceutically acceptable carrier and a compound of claim 8.

18. The pharmaceutical composition of claim 14, wherein the compound is an androgen receptor modulator.

19. The pharmaceutical composition of claim 18, wherein the compound is an androgen receptor antagonist.

20. The pharmaceutical composition of claim 18, wherein the compound is an androgen receptor agonist.

21. The pharmaceutical composition of claim 18, wherein the compound is an androgen receptor partial agonist.

22. The pharmaceutical composition of claim 14, wherein the compound is:

- 6-(2(R)-Hydroxymethyl-5(S)-methyl-1-pyrrolidinyl)-4-trifluoromethyl-2(1H)-quinolinone (Compound 106);
- 6-(2(R)-Fluoromethyl-5(R)-methyl-1-pyrrolidinyl)-4-trifluoromethyl-2(1H)-quinolinone (Compound 107);
- 6-(2(R)-Fluoromethyl-5(S)-methyl-1-pyrrolidinyl)-4-trifluoromethyl-2(1H)-quinolinone (Compound 108);
- 6-(2(R)-Difluoromethyl-5(R)-methyl-1-pyrrolidinyl)-4-trifluoromethyl-2(1H)-quinolinone (Compound 109);
- 6-(2(R)-Fluoromethyl-5(S)-methyl-1-pyrrolidinyl)-4-trifluoromethyl-2(1H)-quinolinone (Compound 110);
- 6-(2(R)-(1(R)-Hydroxy-2,2,2-trifluoroethyl)-5(S)-methyl-1-pyrrolidinyl)-4-trifluoromethyl-2(1H)-quinolinone (Compound 111);
- 6-(2(R)-(1(S)-Hydroxy-2,2,2-trifluoroethyl)-5(S)-methyl-1-pyrrolidinyl)-4-trifluoromethyl-2(1H)-quinolinone (Compound 112);
- 6-(2(R)-(1(S)-Hydroxy-2,2,2-trifluoroethyl)-5(R)-methyl-1-pyrrolidinyl)-4-trifluoromethyl-2(1H)-quinolinone (Compound 113);
- 6-(2(R)-(1(R)-Hydroxy-2,2,2-trifluoroethyl)-5(R)-methyl-1-pyrrolidinyl)-4-trifluoromethyl-2(1H)-quinolinone (Compound 114);
- 6-(2(R)-(2,2,2-Trifluoroethyl)-5(R)-methyl-1-pyrrolidinyl)-4-trifluoromethyl-2(1H)-quinolinone (Compound 115);
- 4-Chloro-6-(2(R)-(1(S)-hydroxy-2,2,2-trifluoroethyl)-5(R)-methyl-1-pyrrolidinyl)-2(1H)-quinolinone (Compound 128);
- 4-Chloro-6-(2(R)-(1(R)-hydroxy-2,2,2-trifluoroethyl)-5(R)-methyl-1-pyrrolidinyl)-2(1H)-quinolinone (Compound 129);
- 6-(2(R)-(1(R)-Hydroxy-1-methyl-2,2,2-trifluoroethyl)-5(R)-methyl-1-pyrrolidinyl)-4-trifluoromethyl-2(1H)-quinolinone (Compound 132);
- 6-(2(R)-(1(S)-Hydroxy-1-methyl-2,2,2-trifluoroethyl)-5(R)-methyl-1-pyrrolidinyl)-4-trifluoromethyl-2(1H)-quinolinone (Compound 133);
- 6-(2(R)-(1-Hydroxy-1-trifluoromethyl-2,2,2-trifluoroethyl)-5(R)-methyl-1-pyrrolidinyl )-4-trifluoromethyl-2(1H)-quinolinone (Compound 134);
- 6-(2(R)-Chloromethyl-5-(R)-methyl-1-pyrrolidinyl)-4-trifluoromethyl-2(1H)-quinolinone (Compound 140);
- 6-(2(R)-Chloromethyl-5-(S)-methyl-1-pyrrolidinyl)-4-trifluoromethyl-2(1H)-quinolinone (Compound 141);
- 6-(2(R)-(1(S)-Hydroxy-2,2,2-trifluoroethyl)-5(S)-phenyl-1-pyrrolidinyl)-4-trifluoromethyl-2(1H)-quinolinone (Compound 142);
- 6-(2(R)-(1(R)-Hydroxy-2,2,2-trifluoroethyl)-5(S)-phenyl-1-pyrrolidinyl)-4-trifluoromethyl-2(1H)-quinolinone (Compound 143);
- 6-(2(R)-(1(S)-Hydroxy-2,2,2-trifluoroethyl)-5,5-dimethyl-1-pyrrolidinyl)-4-trifluoromethyl-2(1H)-quinolinone (Compound 144);
- 6-(2(R)-(1(R)-Hydroxy-2,2,2-trifluoroethyl)-5,5-dimethyl-1-pyrrolidinyl)-4-trifluoromethyl-2(1H)-quinolinone (Compound 145);
- 6-(2(R)-(1(S)-Hydroxy-2,2,2-trifluoroethyl)-5(R)-phenyl-1-pyrrolidinyl)-4-trifluoromethyl-2(1H)-quinolinone (Compound 146);
- 6-(2(R)-(1(R)-Hydroxy-2,2,2-trifluoroethyl)-5(R)-phenyl-1-pyrrolidinyl)-4-trifluoromethyl-2(1H)-quinolinone (Compound 147);
- 6-(2(R)-(1(R)-Hydroxybenzyl)-5(S)-methyl-1-pyrrolidinyl)-4-trifluoromethyl-2(1H)-quinolinone (Compound 150);
- 6-(2(R)-(1(S)-Hydroxybenzyl)-5(R)-methyl-1-pyrrolidinyl)-4-trifluoromethyl-2(1H)-quinolinone (Compound 151);
- 6-(2(R)-(1(R)-Hydroxybenzyl)-5(R)-methyl-1-pyrrolidinyl)-4-trifluoromethyl-2(1H)-quinolinone (Compound 152);
- 6-(2(R)-((2-1,3-Dithianyl)-1(R)-hydroxymethyl)-5(R)-methyl-1-pyrrolidinyl)-4-trifluoromethyl-2(1H)-quinolinone (Compound 153);
- 6-(2(R)-((2-1,3-Dithianyl)-1(S)-hydroxymethyl)-5(R)-methyl-1-pyrrolidinyl)-4-trifluoromethyl-2(1H)-quinolinone (Compound 154);
- 6-(2(R)-Difluoromethyl-5,5-dimethyl-1-pyrrolidinyl)-4-trifluoromethyl-2(1H-quinolinone (Compound 155);
- 6-(2(R)-Fluoromethyl-5,5-dimethyl-1-pyrrolidinyl)-4-trifluoromethyl-2(1H)-quinolinone (Compound 156);
- 6-(2(R)-Hydroxymethyl-5,5-dimethyl-1-pyrrolidinyl)-4-trifluoromethyl-2(1H)-quinolinone (Compound 157);
- 6-(2(R)-(1(R)-Hydroxyethyl)-5(R)-methyl-1-pyrrolidinyl)-4-trifluoromethyl-2(1H)-quinolinone (Compound 164);
- 6-(2(R)-(1-Hydroxy-1-methylethyl)-5(R)-methyl-1-pyrrolidinyl)-4-trifluoromethyl-2(1H)-quinolinone (Compound 165);
- 6-(2(R)-(1(S)-Hydroxy-1-cyclopropylmethyl)-5(R)-methyl-1-pyrrolidinyl)-4-trifluoromethyl-2(1H)-quinolinone (Compound 166);
- 6-(2(R)-(1(R)-Hydroxy-1-cyclopropylmethyl)-5(R)-methyl-1-pyrrolidinyl)-4-trifluoromethyl-2(1H)-quinolinone (Compound 167);
- 6-(2(R)-(1(S)-Hydroxypropyl)-5(R)-methyl-1-pyrrolidinyl)-4-trifluoromethyl-2(1H)-quinolinone (Compound 168),
- 6-(2(R)-(1(R)-Hydroxypropyl)-5(S)-methyl-1-pyrrolidinyl)-4-trifluoromethyl-2(1H)-quinolinone (Compound 169);
- 6-(2(R)-(1(R)-Hydroxypropyl)-5(R)-methyl-1-pyrrolidinyl)-4-trifluoromethyl-2(1H)-quinolinone (Compound 170);
- 6-(2(R)-(1(S)-Hydroxypropyl)-5(S)-methyl-1-pyrrolidinyl)-4-trifluoromethyl-2(1H)-quinolinone (Compound 171);
- 6-(2(R)-(1(R)-Hydroxy-2-methylpropyl)-5(R)-methyl-1-pyrrolidinyl)-4-trifluoro-methyl-2(1H)-quinolinone (Compound 172);
- 6-(2(R)-Acetyloxymethyl-6(R)-methyl-1-piperidinyl)-4-trifluoromethyl-2(1H) -quinolinone (Compound 177);
- 6-(2(R)-Hydroxymethyl-6(R)-methyl-1-piperidinyl)-4-trifluoromethyl-2(1H)-quinolinone (Compound 179);
- 6-(2(R)-(1(R)-Hydroxy-2,2,2-trifluoroethyl)-6(R)-methyl-1-piperidinyl)-4-trifluoro-methyl-2(1H)-quinolinone (Compound 180);
- 6-(2(R)-(1(S)-Hydroxy-2,2,2-trifluoroethyl)-5(R)-methyl-1-pyrrolidinyl)-4-chloro-difluoromethyl-2(1H)-quinolinone (Compound 181);
- 6-(2(R)-(1(R)-Hydroxy-2,2,2-trifluoroethyl)-5(R)-methyl-1-pyrrolidinyl)-4-chloro-difluoromethyl-2(1H)-quinolinone (Compound 182);

6-(2(R)-(1(S)-Hydroxy-2,2,2-trifluoroethyl)-5(S)-methyl-1pyrrolidinyl)-4-chloro-difluoromethyl-2(1H)-quinolinone (Compound 183);

6-(2(R)-Acetyloxymethyl-6(R)-methyl-1-piperidinyl)-4-trifluoromethyl-2(1H)-quinolinone (Compound 186);

6-(2(R)-(2-Hydroxyethyl)-5(R)-methyl-1-pyrrolidinyl)-4-trifluoromethyl-2(1H)-quinolinone (Compound 187);

6-(2(R)-(2-Hydroxyethyl)-5(S)-methyl-1-pyrrolidinyl)-4-trifluoromethyl-2(1H)-quinolinone (Compound 188); or 6-(2(R)-Acetyloxyethyl-5(R)-methyl-1-pyrrolidinyl)-4-trifluoromethyl-2(1H)-quinolinone (Compound 189).

23. The pharmaceutical composition of claim 14, wherein the composition is formulated for oral, topical, intravenous, suppository or parenteral administration.

24. A method of treating an individual having a condition responsive to treatment with an androgen receptor agonist, comprising administering to the mammal a pharmaceutically effective amount of a compound of claim 1 that is an androgen receptor agonist and thereby treating the condition, wherein the condition is impotence, a wasting disease, hypogonadism, breast cancer, frailty, osteoporosis or cancer cachexia.

25. A method for treating an individual having a condition responsive to treatment with an androgen receptor antagonist, comprising administering the mammal a pharmaceutically effective amount of a compound of claim 1 that is an androgen receptor antagonist and thereby treating the condition, wherein the condition is acne, male-pattern baldness, hirsutism, prostatic hyperplasia or prostate cancer.

26. A method of providing a therapy to an individual, comprising:
administering to the individual a pharmaceutically effective amount of a compound of claim 1 that is an androgen receptor agonist or partial agonist., wherein the therapy is male hormone replacement therapy, stimulation of hematopoiesis or contraception.

27. The compound of claim 2, wherein the compound is an androgen receptor antagonist.

28. The compound of claim 2, wherein the compound is an androgen receptor agonist.

29. The compound of claim 2, wherein the compound is an androgen receptor partial agonist.

30. The pharmaceutical composition of claim 15, wherein the compound is an androgen receptor modulator.

31. The pharmaceutical composition of claim 30, wherein the compound is an androgen receptor antagonist.

32. The pharmaceutical composition of claim 30, wherein the compound is an androgen receptor agonist.

33. The pharmaceutical composition of claim 30, wherein the compound is an androgen receptor partial agonist.

34. The pharmaceutical composition of claim 16, wherein the compound is an androgen receptor modulator.

35. The pharmaceutical composition of claim 34, wherein the compound is an androgen receptor antagonist.

36. The pharmaceutical composition of claim 34, wherein the compound is an androgen receptor agonist.

37. The pharmaceutical composition of claim 34, wherein the compound is an androgen receptor partial agonist.

38. The pharmaceutical composition of claim 17, wherein the compound is an androgen receptor modulator.

39. The pharmaceutical composition of claim 38, wherein the compound is an androgen receptor antagonist.

40. The pharmaceutical composition of claim 38, wherein the compound is an androgen receptor agonist.

41. The pharmaceutical composition of claim 38, wherein the compound is an androgen receptor partial agonist.

42. A method of treating prostate cancer in a subject, comprising administering to the subject a pharmaceutically effective amount of a compound of claim 1 that is an androgen receptor antagonist.

* * * * *